(12) United States Patent
Fernandes et al.

(10) Patent No.: US 11,672,861 B2
(45) Date of Patent: Jun. 13, 2023

(54) PRUSSIAN BLUE NANOPARTICLES FUNCTIONALIZED WITH IMMUNE SIGNALS AND APPLICATIONS THEREOF

(71) Applicant: The George Washington University, Washington, DC (US)

(72) Inventors: Rohan Fernandes, Bethesda, MD (US); Elizabeth Sweeney, Washington, DC (US); Juliana Cano-Mejia, Arlington, VA (US)

(73) Assignee: The George Washington University, Washington, DC (US)

( * ) Notice: Subject to any disclaimer, the term of this patent is extended or adjusted under 35 U.S.C. 154(b) by 980 days.

(21) Appl. No.: 16/358,468

(22) Filed: Mar. 19, 2019

(65) Prior Publication Data

US 2020/0114005 A1   Apr. 16, 2020

Related U.S. Application Data

(60) Provisional application No. 62/745,843, filed on Oct. 15, 2018.

(51) Int. Cl.
| | |
|---|---|
| *A61K 41/00* | (2020.01) |
| *A61K 33/26* | (2006.01) |
| *A61K 31/7088* | (2006.01) |
| *A61K 9/51* | (2006.01) |
| *A61N 5/06* | (2006.01) |
| *A61B 5/00* | (2006.01) |
| *A61B 5/055* | (2006.01) |
| *A61K 9/50* | (2006.01) |
| *A61K 38/19* | (2006.01) |
| *A61B 6/00* | (2006.01) |
| *A61B 8/08* | (2006.01) |

(52) U.S. Cl.
CPC ........ *A61K 41/0052* (2013.01); *A61B 5/0071* (2013.01); *A61B 5/055* (2013.01); *A61B 6/481* (2013.01); *A61B 8/481* (2013.01); *A61K 9/5052* (2013.01); *A61K 9/51* (2013.01); *A61K 31/7088* (2013.01); *A61K 33/26* (2013.01); *A61K 38/19* (2013.01); *A61N 5/062* (2013.01)

(58) Field of Classification Search
None
See application file for complete search history.

(56) References Cited

U.S. PATENT DOCUMENTS

| | | | |
|---|---|---|---|
| 9,561,183 B2* | 2/2017 | Fernandes | A61K 41/0052 |
| 9,987,378 B2* | 6/2018 | Fernandes | A61K 41/0052 |

(Continued)

OTHER PUBLICATIONS

Henri J. Huttunen et al. "Receptor for Advanced Glycation End Products-binding COOH-terminal Motif of Amphoterin Inhibits Invasive Migration and Metastasis." Cancer Research, vol. 62, Aug. 15, 2002, pp. 4805-4811. (Year: 2002).*

(Continued)

*Primary Examiner* — Isaac Shomer
(74) *Attorney, Agent, or Firm* — Kory D. Christensen

(57) ABSTRACT

Biofunctionalized nanocomposites comprised of a core nanoparticle formed of Prussian blue materials, a shell obtained by partially or completely encapsulating the Prussian blue core with a biocompatible coating, and at least one biomolecule attached to, or absorbed to, the biocompatible coating and uses thereof.

7 Claims, 29 Drawing Sheets

(56) References Cited

U.S. PATENT DOCUMENTS

| | | | | |
|---|---|---|---|---|
| 2007/0238663 | A1* | 10/2007 | Capogrossi | A61K 38/17 514/18.9 |
| 2010/0055189 | A1* | 3/2010 | Hubbell | A61K 39/00 1106 977/773 |
| 2012/0207795 | A1* | 8/2012 | Zink | A61K 9/5192 977/773 |
| 2014/0271487 | A1* | 9/2014 | Fernandes | A61K 9/143 424/490 |
| 2014/0314855 | A1* | 10/2014 | Ducheyne | A61K 9/5192 424/490 |

OTHER PUBLICATIONS

Mikhail G. Kolonin et al. "Interaction between Tumor Cell Surface Receptor RAGE and Proteinase 3 Mediates Prostate Cancer Metastasis to Bone." Cancer Research, vol. 77(12), Jun. 15, 2017, pp. 3144-3150. (Year: 2017).*

Bernd Jahrsdorfer and George J. Weiner. "CpG oligodeoxynucleotides as immunotherapy in cancer." Update on Cancer Therapeutics, vol. 3, 2008, pp. 27-32. (Year: 2008).*

Akihiko Taguchi et al. "Blockade of RAGE-amphoterin signalling suppresses tumour growth and metastases." Nature, vol. 405, May 18, 2000, pp. 354-360. (Year: 2000).*

E. Sweeney et al., Photothermal Therapy Generates a Thermal Window of Immunogenic Cell Death in Neuroblastoma, Advanced Science News, Small. 2018. vol. 14. 1800678. pp. 1-8. (Year: 2018).*

Kevin J. Kauffman et al. "Optimization of Lipid Nanoparticle Formulations for mRNA Delivery in Vivo with Fractional Factorial and Definitive Screening Designs." Nano Letters, vol. 15, 2015, pp. 7300-7306. (Year: 2015).*

Cano-Mejia et al., "Prussian Blue Nanoparticule-Based Photothermal Therapy Combined with Checkpoint Inhibition for Photothermal Immunotherapy of Neuroblastoma," Nanomedicine: Nanotechnology, Biology, and Medicine 13 (2017) pp. 771-781.

Chen et al., Combining Photothermal Therapy and Immunotherapy against Melanoma by Polydopamine-Coated $Al_2O_3$ Nanoparticles, Theranostics 2018, vol. 8, Issue 8, pp. 2229-2241.

Goldberg, "Immunoengineering: How Nanotechnology Can Enhance Cancer Immunotherapy," Cell 161, Apr. 9, 2015, pp. 201-204.

Guo et al., "Combinatorial Photothermal and Immuno Cancer Therapy Using Chitosan-Coated Hollow Copper Sulfide Nanoparticles," ACS NANO, vol. 8, No. 6, 2014, pp. 5670-5681.

Han et al., "CpG Loaded $MoS_2$ Nanosheets as Multifunctional Agents for Photothermal Enhanced Cancer Immunotherapy," The Royal Society of Chemistry, Nanoscale, vol. 9, 2017, pp. 5927-5934.

Hoffman et al., Prussian Blue Nanoparticles for Laser-Induced Photothermal Therapy of Tumors, Royal Society of Chemistry, RSC Adv., 2014, pp. 29729-29734.

Li et al., "Fever-Inspired Immunotherapy Based on Photothermal CpG Nanotherapeutics: The Critical Role of Mild Heat in Regulating Tumor Microenvironment," Advanced Science, vol. 5, 2018, 1700805, pp. 1-12.

Sweeney et al., Photothermal Therapy Generates a Thermal Window of Immunogenic Cell Death in Neuroblastoma, Advanced Science News, Small, 2018. vol. 14, 1800678, pp. 1-8.

Tao et al., Immunostimulatory Oligonucleotides-Loaded Cationic Graphene Oxide with Photothermally Enhanced Immunogenicity for Photothermal/Immune Cancer Therapy, Elsevier, Biomaterials vol. 35, 2014, pp. 9963-9971.

Tao e al., Engineered, Self-Assembled Near-Infrared Photothermal Agents for Combined Tumor Immunotherapy and Chemo-Photothermal Therapy, Elsevier, Biomaterials, vol. 35, 2014, pp. 6646-6656.

* cited by examiner

| Group | Treatment |
|---|---|
| CpG-PBNP-PTT | CpG-PBNP-PTT on day 0; CpG-PBNP on days 2, 5 |
| PBNP-PTT | PTT on day 0 |
| Free CpG-PBNPs | CpG- PBNPs on days 0, 2, 5 |
| Free CpG | CpG on days 0, 2, 5 |
| Vehicle | No treatment |

PRUSSIAN BLUE NANOPARTICLES FUNCTIONALIZED WITH IMMUNE SIGNALS AND APPLICATIONS THEREOF

CROSS REFERENCE TO RELATED APPLICATION

This application claims the benefit of U.S. Provisional Application No. 62/745,843, filed on Oct. 15, 2018, the disclosure of which is hereby incorporated by reference in its entirety.

FIELD

The present disclosure generally relates to compositions and methods for the treatment of tumor cells, prevention of tumor cell metastasis, and treatment and prevention of cancer using photothermal therapy.

BACKGROUND

Thermal therapy regimens are of great interest in oncology, physiotherapy, urology, cardiology, and ophthalmology, as well as other areas of medicine. Of particular interest is the use of thermal therapy in the management of cancer. Laser-induced photothermal ablation has been successfully employed for the ablation of tumors throughout the body; however, the energy of a visible laser can be absorbed by both healthy and cancerous tissues, leading to a possibility of damage in non-cancerous tissues. To improve efficacy and selectivity of laser-induced photothermal ablation, light-absorbing materials, or photothermal therapy agents, are introduced into the tumor. The advantage of these photothermal therapy agents are that they can locally convert absorbed light into heat, which results in the ablation of malignant tissue noninvasively by heating the tissue locally, while keeping the temperature of the surrounding tissue at a normal level. Use of photothermal therapy agents in this manner is the basis of the photothermal therapy (PTT).

Thus far, implementation of PTT has made incremental but limited progress in treating/preventing cancer. Although PTT ablates most of the tumor, the tumor is not completely eradicated. As such, the problem with PTT therapy in the current field is that it is ineffective in preventing relapse of cancerous disease. Accordingly, there is a need in the field to improve PTT beginning with the design of the photothermal therapy agents which are the underlying mechanism in successful PTT outcomes.

SUMMARY

In an aspect, the disclosure provides a biofunctionalized nanocomposite composition comprising (a) a core comprising a nanoparticle formed of Prussian blue materials; (b) a shell obtained by partially or completely encapsulating the Prussian blue core with a biocompatible coating; and (c) at least one biomolecule attached to, or absorbed to, the biocompatible coating.

The Prussian blue materials that comprise the core of the biofunctionalized nanocomposite can be iron hexacyanoferrate (II) compounds or materials represented by general formula (I):

(I)

wherein:

A represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

B represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

M represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

M' represents at least one of VO2, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

x is from 0.1 to about 1; y is from 0.1 to about 1; z is from 0.1 to about 4; and n is from 0.1 to about 24.

The biocompatible coating of the shell of the biofunctionalized nanocomposite can comprise at least one member selected from the group consisting of dextran, chitosan, silica, polyethylene glycol (PEG), avidin; a protein, a nucleic acid, a carbohydrate, a lipid, neutravidin, streptavidin, gelatin, collagen, fibronectin, albumin, a serum protein, a lysozyme, a phospholipid, a polyvinyl pyrrolidone (PVP), a polyvinyl alcohol, polyethylene glycol diacrylate, and polyethylenimine (PEI). Specifically, the biocompatible coating can comprise polyethylene glycol (PEG), a polyvinyl pyrrolidone (PVP), a polyvinyl alcohol, polyethylenimine (PEI), or a combination thereof.

The biomolecule attached to, or absorbed to, the biocompatible coating of the biofunctionalized nanocomposite can comprise at least one member selected from the group consisting of an antibody, a peptide, a protein, an enzyme, an amino acid, a nucleic acid, a carbohydrate, a fat, an aptamer, a small molecule, and a synthetic molecule. Specifically, the biomolecule can comprise a peptide. Further, the peptide can consist of 50 amino acids or less, excluding zero. Also specifically, the biomolecule can comprise a nucleic acid. Further, the nucleic acid can consist of an oligonucleotide.

The biocompatible coating of the shell of the biofunctionalized nanocomposite can further comprise an imaging agent wherein the imaging agent can comprise at least one member selected from the group consisting of a fluorescein compound, a rhodamine compound, a xanthene compound, a cyanine compound, a naphthalene compound, a coumarin compound, an oxadiazole compound, a pyrene compound, an oxazine compound, an acridine compound, an arylmethine compound, a tetrapyrrole compound, and a proprietary molecule.

In another aspect, the disclosure provides a photothermal therapy agent comprising (a) a core comprising a nanoparticle formed of Prussian blue materials; (b) a shell obtained by partially or completely encapsulating the Prussian blue core with a biocompatible coating; and (c) at least one biomolecule attached to, or absorbed to, the biocompatible coating.

The Prussian blue materials that comprise the core of the photothermal therapy agent can be iron hexacyanoferrate (II) compounds or materials represented by general formula (T):

(I)

wherein:

A represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

B represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

M represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

M' represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

x is from 0.1 to about 1; y is from 0.1 to about 1; z is from 0.1 to about 4; and n is from 0.1 to about 24.

The biocompatible coating of the shell of the photothermal therapy agent can comprise at least one member selected from the group consisting of dextran, chitosan, silica, polyethylene glycol (PEG), avidin; a protein, a nucleic acid, a carbohydrate, a lipid, neutravidin, streptavidin, gelatin, collagen, fibronectin, albumin, a serum protein, a lysozyme, a phospholipid, a polyvinyl pyrrolidone (PVP), a polyvinyl alcohol, polyethylene glycol diacrylate, and polyethylenimine (PEI). Specifically, the biocompatible coating can comprise polyethylene glycol (PEG), a polyvinyl pyrrolidone (PVP), a polyvinyl alcohol, polyethylenimine (PEI), or a combination thereof.

The biomolecule attached to, or absorbed to, the biocompatible coating of the photothermal therapy agent can comprise at least one member selected from the group consisting of an antibody, a peptide, a protein, an enzyme, an amino acid, a nucleic acid, a carbohydrate, a fat, an aptamer, a small molecule, and a synthetic molecule. Specifically, the biomolecule can comprise a peptide. Further, the peptide can consist of 50 amino acids or less, excluding zero. Also specifically, the biomolecule can comprise a nucleic acid. Further, the nucleic acid can consist of an oligonucleotide.

The biocompatible coating of the shell of the photothermal therapy agent can further comprise an imaging agent wherein the imaging agent can comprise at least one member selected from the group consisting of a fluorescein compound, a rhodamine compound, a xanthene compound, a cyanine compound, a naphthalene compound, a coumarin compound, an oxadiazole compound, a pyrene compound, an oxazine compound, an acridine compound, an arylmethine compound, a tetrapyrrole compound, and a proprietary molecule.

The photothermal therapy agent can be stable at no less than 80° C. The photothermal therapy agent can be stable for at least 7 days.

In yet another aspect, the disclosure provides a method of treating at least one tumor cell in a subject in need thereof, the method comprising: (a) administering to a subject a biofunctionalized nanocomposite as disclosed; and (b) subjecting the subject to photothermal therapy. The method can be performed at least once a week for at least 3 weeks.

The photothermal therapy of the method can comprise the use of a device that emits electromagnetic radiation with a wavelength that irradiates the biofunctionalized nanocomposite. Specifically, the method of irradiating the biofunctionalized nanocomposite comprises a device that emits electromagnetic radiation with a wavelength between about 600 nm and 1000 nm.

In another aspect, the disclosure provides a method of preventing metastasis of at least one tumor cell, the method comprising: (a) administering to a subject a biofunctionalized nanocomposite as disclosed; and (b) subjecting the subject to photothermal therapy. The method can be performed at least once a week for at least 3 weeks.

The photothermal therapy of the method can comprise the use of a device that emits electromagnetic radiation with a wavelength that irradiates the biofunctionalized nanocomposite. Specifically, the method of irradiating the biofunctionalized nanocomposite comprises a device that emits electromagnetic radiation with a wavelength between about 600 nm and 1000 nm.

In yet another aspect, the disclosure provides a method of treating and/or preventing cancer in a subject in need thereof, the method comprising: (a) administering to the subject a biofunctionalized nanocomposite as disclosed; and (b) subjecting the subject to photothermal therapy at least once a week for at least 3 weeks, wherein the photothermal therapy comprises the use of a device that emits electromagnetic radiation with a wavelength between about 600 nm and 1000 nm that irradiates the biofunctionalized nanocomposite.

Figure 4A:
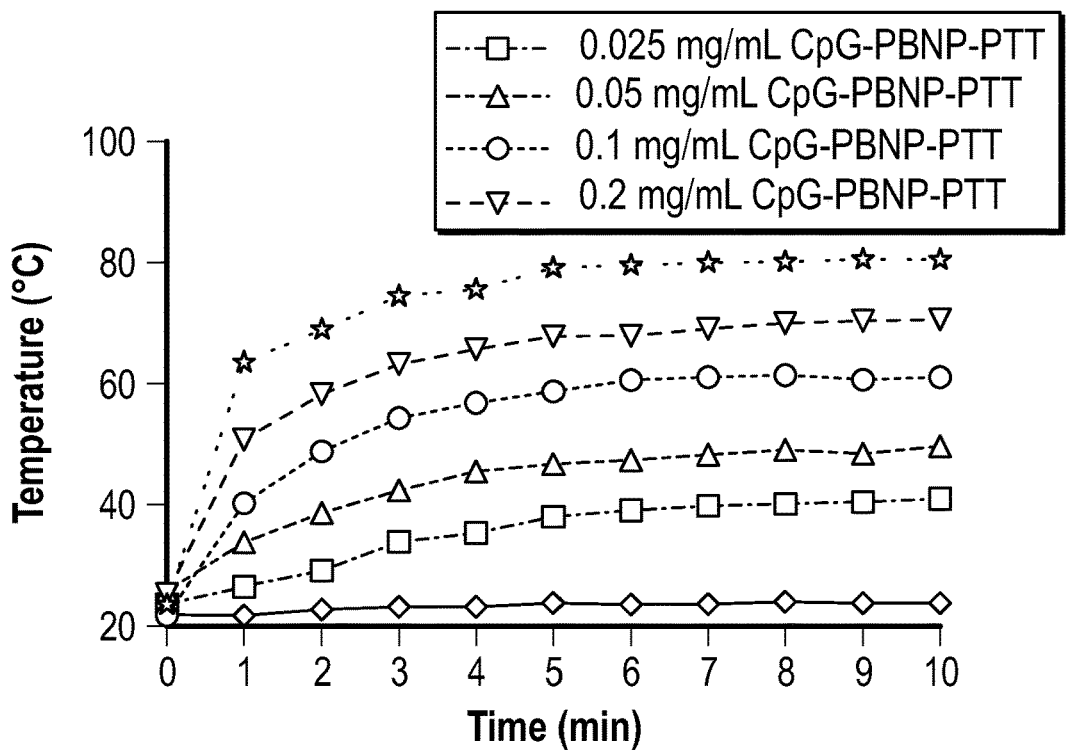
FIG. 4A depicts a graph showing the photothermal heating characteristics of CpG-PBNPs following photo-thermal heating of 0.025 mg/mL, 0.05 mg/mL, 0.1 mg/mL, and 0.2 mg/mL CpG-PBNPs irradiated by an 808 nm NIR laser for 10 minutes at 0.75 W cm² power.
Figure 4B:
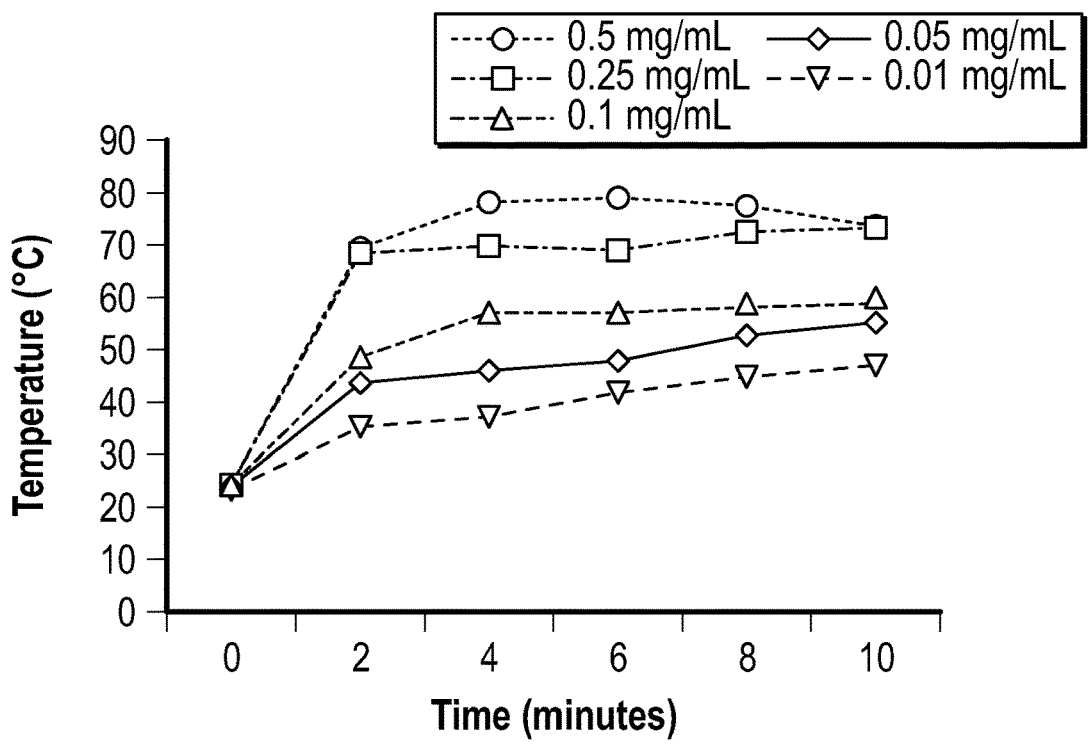

FIG. 4B depicts a graph showing the photothermal heating characteristics of CpG-PBNPs following photo-thermal heating of 0.01 mg/mL, 0.05 mg/mL, 0.1 mg/mL, 0.25 mg/mL, and 0.5 mg/mL CpG-PBNPs irradiated by an 808 nm NIR laser for 10 minutes at 0.75 W cm² power.

Figure 4C:
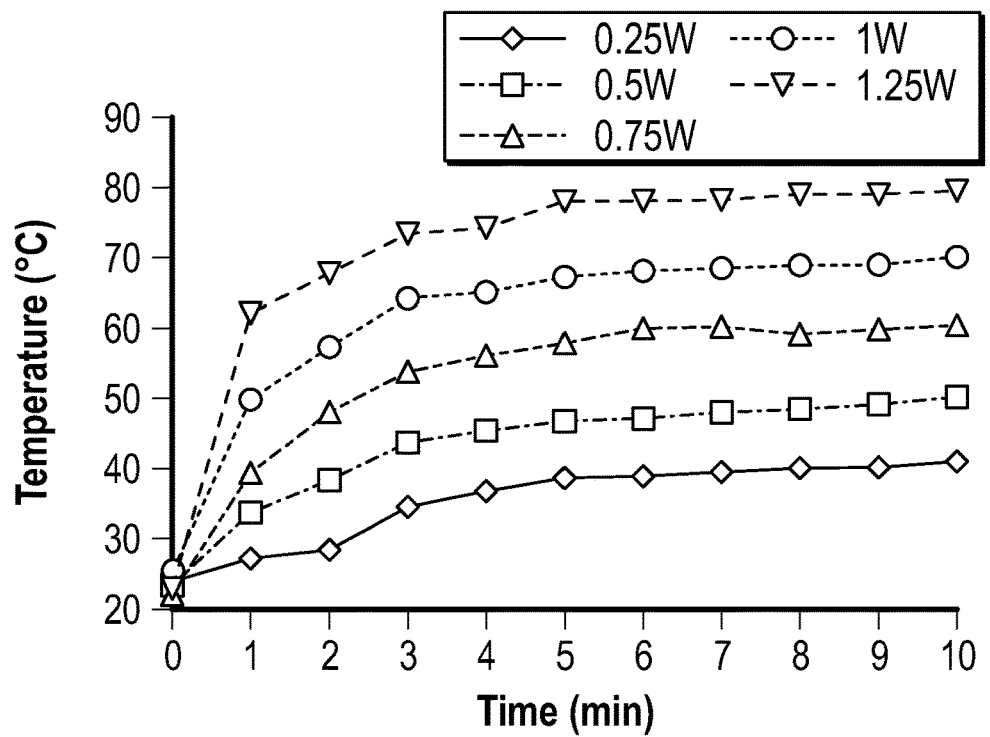

FIG. 4C depicts a graph showing the photothermal heating characteristics of 1 mg/mL CpG-PBNPs following irradiation by a NIR laser at powers of 0.25 W/cm², 0.5 W/cm², 0.75 W/cm², 1.0 W/cm², and 1.25 W cm² for 10 minutes.

Figure 4D:
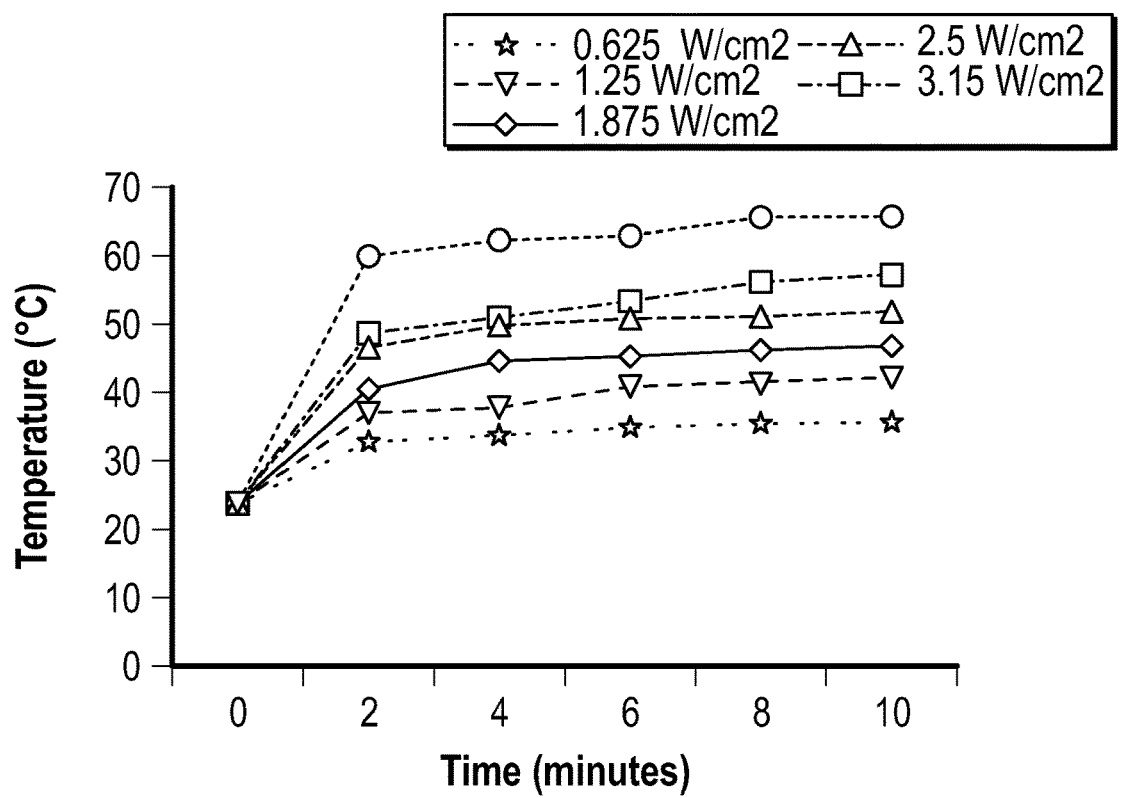

FIG. 4D depicts a graph showing the photothermal heating characteristics of 1 mg/mL CpG-PBNPs following irradiation by a NIR laser at powers of 0.625 W/cm², 1.25 W/cm², 1.875 W/cm², 2.5 W/cm², and 3.15 W cm² for 10 minutes.

Figure 4E:
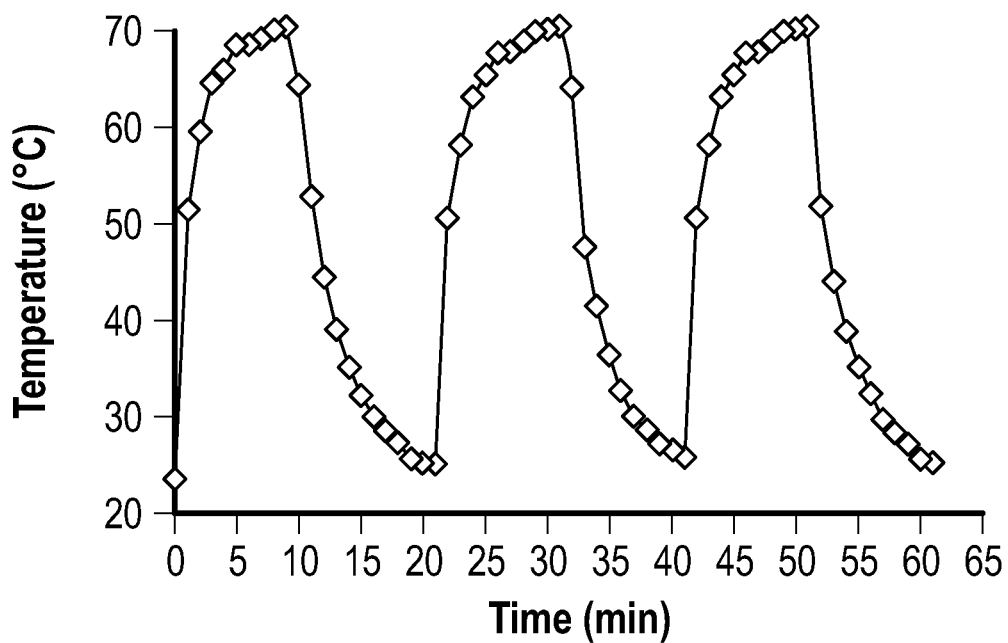

FIG. 4E depicts a graph showing the temperature profiles of 1 mg/mL CpG-PBNPs during four consecutive heating and cooling cycles using an 808 nm NIR laser wherein each cycle was 10 minutes long.

Figure 4F:
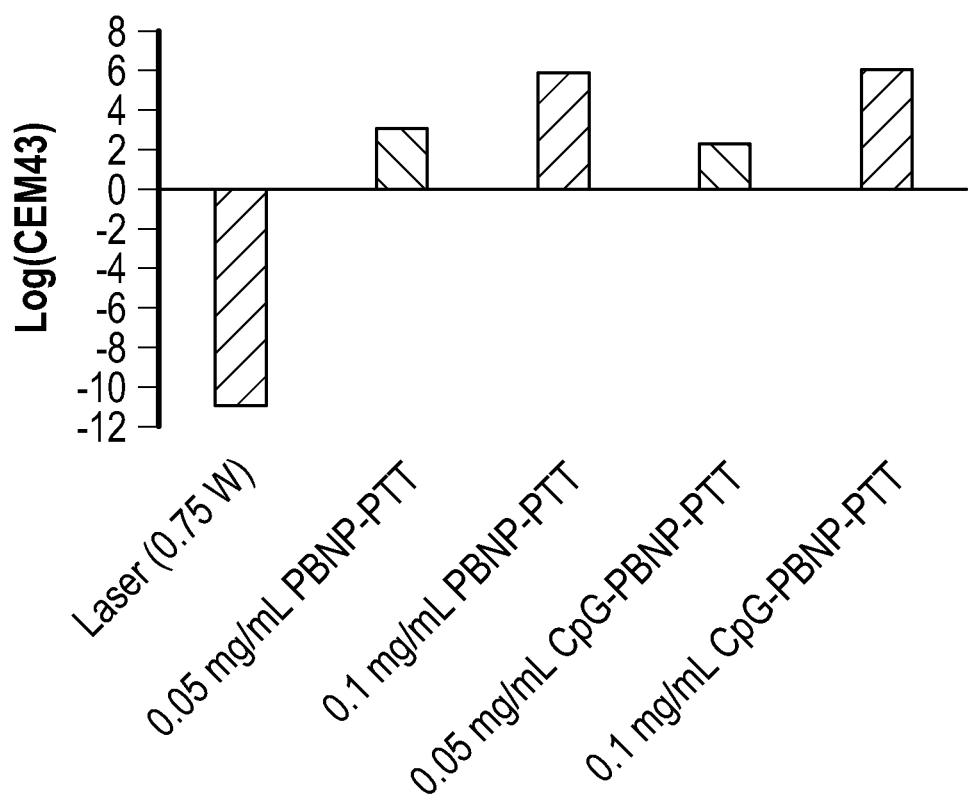

FIG. 4F depicts a graph showing the thermal damage caused by photothermal heating with a NIR laser (75 W/cm²) for 0.05 mg/mL uncoated PBNPs, 0.1 mg/mL uncoated PBNPs, 0.05 mg/mL CpG-PBNPs, and 0.1 mg/mL CpG-PBNPs using the CEM43° C. thermal dose model.

Figure 5A:
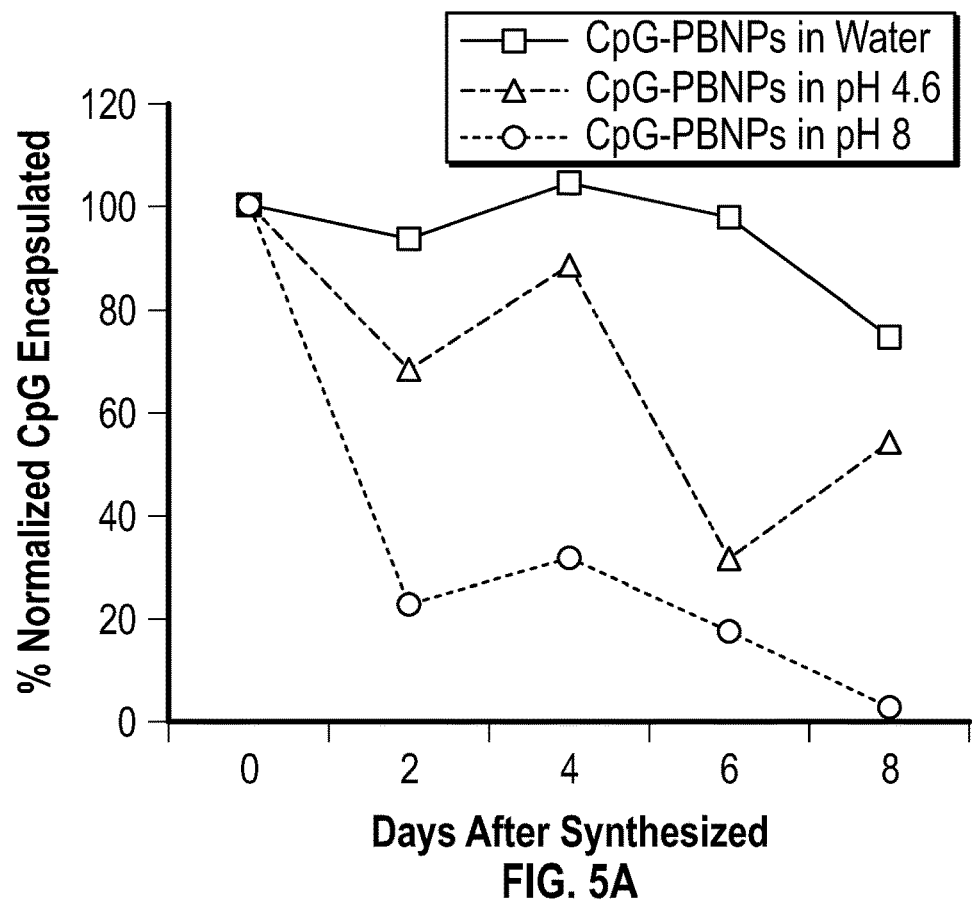

FIG. 5A depicts a graph showing the rate that CpG encapsulation is decreased after CpG-PBNPs are incubated for 0, 2, 4, 6, and 8 days in water (pH 7), a solution with a pH of 4.6, and a solution with a pH of 8.

Figure 5B:
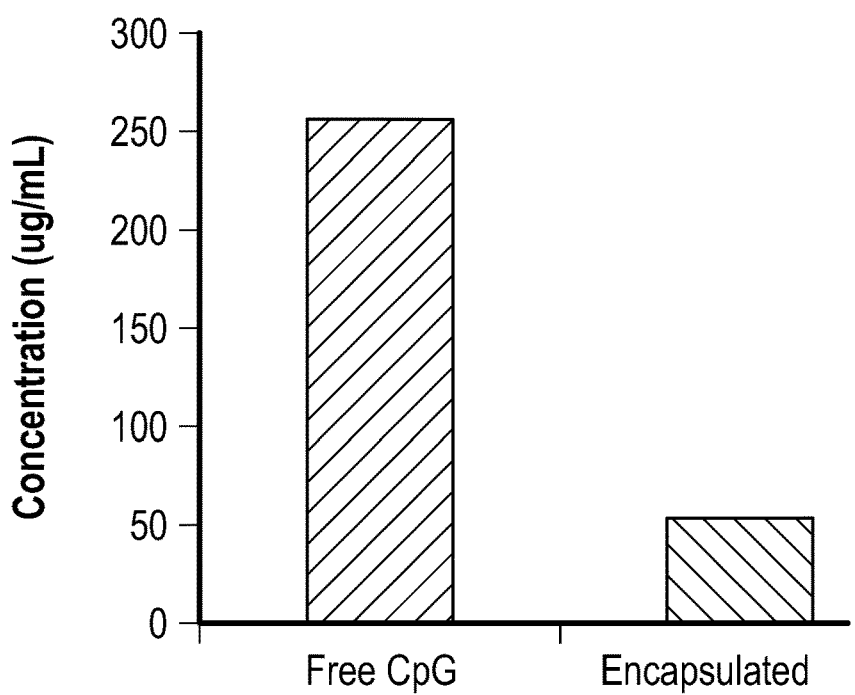

FIG. 5B depicts a bar graph showing the total concentration of free CpG and encapsulated CpG in a solution of CpG-PBNPs.

Figure 6:
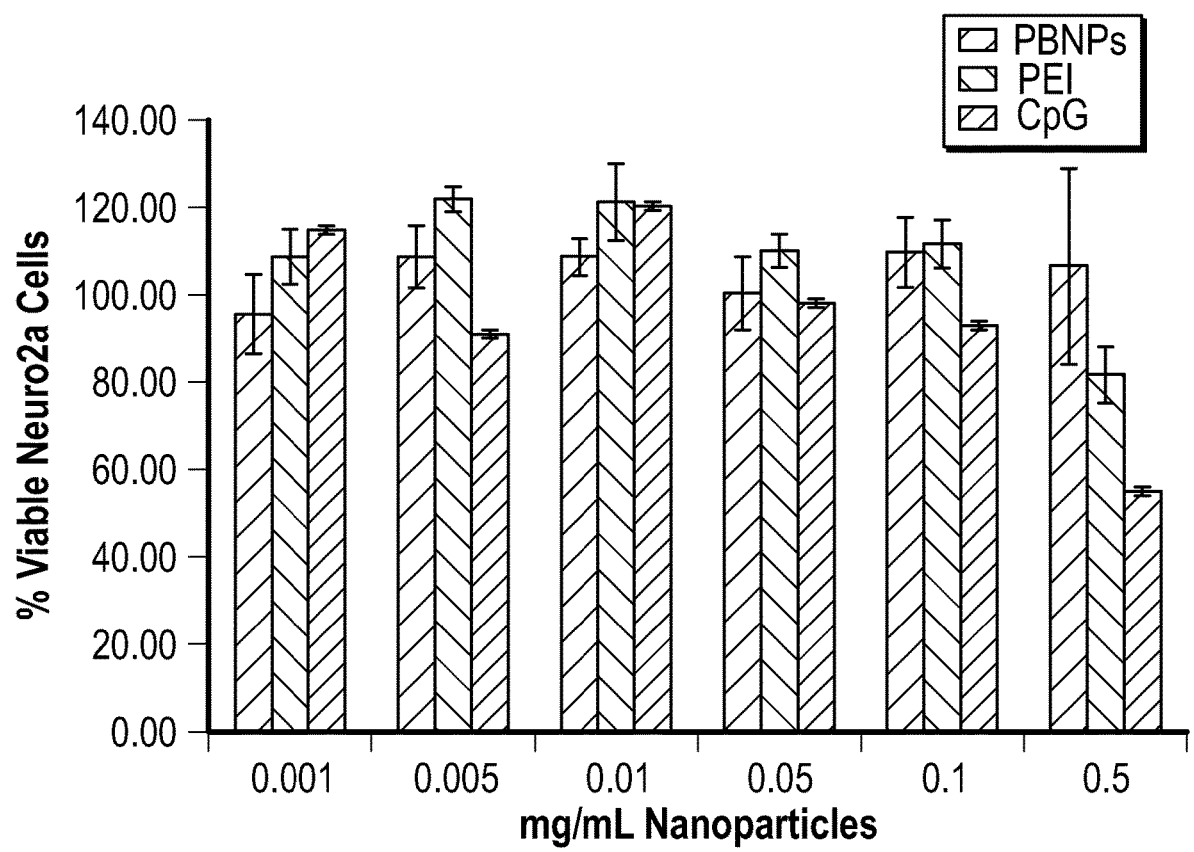

FIG. 6 depicts a bar graph showing the in vitro cytotoxicity of uncoated PBNPs, PEI-PBNPs and CpG-PBNPs in the murine neuroblastoma cell line Neuro2a.

Figure 7A:
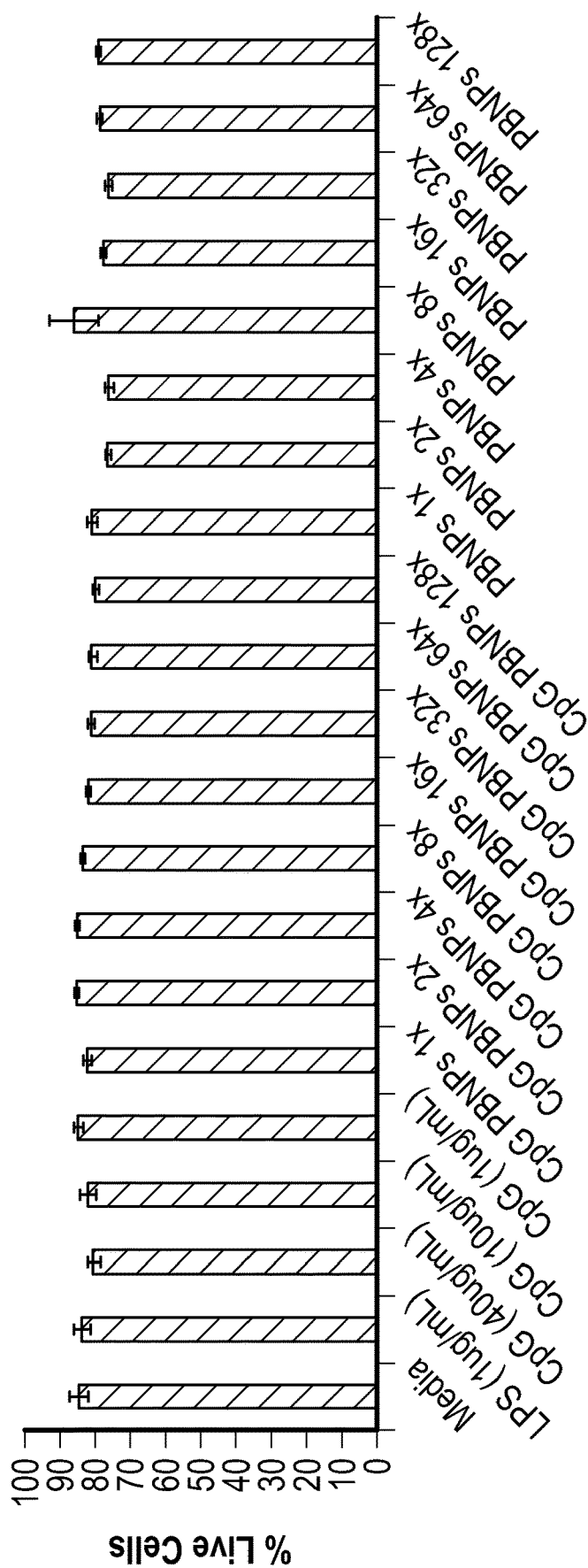

FIG. 7A depicts a bar graph showing the percentage of live DC cells following a 24-hour incubation with either with medium, lipopolysaccharide (LPS, 1 μg/mL), free CpG (40, 10 and 1 μg/mL), uncoated-PBNPs (1 mg/mL and 2×, 4×, 8×, 16×, 32×, 64×, and 128× dilutions thereof), and CpG-PBNPs (1 mg/mL PBNPs coated with 40 μg/mL CpG and 2×, 4×, 8×, 16×, 32×, 64×, and 128× dilutions thereof) as identified by a CD11c+ marker measured by flow cytometry.

Figure 7B:
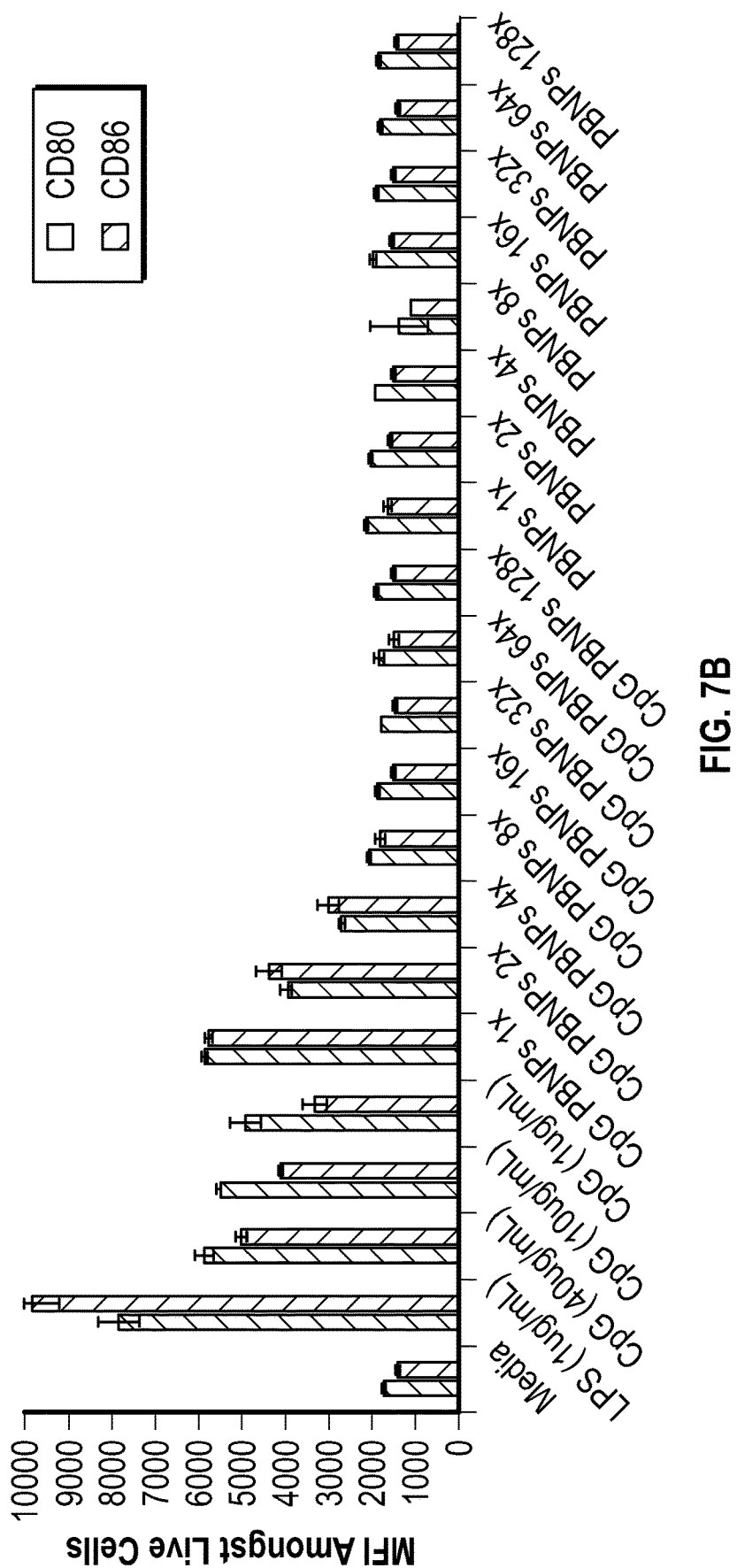

FIG. 7B depicts a bar graph showing the percentage of the mean fluorescence intensity (MFI) of CD80+ and CD86+ amongst live CD11c+ positive DC cells following a 24-hour incubation with either with medium, lipopolysaccharide (LPS, 1 μg/mL), free CpG (40, 10 and 1 μg/mL), uncoated-PBNPs (1 mg/mL and 2×, 4×, 8×, 16×, 32×, 64×, and 128× dilutions thereof), and CpG-PBNPs (1 mg/mL PBNPs coated with 40 μg/mL CpG and 2×, 4×, 8×, 16×, 32×, 64×, and 128× dilutions thereof) as measured by flow cytometry.

Figure 7C:
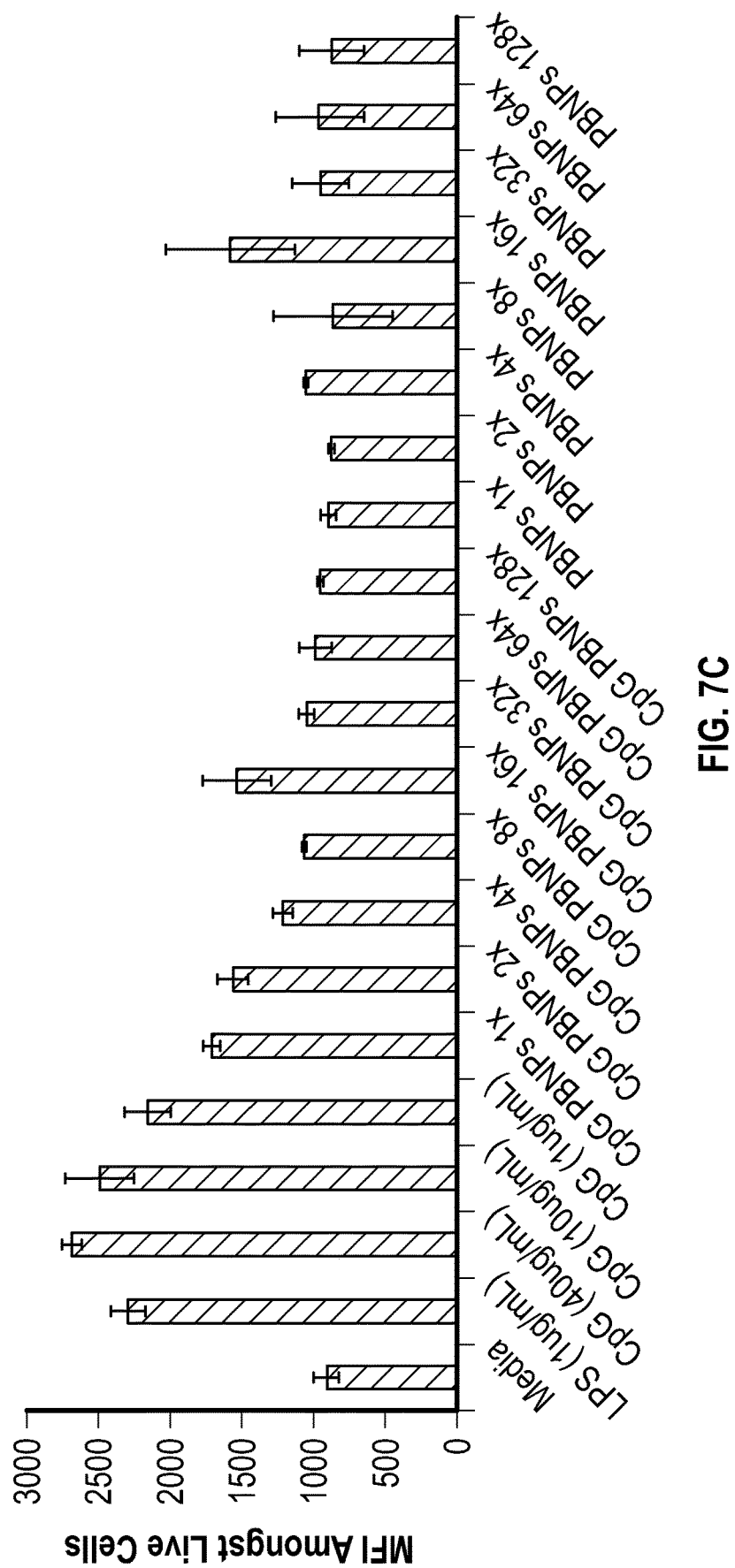

FIG. 7C depicts a bar graph showing the percentage of the mean fluorescence intensity (MFI) of CD40+ amongst live CD11c+ positive DC cells following a 24-hour incubation with either with medium, lipopolysaccharide (LPS, 1 μg/mL), free CpG (40, 10 and 1 μg/mL), uncoated-PBNPs (1 mg/mL and 2×, 4×, 8×, 16×, 32×, 64×, and 128× dilutions thereof), and CpG-PBNPs (1 mg/mL PBNPs coated with 40 μg/mL CpG and 2×, 4×, 8×, 16×, 32×, 64×, and 128× dilutions thereof) as measured by flow cytometry.

Figure 8:
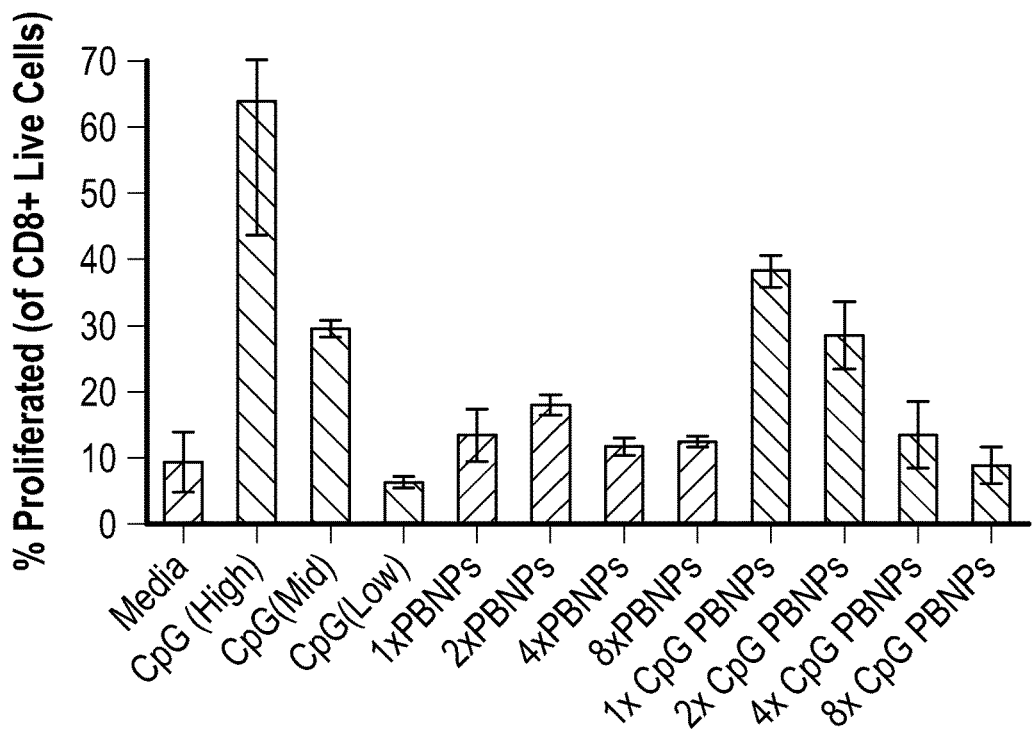

FIG. 8 depicts a bar graph showing the percentage of proliferated T cell in a DC-T cell co-culture following a 24-hour incubation with either with medium free CpG (40 μg/mL (high), 10 μg/mL (mild) and 1 μg/mL (low)), uncoated-PBNPs (1 mg/mL (1×) and 2×, 4×, and 8× dilutions thereof), and CpG-PBNPs (1 mg/mL PBNPs coated with 40 μg/mL CpG (1×) and 2×, 4×, and 8× dilutions thereof) as determined by the amount of CD8+ measured by flow cytometry.

Figure 9A:
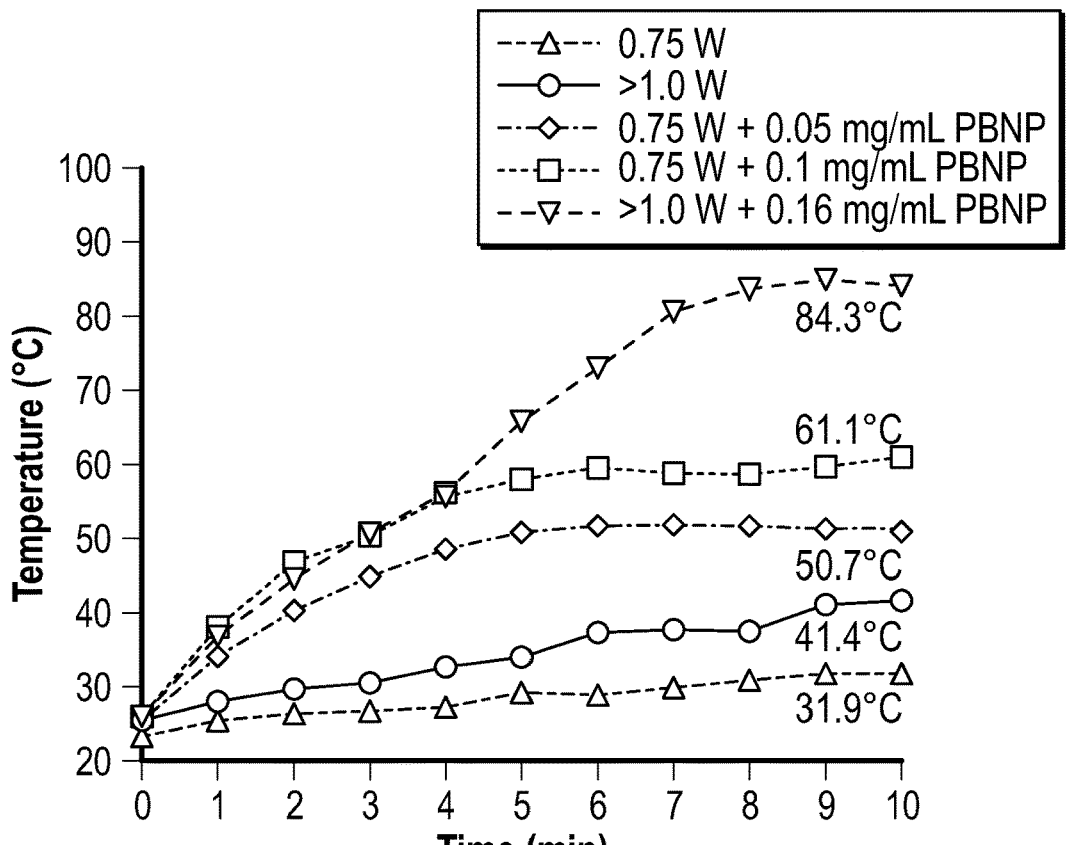

FIG. 9A depicts a graph showing the temperature—time profiles of samples containing ten million Neuro2a cells treated with 0.75 W laser, >1 W laser, 0.75 W laser+0.05 mg/mL uncoated-PBNP, 0.75 W laser+0.1 mg/mL uncoated-PBNP, or >1 W laser+0.16 mg/mL uncoated-PBNP.

Figure 9B:
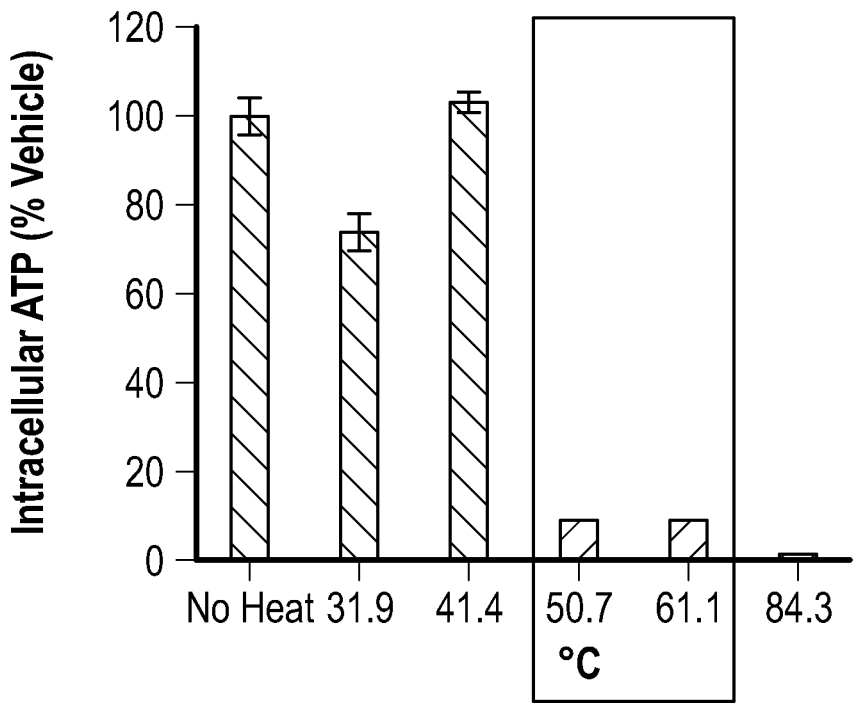

FIG. 9B depicts a bar graph showing the amount of intracellular ATP (as a % of the vehicle-treated group) in Neuro2a cells treated with 0.75 W laser, >1 W laser, 0.75 W laser+0.05 mg/mL uncoated-PBNP, 0.75 W laser+0.1 mg/mL uncoated-PBNP, or >1 W laser+0.16 mg/mL uncoated-PBNP where boxed area shows the conditions and intracellular ATP levels under which all three consensus guidelines for immunogenic cell death (ATP release, HMGB1 release, and calreticulin expression) are satisfied.

Figure 9C:
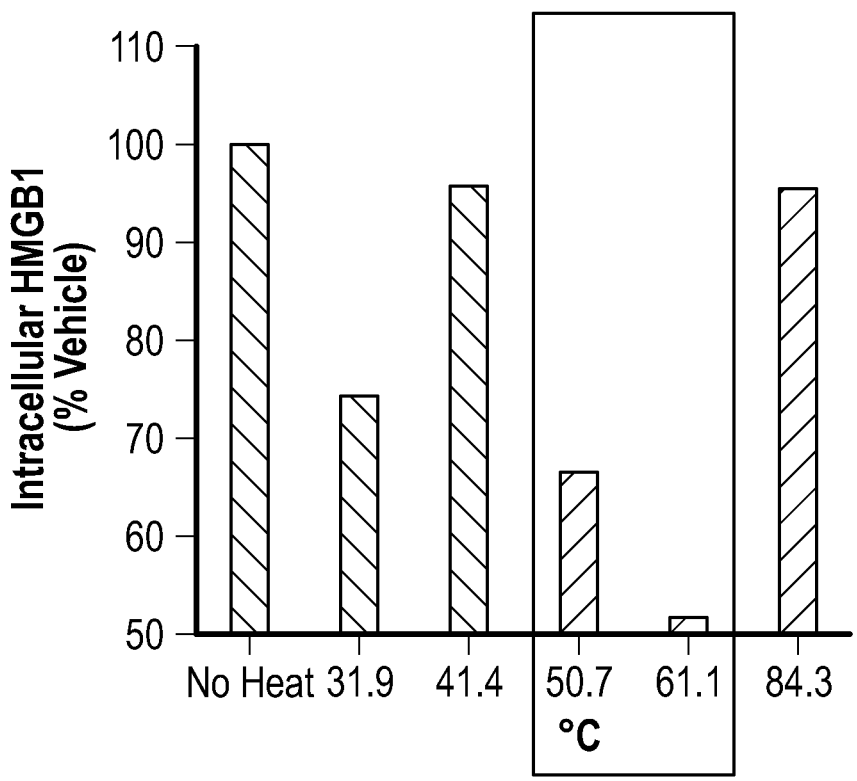

FIG. 9C depicts a bar graph showing the amount of intracellular HMGB1 (as a % of the vehicle-treated group) in Neuro2a cells treated with 0.75 W laser, >1 W laser, 0.75 W laser+0.05 mg/mL uncoated-PBNP, 0.75 W laser+0.1 mg/mL uncoated-PBNP, or >1 W laser+0.16 mg/mL uncoated-PBNP where boxed area shows the conditions and intracellular HMGB1 levels under which all three consensus guidelines for immunogenic cell death (ATP release, HMGB1 release, and calreticulin expression) are satisfied.

Figure 9D:
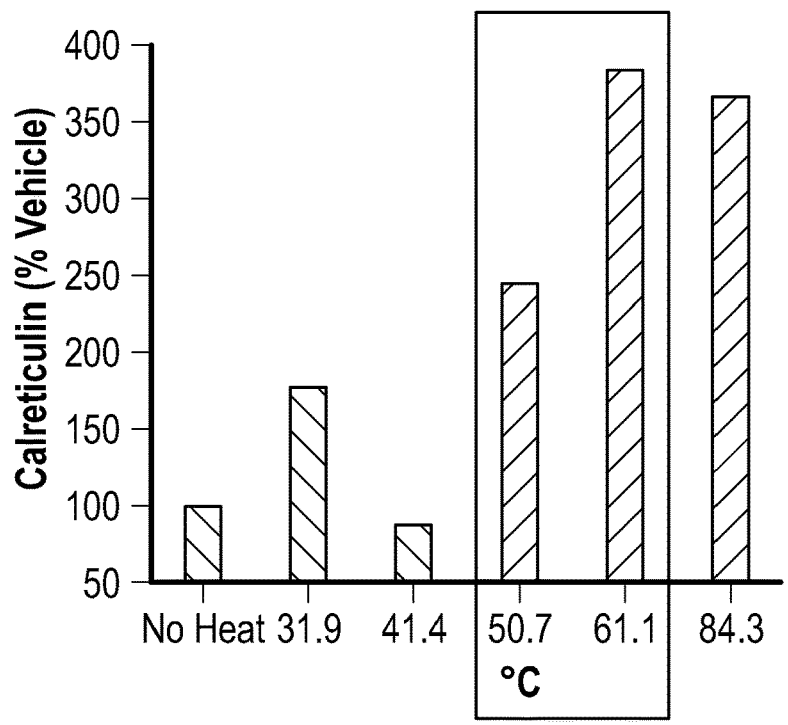

FIG. 9D depicts a bar graph showing the amount of surface calreticulin expression (as a % of the vehicle-treated group) in Neuro2a cells treated with 0.75 W laser, >1 W laser, 0.75 W laser+0.05 mg/mL uncoated-PBNP, 0.75 W laser+0.1 mg/mL uncoated-PBNP, or >1 W laser+0.16 mg/mL uncoated-PBNP where boxed area shows the conditions and cell surface calreticulin levels under which all three consensus guidelines for immunogenic cell death (ATP release, HMGB1 release, and calreticulin expression) are satisfied.

Figure 10A:
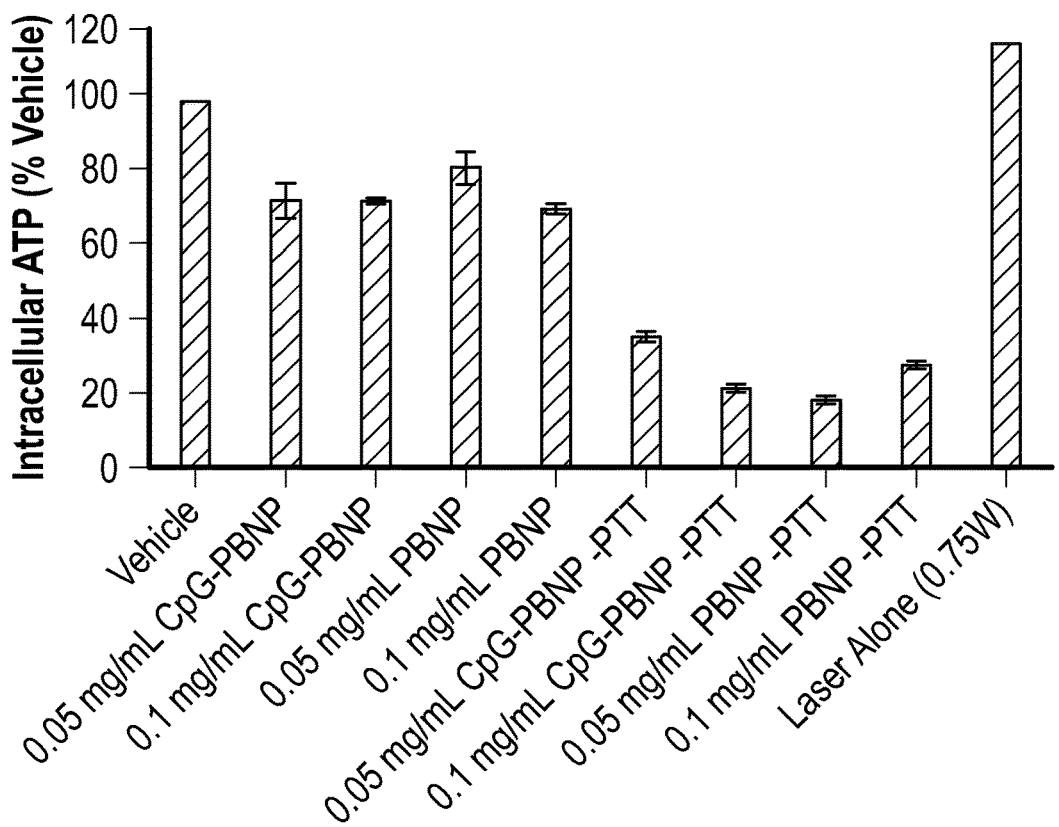

FIG. 10A depicts a bar graph showing the amount of intracellular ATP (as a % of the vehicle-treated group) in Neuro2a cells treated with medium (vehicle), 0.05 mg/mL CpG-PBNP, 0.1 mg/mL CpG-PBNP, 0.05 mg/mL uncoated-PBNP, 0.1 mg/mL uncoated-PBNP, 0.75 W laser+0.05 mg/mL CpG-PBNP (CpG-PBNP-PTT), 0.75 W laser+0.1 mg/mL CpG-PBNP (CpG-PBNP-PTT), 0.75 W laser+0.05 mg/mL uncoated-PBNP (PBNP-PTT), 0.75 W laser+0.1 mg/mL uncoated-PBNP (PBNP-PTT), or 0.75 W laser alone.

Figure 10B:
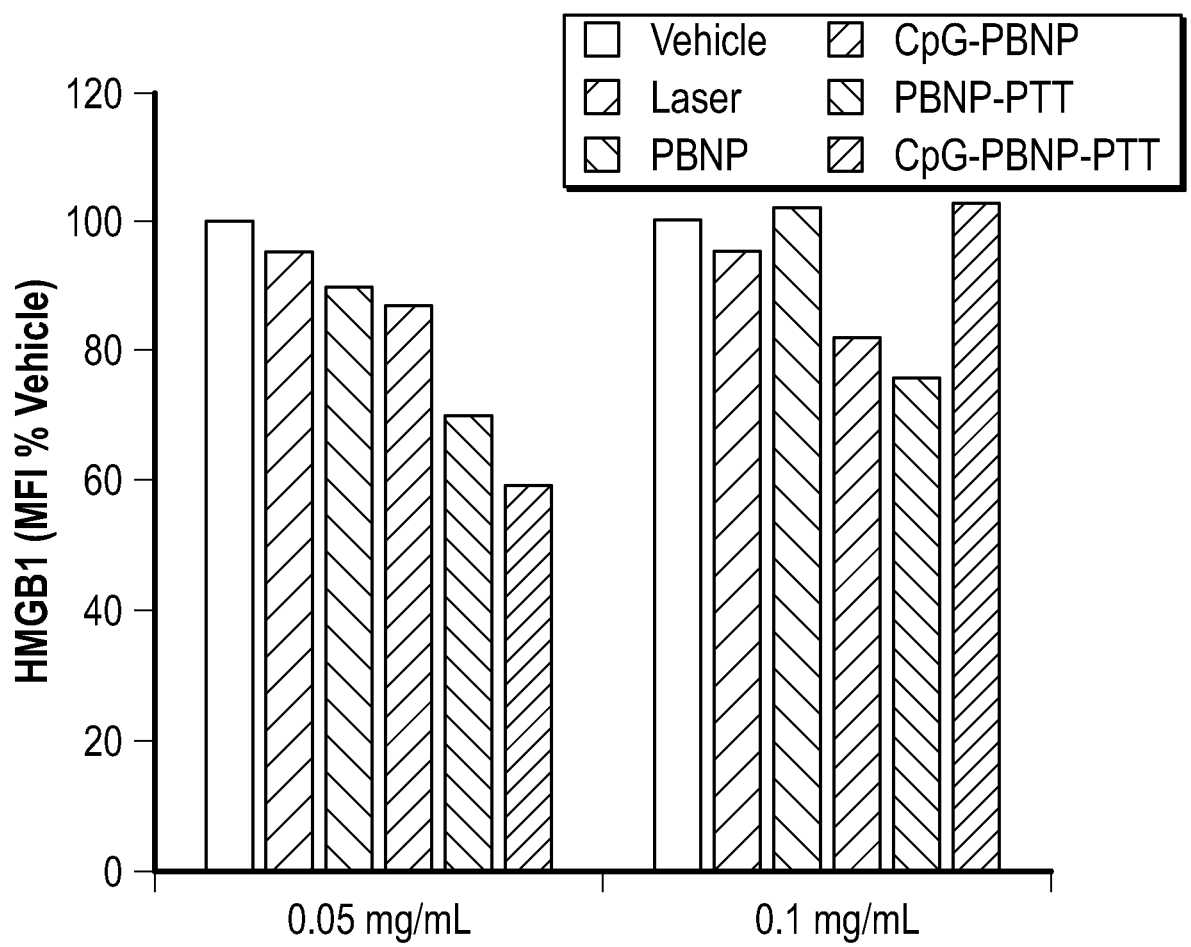

FIG. 10B depicts a bar graph showing the amount of intracellular HMGB1 (as a % of the vehicle-treated group) in Neuro2a cells treated with medium (vehicle), 0.05 mg/mL CpG-PBNP, 0.1 mg/mL CpG-PBNP, 0.05 mg/mL uncoated-PBNP, 0.1 mg/mL uncoated-PBNP, 0.75 W laser+0.05 mg/mL CpG-PBNP (CpG-PBNP-PTT), 0.75 W laser+0.1 mg/mL CpG-PBNP (CpG-PBNP-PTT), 0.75 W laser+0.05 mg/mL uncoated-PBNP (PBNP-PTT), 0.75 W laser+0.1 mg/mL uncoated-PBNP (PBNP-PTT), or 0.75 W laser alone.

Figure 10C:
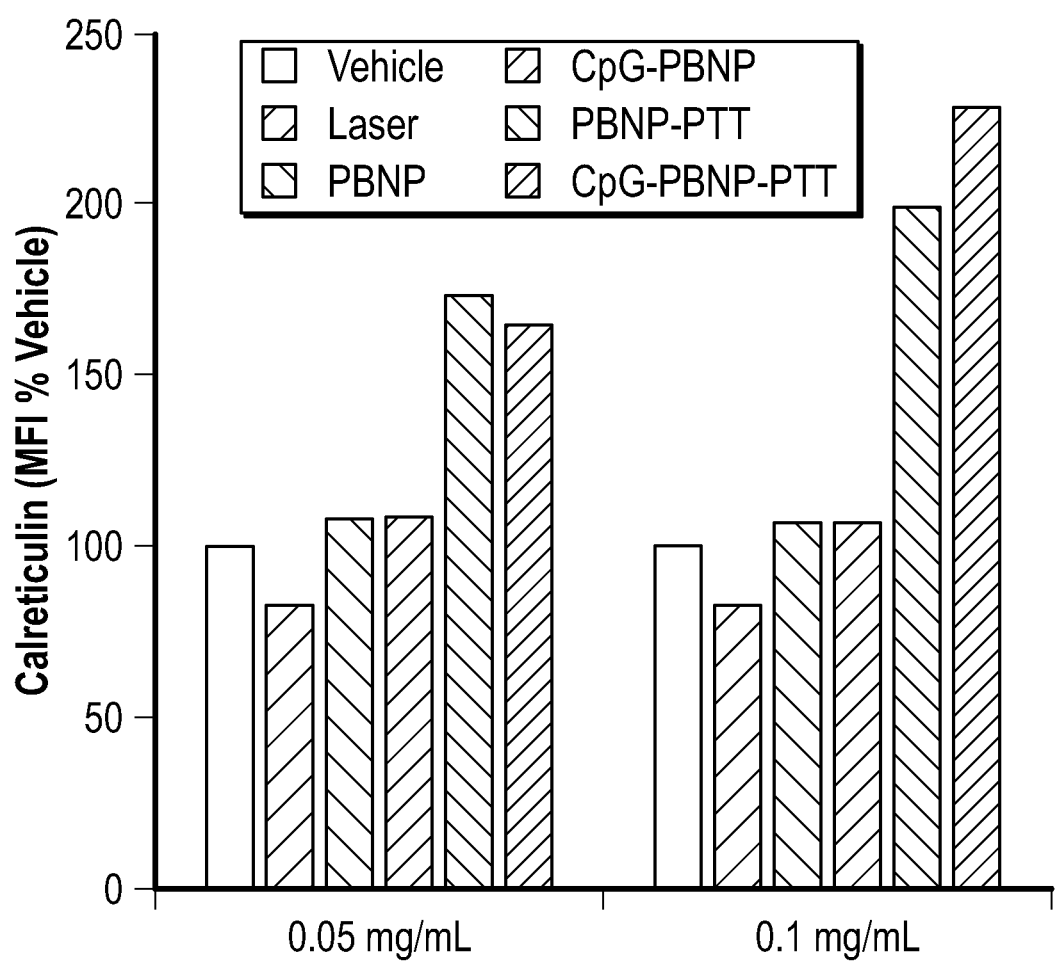

FIG. 10C depicts a bar graph showing the amount of surface calreticulin expression (as a % of the vehicle-treated group) in Neuro2a cells treated with medium (vehicle), 0.05 mg/mL CpG-PBNP, 0.1 mg/mL CpG-PBNP, 0.05 mg/mL uncoated-PBNP, 0.1 mg/mL uncoated-PBNP, 0.75 W laser+ 0.05 mg/mL CpG-PBNP (CpG-PBNP-PTT), 0.75 W laser+ 0.1 mg/mL CpG-PBNP (CpG-PBNP-PTT), 0.75 W laser+ 0.05 mg/mL uncoated-PBNP (PBNP-PTT), 0.75 W laser+ 0.1 mg/mL uncoated-PBNP (PBNP-PTT), or 0.75 W laser alone.

Figure 10D:
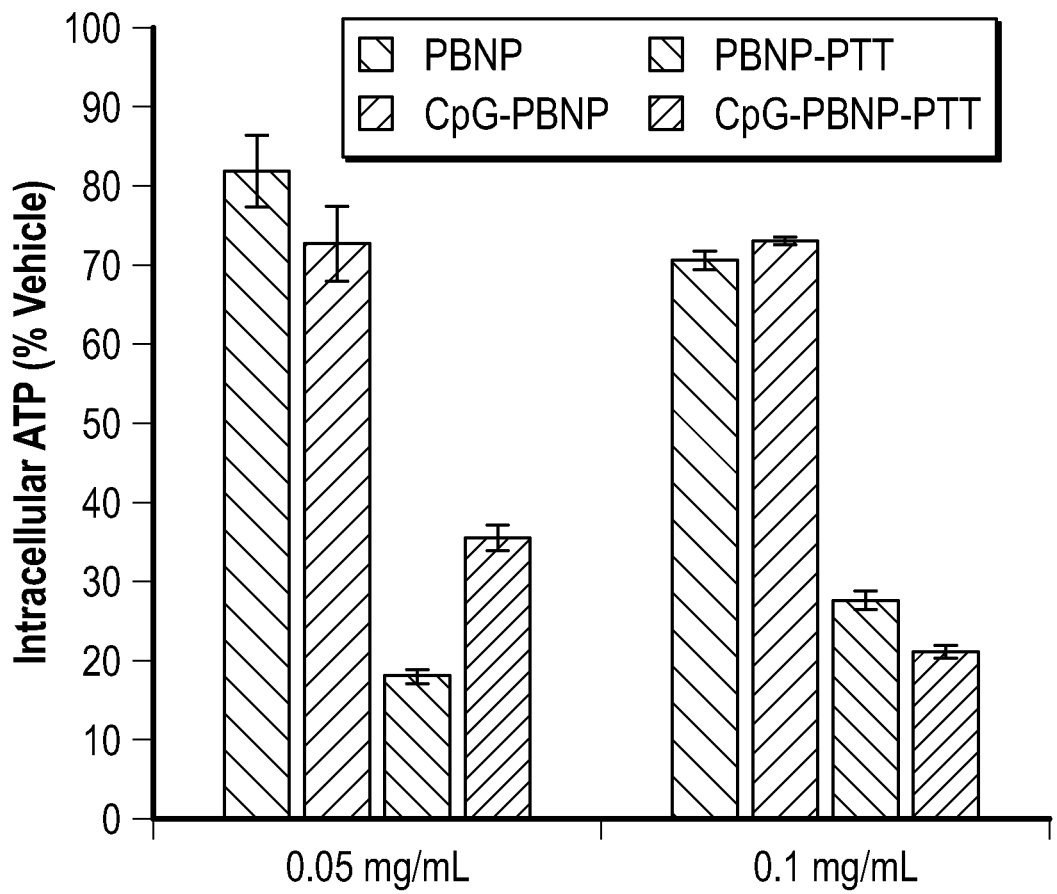

FIG. 10D depicts a bar graph showing the amount of intracellular ATP (as a % of the vehicle-treated group) in Neuro2a cells treated with medium (vehicle), 0.05 mg/mL CpG-PBNP, 0.1 mg/mL CpG-PBNP, 0.05 mg/mL uncoated-PBNP, 0.1 mg/mL uncoated-PBNP, 0.75 W laser+0.05 mg/mL CpG-PBNP (CpG-PBNP-PTT), 0.75 W laser+0.1 mg/mL CpG-PBNP (CpG-PBNP-PTT), 0.75 W laser+0.05 mg/mL uncoated-PBNP (PBNP-PTT), 0.75 W laser+0.1 mg/mL uncoated-PBNP (PBNP-PTT), or 0.75 W laser alone.

Figures 11A, 11B:
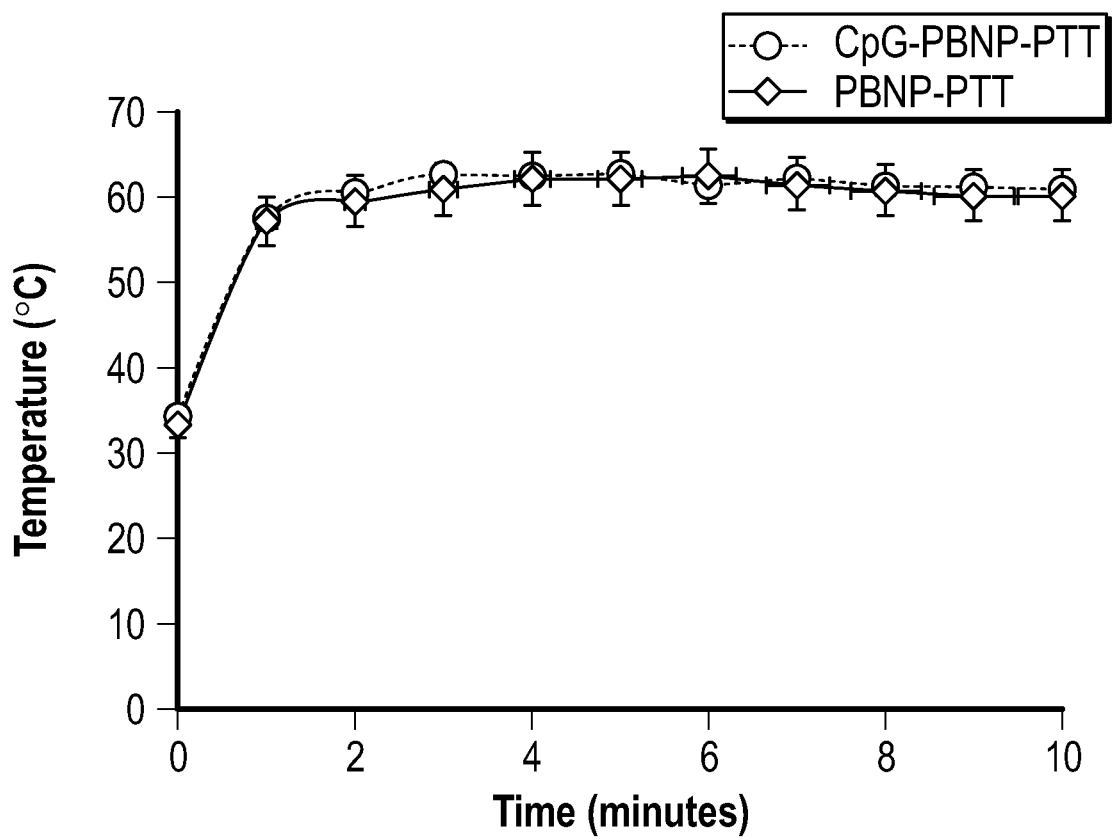

FIG. 11A is a schematic of an example of a in vivo treatment protocol.

FIG. 11B depicts a graph showing the temperature-time profiles of CpG-PBNP-PTT and uncoated-PBNP-PTT during irradiation by an 808 nm laser at 0.75 W for 10 minutes in mice bearing ~5 mm in diameter Neuro2a neuroblastoma tumors injected (i.t.) with either CpG-PBNPs or uncoated-PBNPs.

Figure 11C:
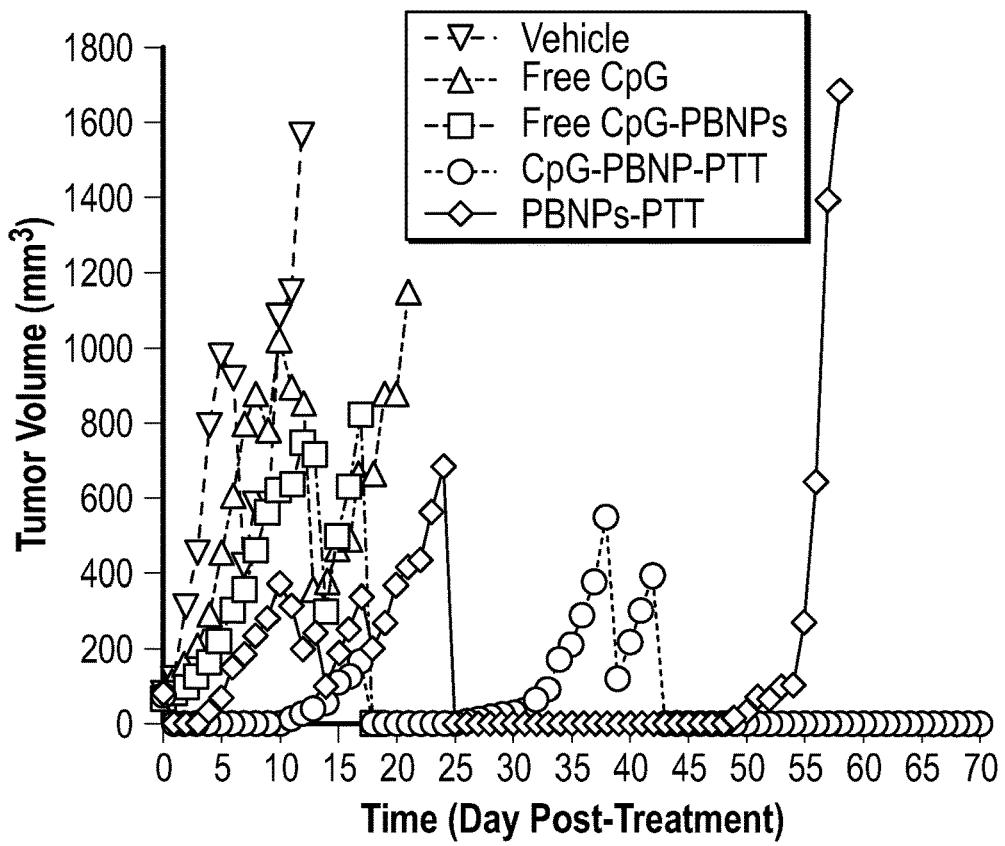

FIG. 11C depicts a graph showing the average tumor growth rates of neuroblastoma-bearing mice that were treated with CpG-PBNP-PTT, uncoated-PBNP-PTT, free CpG-PBNPs, free uncoated-PBNPs, and saline (vehicle) up to 70 day post-treatment.

Figure 11D:
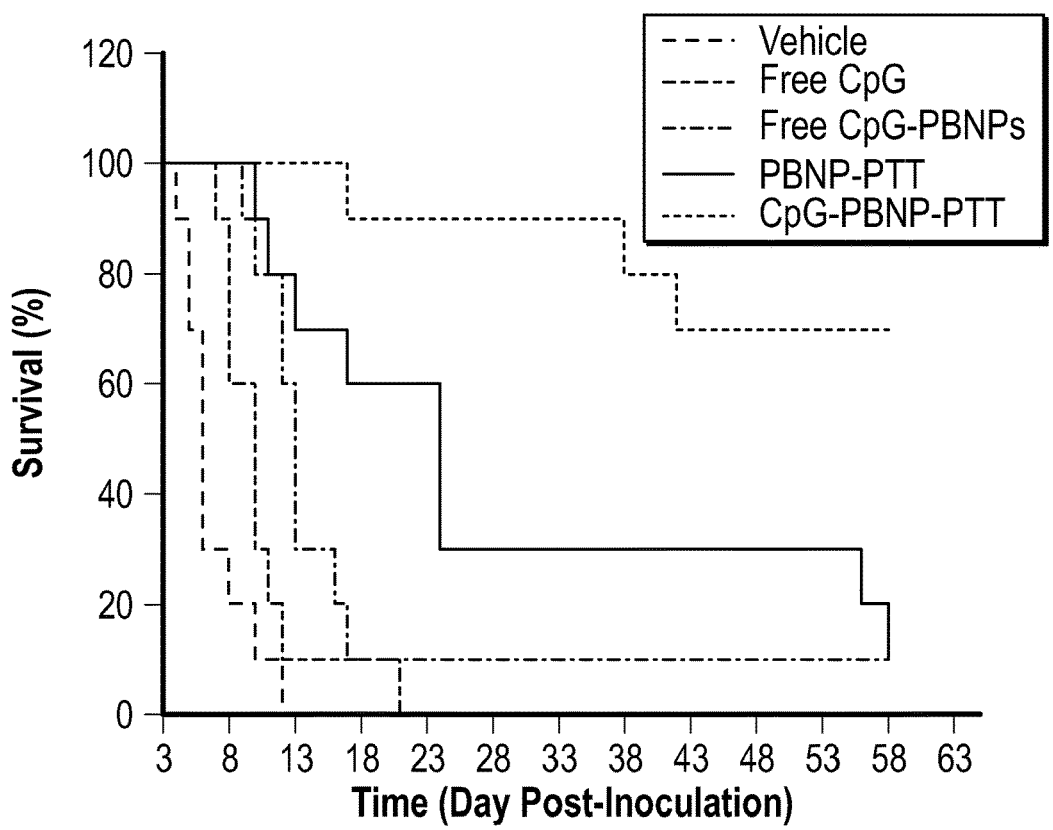

FIG. 11D depicts a graph showing the survival plots of neuroblastoma-bearing mice that were treated with CpG-PBNP-PTT, uncoated-PBNP-PTT, free CpG-PBNPs, free uncoated-PBNPs, and saline (vehicle) up to 63 day post-treatment.

Figure 11E:
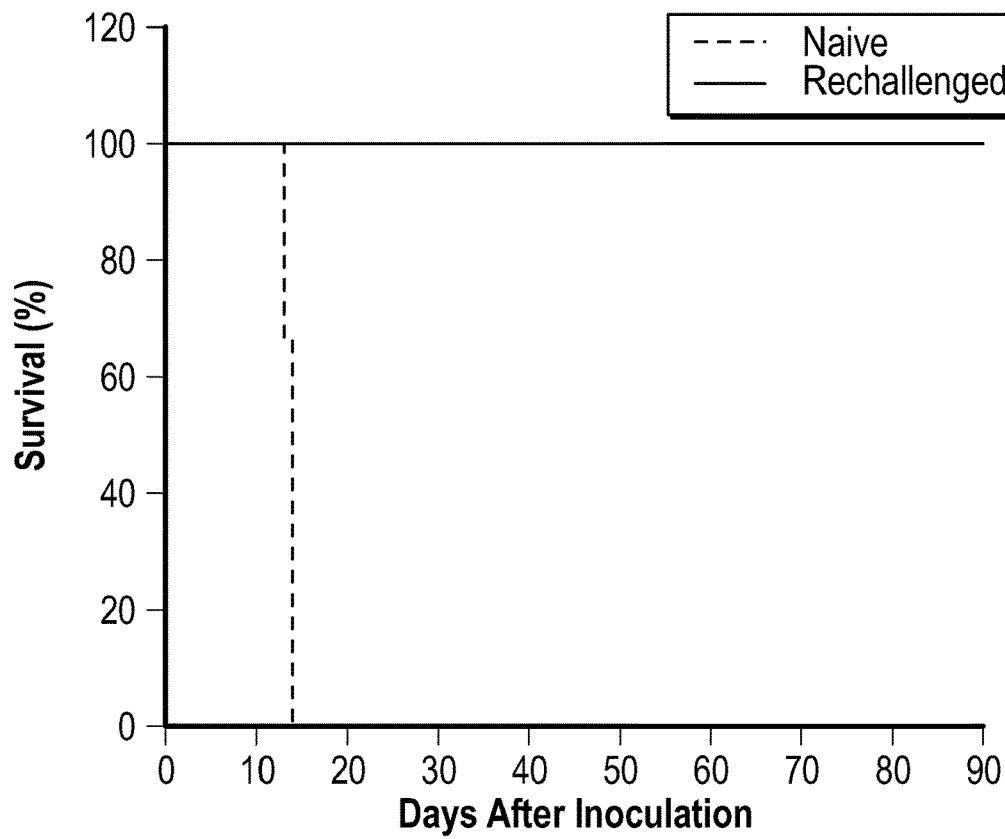

FIG. 11E depicts a graph showing CpG-PBNP-PTT-treated long-term surviving mice rechallenged with Neuro2a cells for 60 to 90 days after orginal CpG-PBNP-PTT treatment.

Figure 12A:
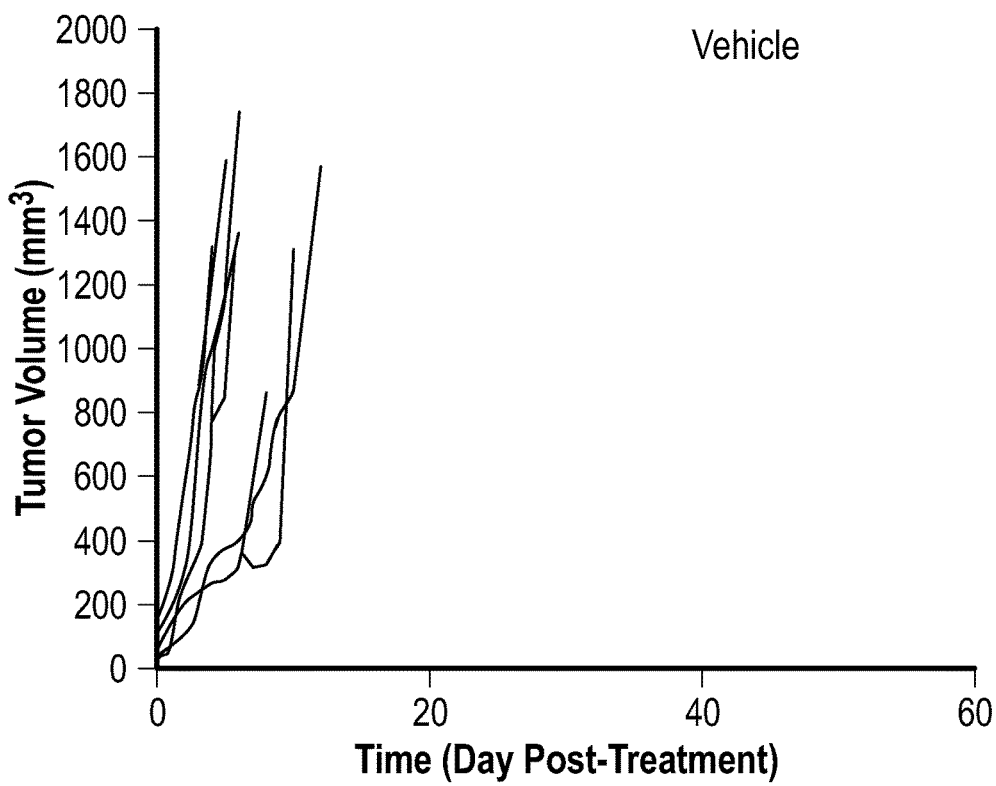

FIG. 12A depicts a graph showing the tumor growth rates of neuroblastoma-bearing mice that were treated with saline (vehicle) up to 60 days post-treatment.

Figure 12B:
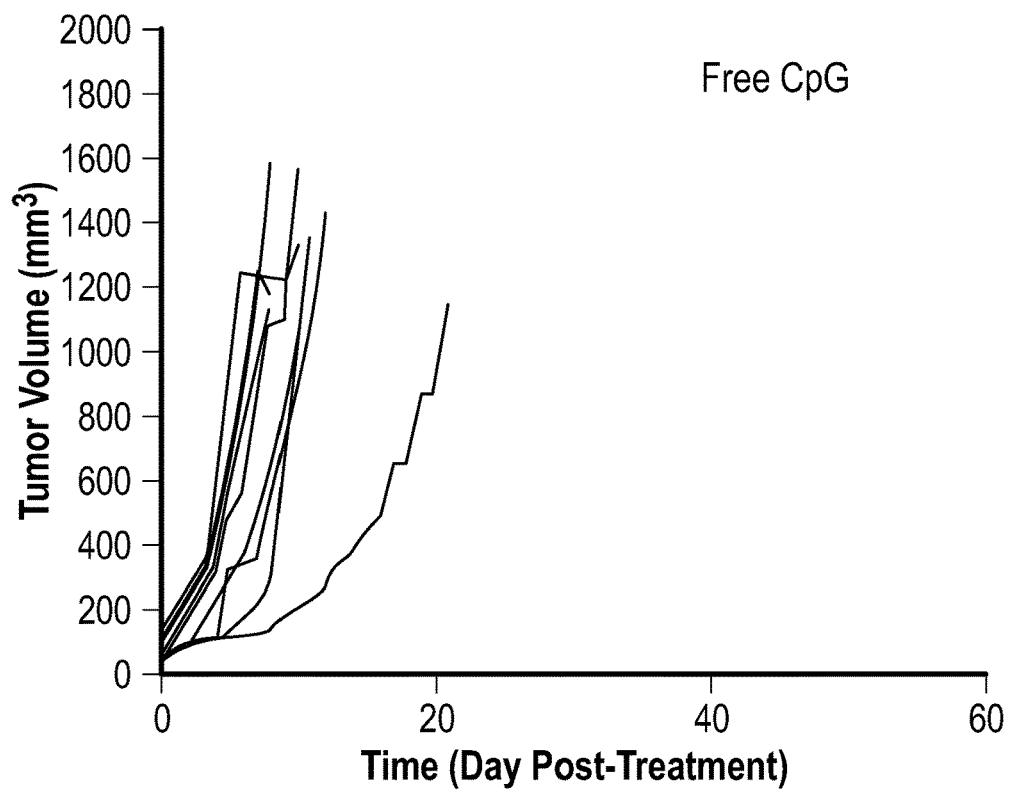

FIG. 12B depicts a graph showing the tumor growth rates of neuroblastoma-bearing mice that were treated with free CpG up to 60 days post-treatment.

Figure 12C:
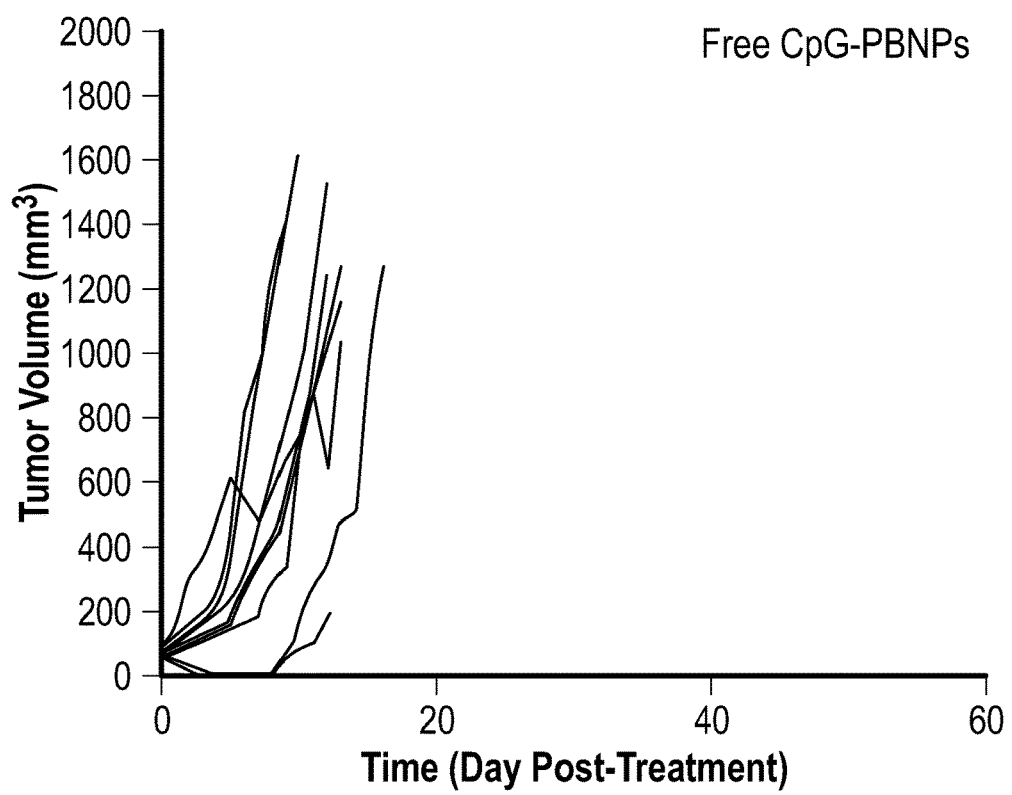

FIG. 12C depicts a graph showing the tumor growth rates of neuroblastoma-bearing mice that were treated with free CpG-PNBPs up to 60 days post-treatment.

Figure 12D:
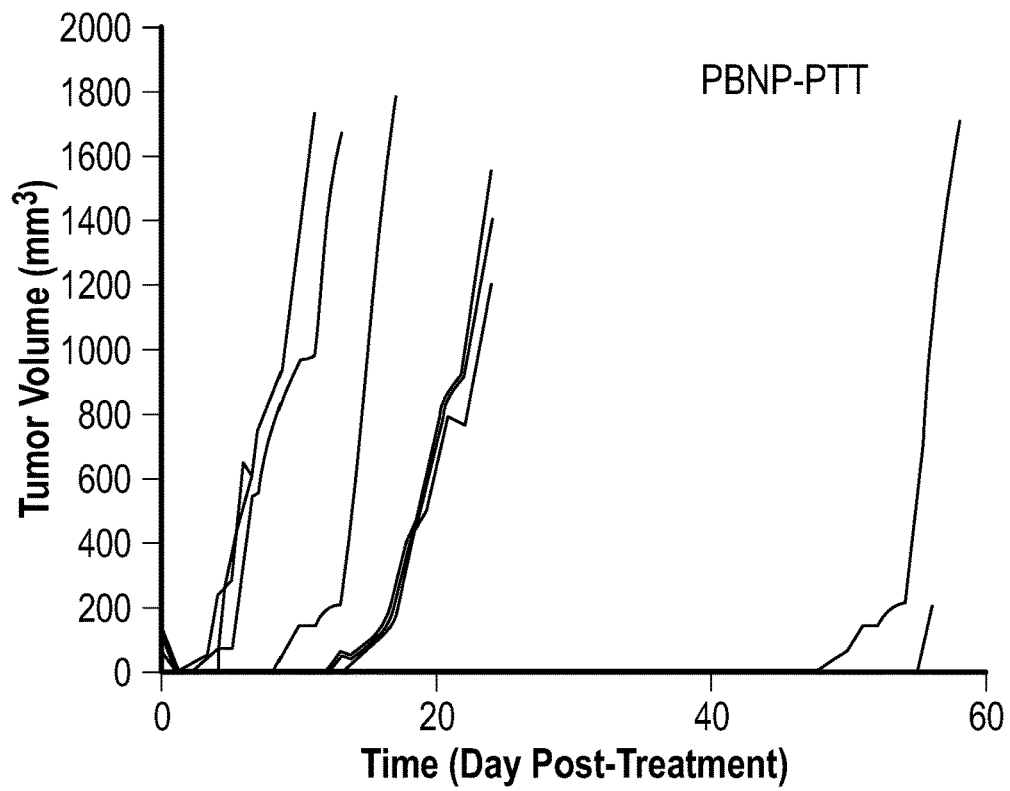

FIG. 12D depicts a graph showing the tumor growth rates of neuroblastoma-bearing mice that were treated with 0.75 W laser+0.05 mg/mL uncoated-PBNP (PBNP-PTT) up to 60 days post-treatment.

Figure 12E:
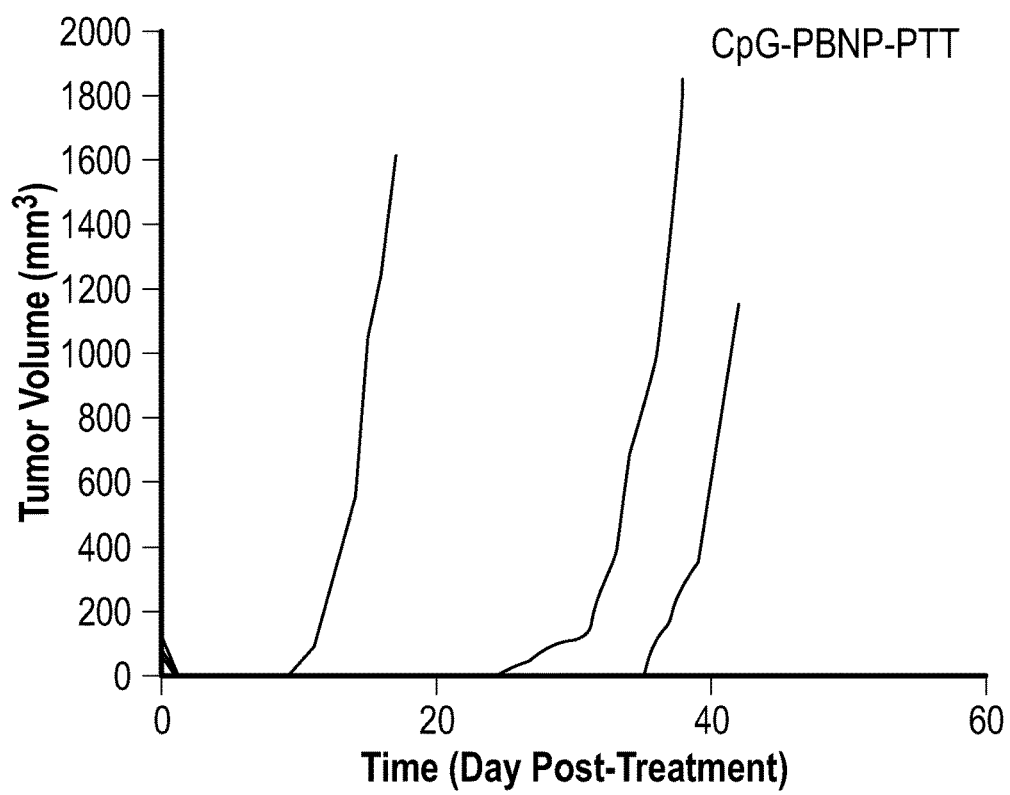

FIG. 12E depicts a graph showing the tumor growth rates of neuroblastoma-bearing mice that were treated with 0.75 W laser+0.05 mg/mL CpG-PBNP (CpG-PBNP-PTT) up to 60 days post-treatment.

Figure 13A:
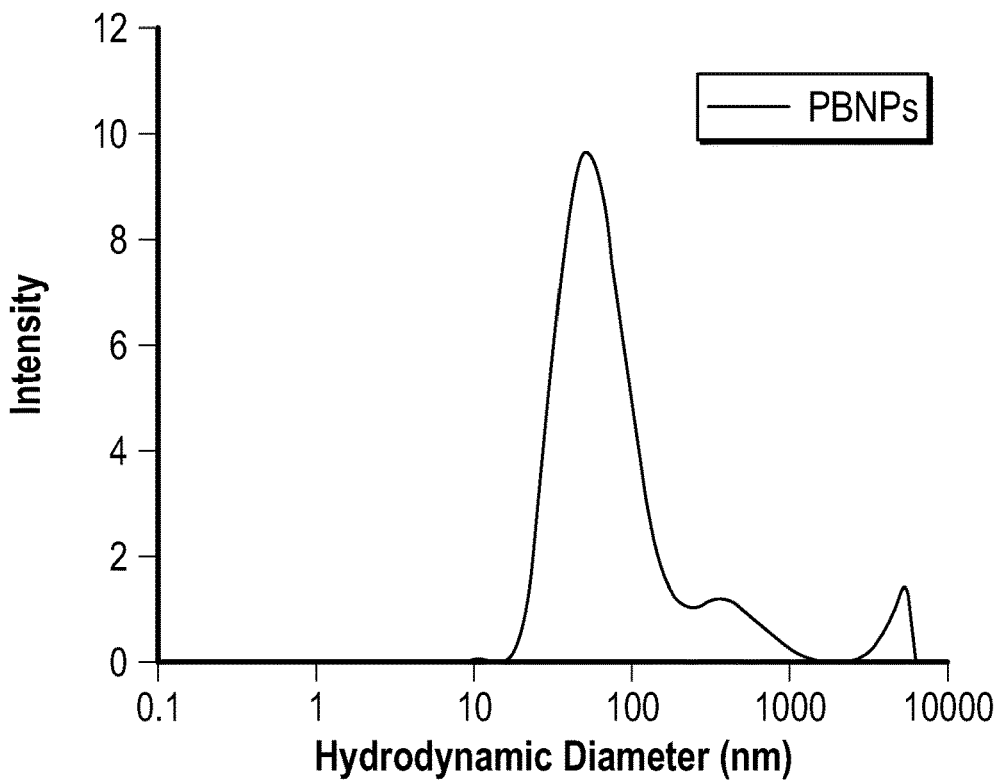

FIG. 13A depicts a graph showing the particle size distribution of uncoated PBNPs using dynamic light scattering (DLS).

Figure 13B:
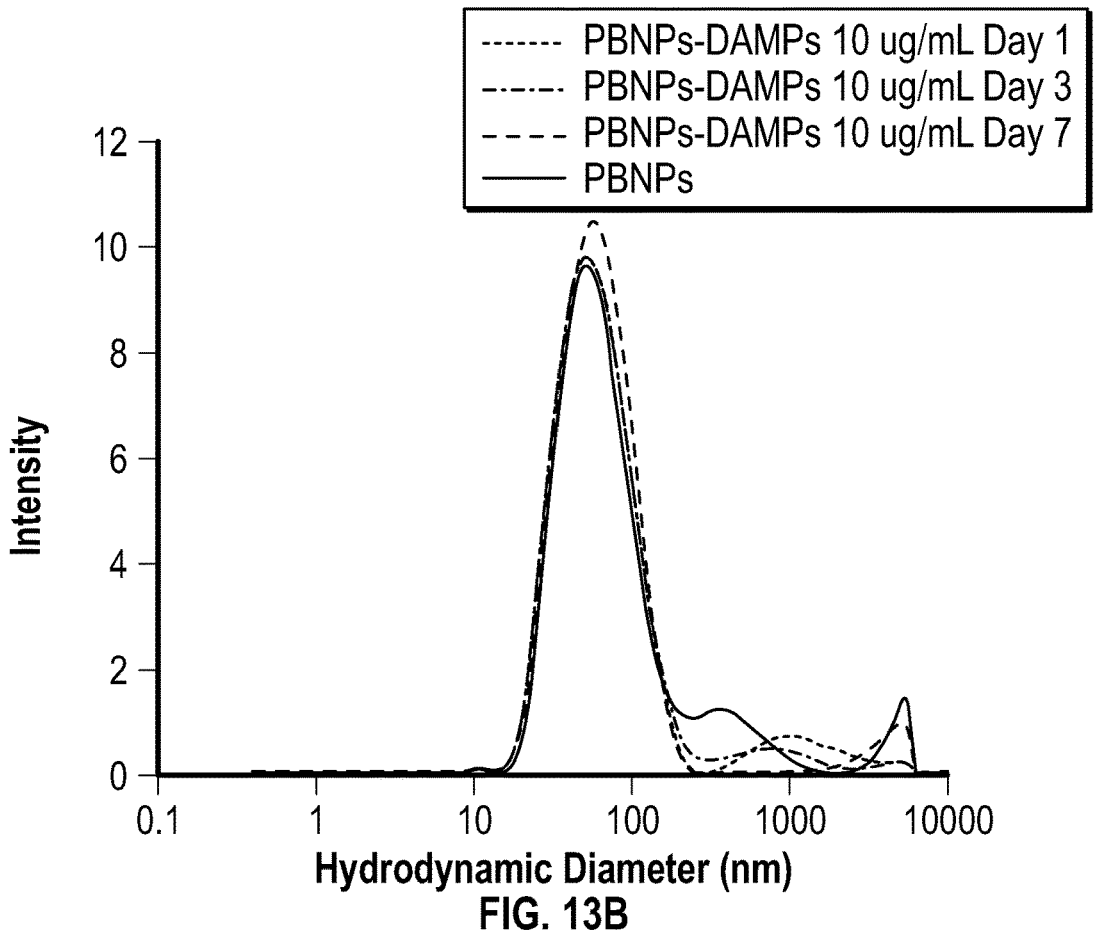

FIG. 13B depicts a graph showing the particle size distribution of DAMPs-PBNPs stored in water at day 1, 3 and 7 using temporal DLS.

Figure 14:
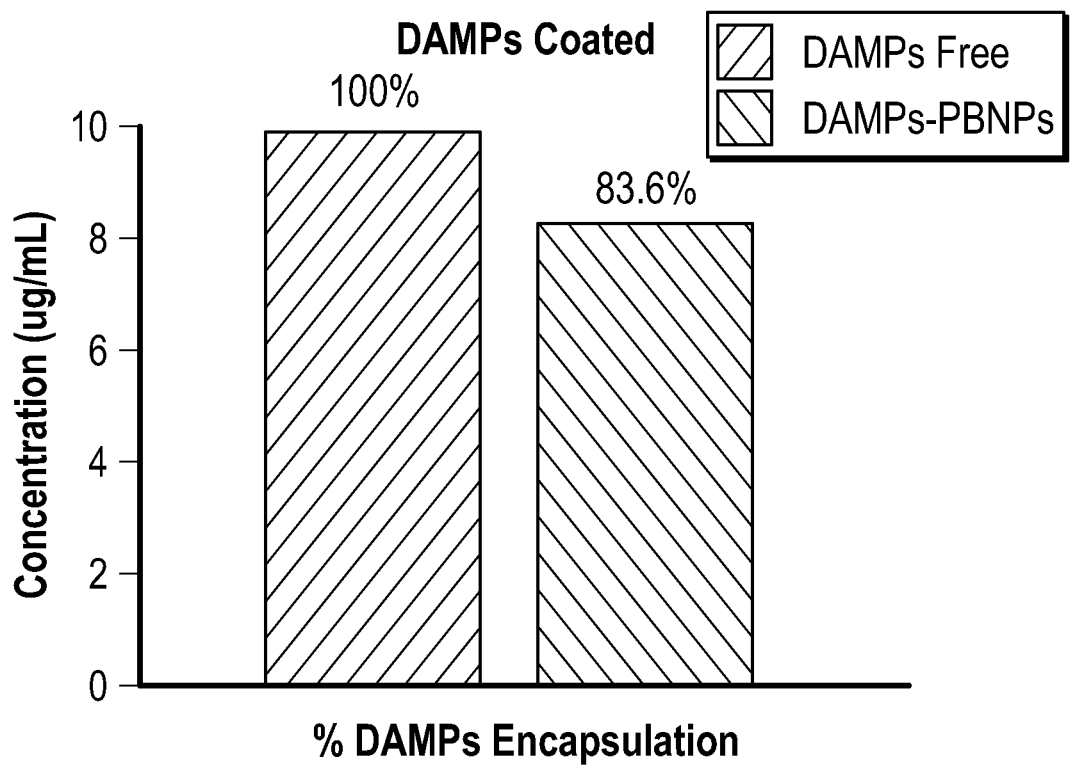

FIG. 14 depicts a bar graph showing the total concentration of free DAMPs and encapsulated DAMPs in a solution of DAMPs-PBNPs.

Figure 15:
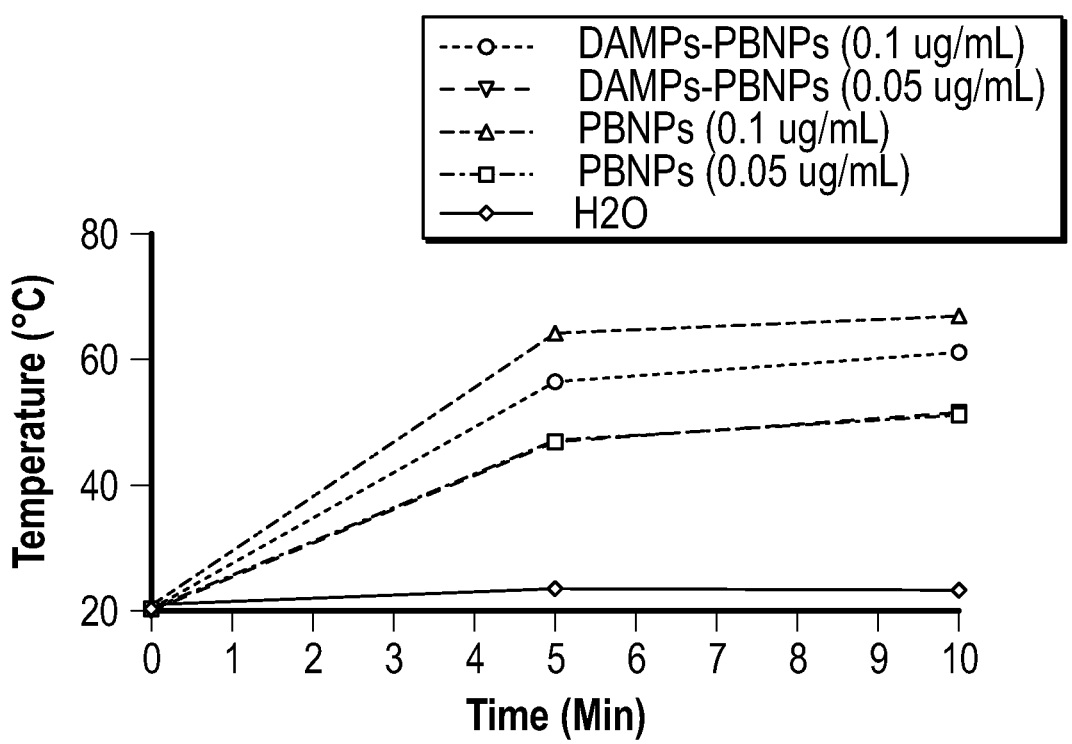

FIG. 15 depicts a graph showing the photothermal heating characteristics following photo-thermal heating of 0.05 mg/mL and 0.1 mg/mL uncoated PBNPs and 0.05 mg/mL and 0.1 mg/mL DAMPs-PBNPs irradiated by an 808 nm NIR laser for 10 minutes at 0.75 W power.

Figure 16A:
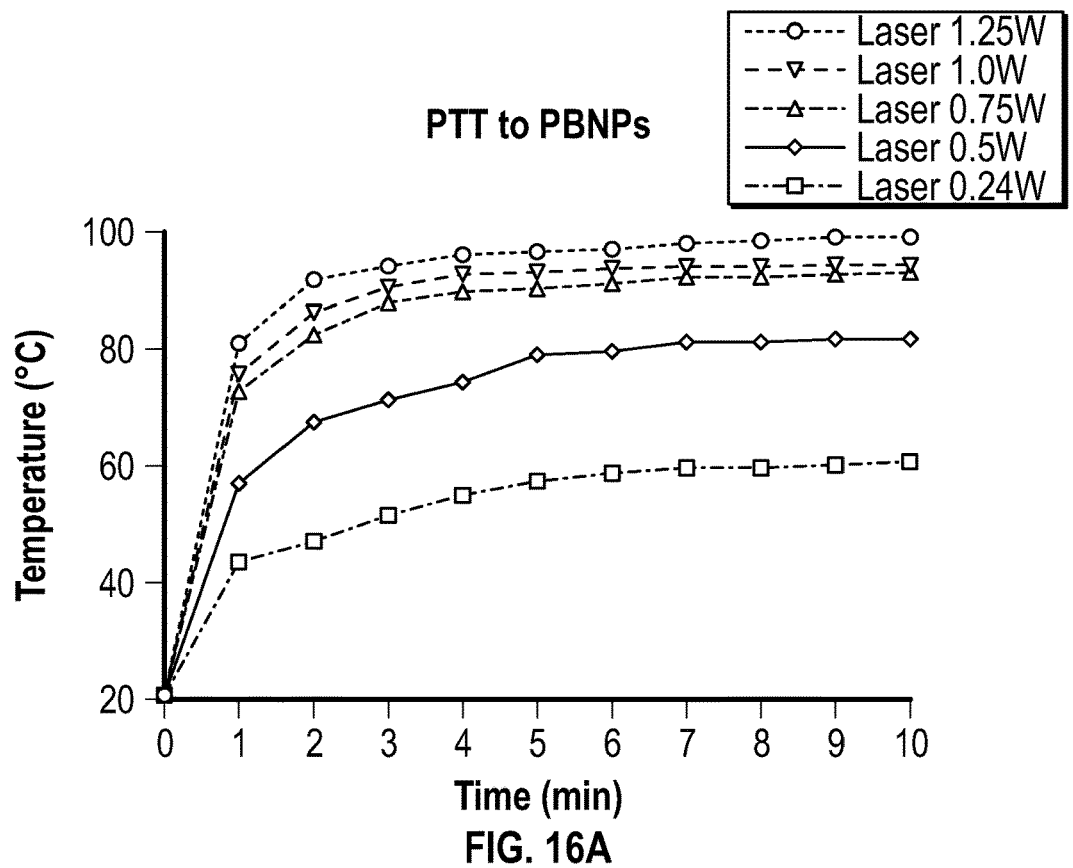

FIG. 16A depicts a graph showing the photothermal heating characteristics of 1 mg/mL uncoated PBNPs following irradiation by a NIR laser at powers of 0.24 W, 0.5 W, 0.75 W, 1.0 W, and 1.25 W for 10 minutes.

Figure 16B:
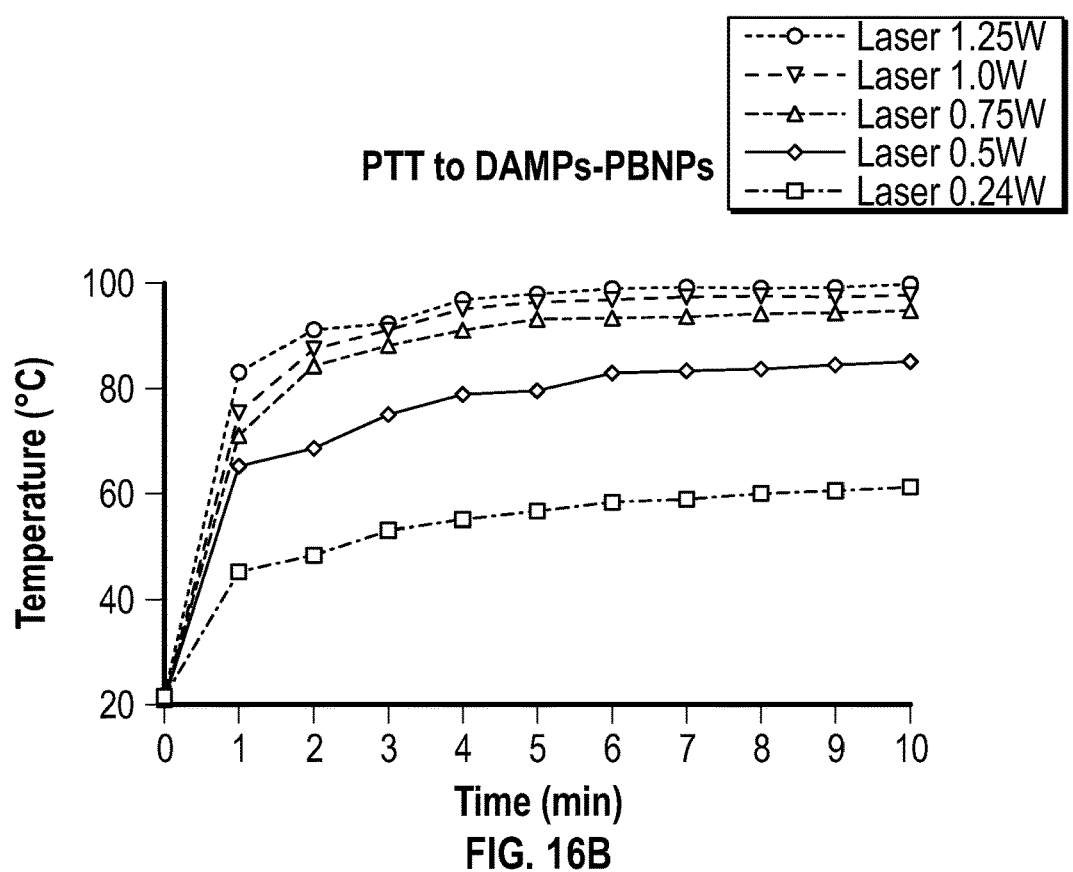

FIG. 16B depicts a graph showing the photothermal heating characteristics of 1 mg/mL DAMPs-PBNPs following irradiation by a NIR laser at powers of 0.24 W, 0.5 W, 0.75 W, 1.0 W, and 1.25 W for 10 minutes.

Figure 17:
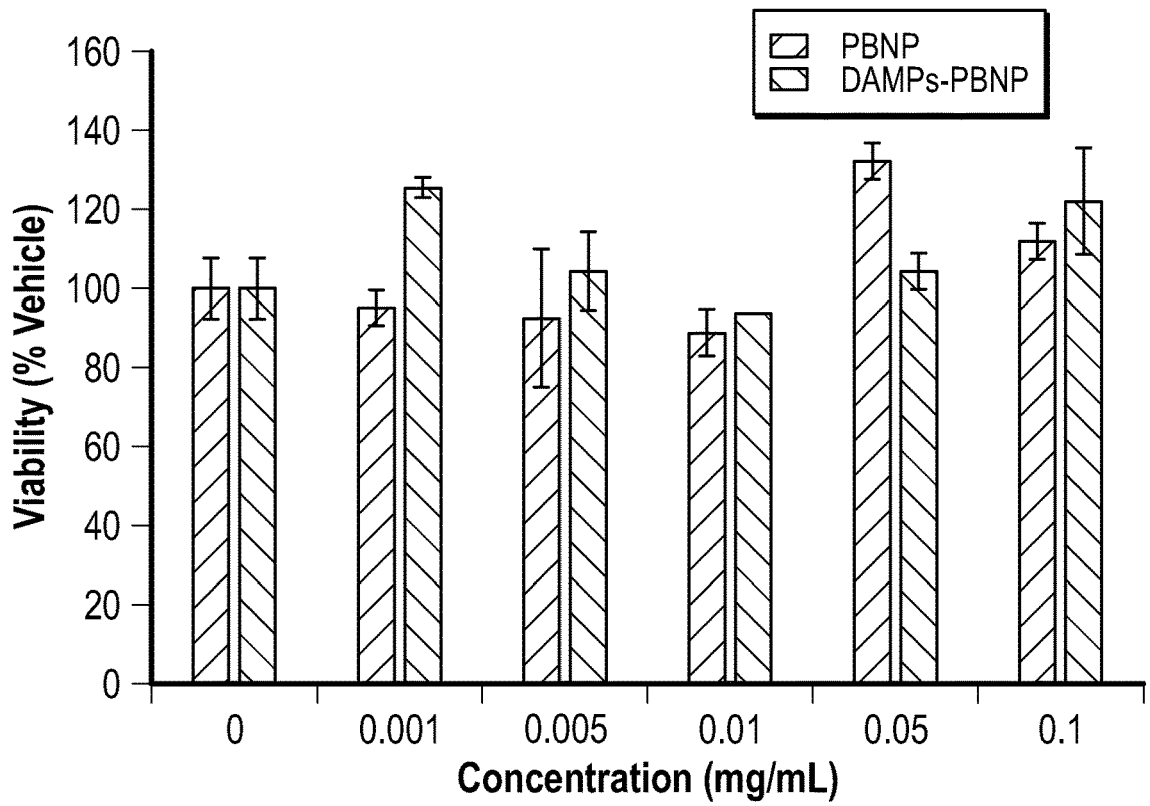

FIG. 17 depicts a bar graph showing the in vitro cytotoxicity of uncoated PBNPs and DAMPs-PBNPs in the murine neuroblastoma cell line Neuro2a.

Figure 18:
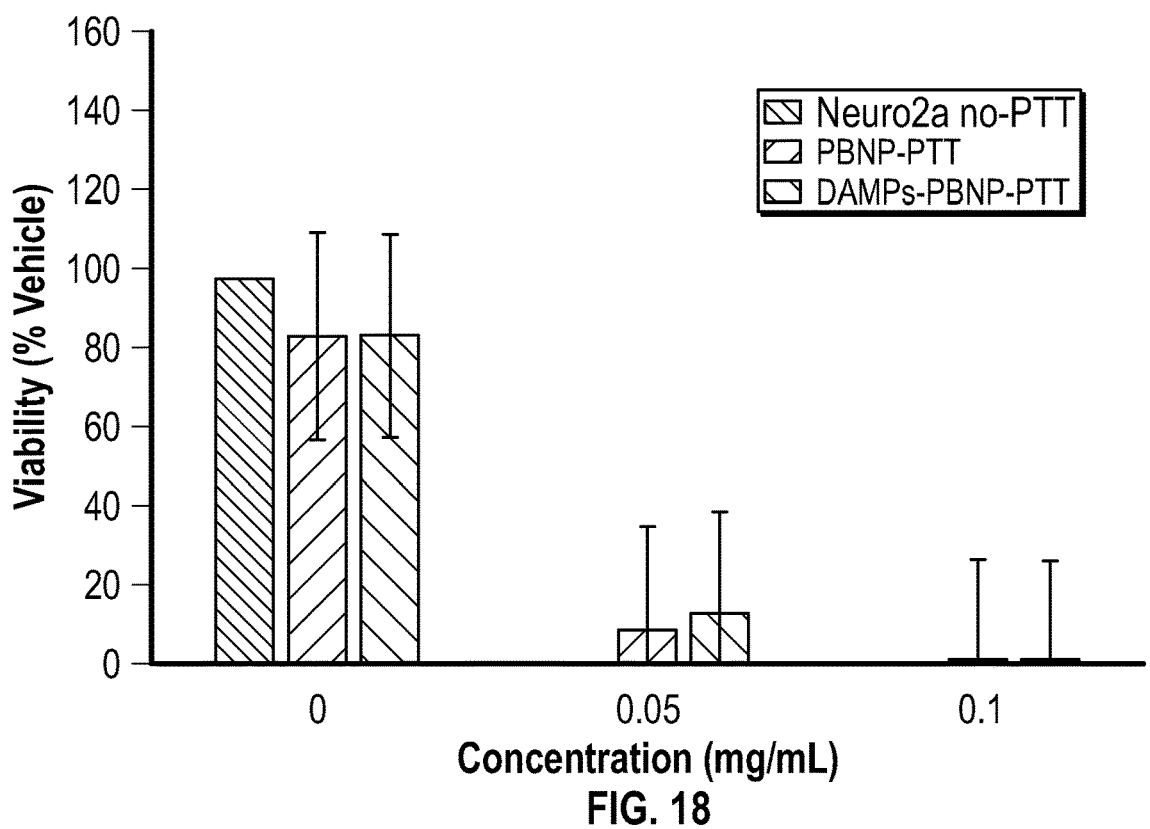

FIG. 18 depicts a bar graph showing killing efficacy of 0.05 mg/ml and 0.1 mg/ml uncoated PBNP-PTT and 0.05 mg/ml and 0.1 mg/ml DAMPs-PBNP-PTT in Neruro2a cells 24 hours after irradiation by an 808 nm NIR laser for 10 minutes at 0.75 W laser power.

Figure 19A:
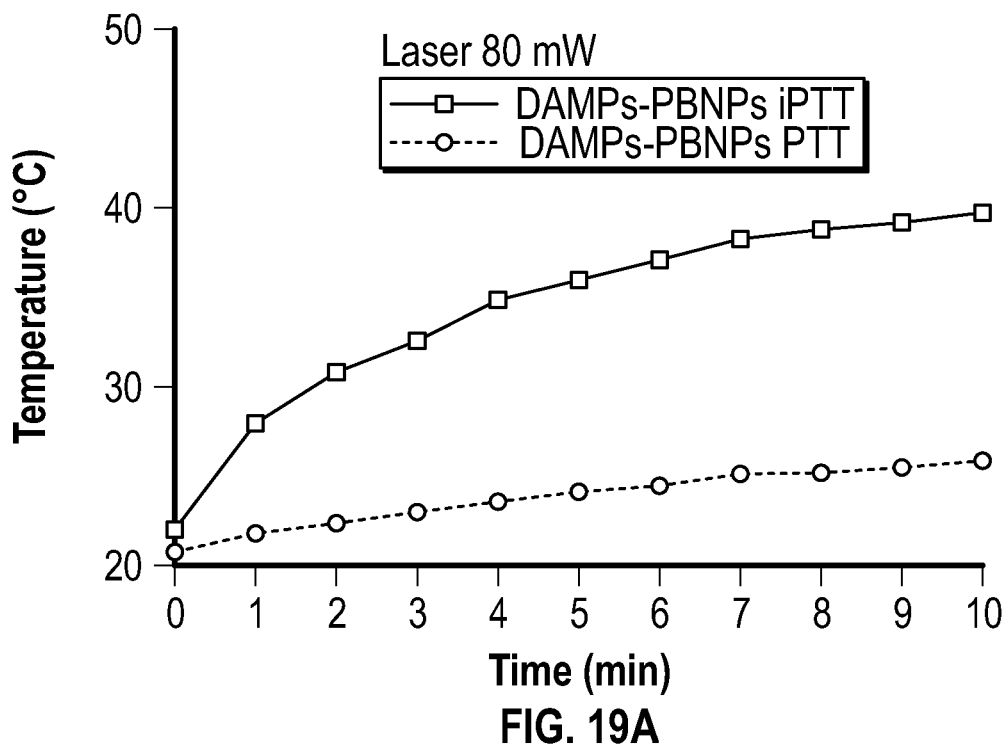

FIG. 19A depicts a graph showing the photothermal heating characteristics of 0.1 mg/mL uncoated DAMPs-PBNPs following irradiation at 80 mW laser power by either 1) an external beam laser (PTT); or 2) a laser connected to a 0.85 micrometer spherical diffuser (PTTi) for 0-10 minutes.

Figure 19B:
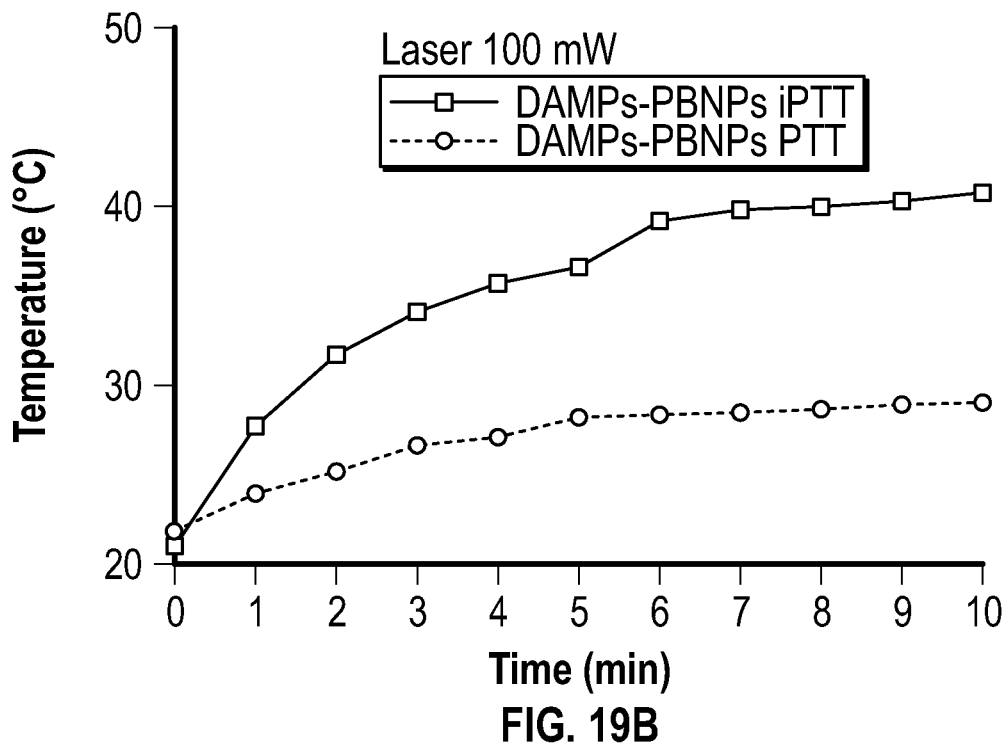

FIG. 19B depicts a graph showing the photothermal heating characteristics of 0.1 mg/mL uncoated DAMPs-PBNPs following irradiation at 100 mW laser power by either 1) an external beam laser (PTT); or 2) a laser connected to a 0.85 micrometer spherical diffuser (PTTi) for 0-10 minutes.

DETAILED DESCRIPTION

Compositions comprised of at least a nanocomposite directed toward treating and/or preventing cancer are detailed below. In general, the compositions disclosed herein comprise a biofunctionalized nanocomposite. As used herein, the term "nanocomposite" refers to a composition comprised of a nanoparticle core partially or completely surrounded with a material. As used herein, the term "biofunctionalized nanocomposite" refers to a nanocomposite that has been modified to add at least one biological function. In various embodiments, compositions of the present disclosure comprise a core comprising a nanoparticle formed of Prussian blue materials and a shell obtained by partially or completely encapsulating the Prussian blue core with a biocompatible coating wherein at least one biomolecule is attached to, or absorbed to, the biocompatible coating. In various embodiments, compositions of the present disclosure may be used to treat tumor cells, prevent tumor cell metastasis, and/or treat and/or prevent cancer using photothermal therapy.

(I) Compositions

One aspect of the present disclosure encompasses a composition containing a biofunctionalized nanocomposite. A composition disclosed herein may encompass a nanoparticle formed of Prussian blue materials, a biocompatible coating, and a biomolecule. A composition disclosed herein may further comprise one or more imaging agents. A composition disclosed herein may be a photothermal therapy agent.

(a) Prussian Blue Materials

In various embodiments, compositions disclosed herein comprise a nanoparticle formed of at least one or more Prussian blue materials. As used herein, "Prussian blue materials", "Prussian blue" and "Prussian blue compounds" are used interchangeably. Unless indicated otherwise, the symbols used to represent the elements of which the Prussian blue materials and/or analogs thereof of the present disclosure are comprised are the symbols used in the periodic table of elements to represent the chemical elements (for example, "Fe" represents iron, etc.).

In various embodiments, compositions disclosed herein may comprise doped Prussian blue compounds. In various aspects, compositions disclosed herein may comprise Prussian blue materials represented by general formula (I):

$$A_xB_yM_4[M'(CN)_6]_z \cdot nH_2O \quad (I),$$

which is coated with a biocompatible shell onto which targeting, imaging and/or therapeutic agents are attached. In the compounds of general formula (I), A represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and in any combination thereof;

B represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and in any combination thereof;

M represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and in any combination thereof;

M' represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and in any combination thereof; x is from 0.1 to about 1; y is from 0.1 to about 1; z is from 0.1 to about 4; and n is from 0.1 to about 24.

In preferred embodiments, A represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and in any combination thereof. In the further preferred embodiments, A represents at least one of Li, Na, K, Rb, Cs, and Fr, in any oxidation state and in any combination thereof. In other preferred embodiments, A represents Li, Na, K, Rb, in any oxidation state and in any combination thereof. In other preferred embodiments, A represents a mixture of K and other elements represented by A, where the molar ratio of K in the mixtures is at least 0.9, preferably, at least 0.95, most preferably at least 0.99. In the most preferred embodiments, A only represents K.

In some embodiments, B represents at least one of Cr, Mn, Fe, Eu, Gd, and Tb, in any oxidation state and in any combination thereof. In other preferred embodiments, B represents a mixture of Mn, Gd, and other elements represented by A, where the molar ratio of the combination of Mn and Gd in the mixtures is at least 0.9, preferably, at least 0.95, most preferably at least 0.99. In the most preferred embodiments, A represents a mixture of only Mn and Gd, in any oxidation state and in any combination thereof.

In other embodiments, M represents at least one of Fe, Co, and Ni, in any oxidation state and in any combination thereof. In the most preferred embodiments, M represents only Fe. In still other embodiments, M' represents at least one of Fe, Co, and Ni, in any oxidation state and in any combination thereof. In yet other embodiments, M' represents only Fe. In preferred embodiments, each of M and M', simultaneously, represents only Fe, in any oxidation state thereof.

As used herein, the term "in any combination thereof" for A, B, M, and M' means that at least two of the elements that are represented by A, B, M, and M' can be present in any molar ratios so long as the sum total is equal to the value for x, y, and z, and, in the case of M, the elements can be present in any molar ratios so long as the total amount of the M elements is equal to 4. Preferably, x in general formula (I) is from 0.2 to 0.9, more preferably from 0.3 to 0.8, more preferably still from 0.4 to 0.7, and most preferably from 0.5 to 0.6. Preferably, y in general formula (I) is from 0.2 to 0.9, more preferably from 0.3 to 0.8, more preferably still from 0.4 to 0.7, and most preferably from 0.5 to 0.6. Preferably, z in general formula (I) is from 0.2 to 3.5, more preferably from 0.3 to 0.8, more preferably still from 0.4 to 0.7, and most preferably from 0.5 to 0.6. All real numbers within the ranges for x, y, z, and n are included.

In various embodiments, a particularly preferred species of the Prussian blue compound represented by general formula (I) are $K_{0.53}Gd_{0.89}Fe^{III}_4[Fe^{II}(CN)_6]_{3.8} \cdot 1.2H_2O$ and $K_{0.6}Mn_{0.7}Fe^{III}_4[Fe^{II}(CM_6]_{3.5} \cdot 3H_2O$.

In various embodiments, compositions disclosed herein may comprise Prussian blue materials that belong to the class of iron hexacyanoferrate (II). In some aspects, compositions disclosed herein may comprise Prussian blue materials represented by general formula (II):

$$Fe_4^{III}[Fe^{II}(CN)_6]_3 \cdot nH_2O \quad (II)$$

wherein the value n represents an integer from 1 to about 24.

In other aspects, compositions disclosed herein may comprise Prussian blue salts represented by general formula (III):

$$A_{4x}Fe_{4-x}^{III}[Fe^{II}(CN)_6]_{3+x} \cdot nH_2O \quad (III)$$

where A is an alkali metal such as lithium (Li+), sodium ($Na^+$), Potassium ($K^+$), Rubidium ($Rb^+$), Cesium ($Cs^+$), or it can be Ammonium ($NH^{4+}$) or Thallium ($Tl^+$). The value x can be any number, e.g. a fraction, from e.g. $0 \leq x \leq 1$ and n is about 1 to about 24, and preferably is from about 14 to about 16.

In various embodiments, compositions disclosed herein may comprise soluble Prussian blue materials insoluble Prussian blue materials. In an aspect, insoluble Prussian blue materials may be characterized by coordinating water molecules therein.

In various embodiments, compositions disclosed herein may comprise one or more metal isotopes doped to the Prussian blue materials described herein. In some aspects, a metal isotope may be Li, Na, K, Rb, Cs, Fr, Ga, In, Tl, Ca, Sc, V, Cr, Mn, Fe, Co, Ni, Cu, Zn, Sr, Y, Zr, Nb, Mo, Ru, Rh, Pd, Ag, Cd, Ba, La, Sm, Eu, Gd, Tb, Dy, Ho, Lu, Hf, Ta, W, Re, Os, Ir, Pt, Au, Hg, Pb, Bi or a combination thereof. In a preferred embodiment, the metal isotope may be Cs, Ga, Tl, In, V, Cr, Mn, Fe, Co, Ni, Cu, Mo, Ru, Ag, W, Pt, Au, Hg, Eu, Gd, or a combination thereof.

In some embodiments, a metal isotope suitable for use in the compositions disclosed herein may be present in any sufficient oxidation state theoretically possible. In some aspects, a metal isotope may be Li(I), Na(I), K(I), Cs(I), Fr(I), Ga(III), Ir(III), Tl(I), Tl(III), Ca(II), Sc(III), V(III), V(IV), Cr(II), Cr(III), Mn(II), Mn(IV), Fe(II), Fe(III), Co(II), Co(III), Ni(II), Ni(III), Cu(I), Cu(II), Zn(II), Sr(II), Y(III), Zr(IV), Nb(IV), Nb(V), Mo(IV), Mo(V), Ru(III), Ru(IV), Rh(II), Rh(III), Rh(IV), Pd(II), Pd(IV), Ag(I), Cd(II), Ba(II), La(III), Sm(II), Sm(III), Eu(II), Eu(III), Gd(III), Tb(III), Tb(IV), Dy(III), Ho(III), Lu(III), Hf(IV), Ta(V), W(IV), W(V), Re(I), Os(IV), Ir(II), Ir(III), Pt(II), Pt(IV), Au(I), Au(III), Hg(I), Hg(II), Pb(II), Pb(IV), Bi(III), or a combination thereof.

In various embodiments, a metal isotope suitable for use in the compositions disclosed herein may be linked to Prussian blue materials in a chemical or physical route. As a non-limiting example of chemical linkage, a metal isotope is bound by covalent bond, whereas the metal isotope replaces the Fe atom in the complex structure of a Prussian blue compound. In an aspect, Prussian blue materials may be represented by general formula (I):

$$A_xB_yM_4[M'(CN)_6]_z \cdot nH_2O \quad (I),$$

wherein M and M' denote the same or different and independently from each other Cu-61, Cu-64, Cu-67, Zn-62, Zn-69m, Zn-69, Pb-206, Pb-207, Pb-208, Pb-209, Pb-210, Pb-211, Pb-212, Pb-213, Pb-214, Ag-105, Ag-106, Ag-112, Ag-113, Pt-186, Pt-187, Pt-188, Pt-190, Pt-191, Pt-197, La-131, La-132, La-133, La-135, La-140, La-141, La-142, Eu-150m, Eu-152m, Eu-158, Eu-145, Eu-146 and Eu-147, especially Cu-61, Cu-64, Cu-67, Ag-105, Ag-106, Ag-112, Ag-113, Pt-185, Pt-186, Pt-187, Pt-188, Pt-189, Pt-190, Pt-19 and Pt-197. A, B, y, x and n are as defined above. In a preferred embodiment, Prussian blue materials may be ng of $Ag_4[Fe(CN)_6]$, $Pb_2[Fe(CN)_6]$, $Sn_2[Fe(CN)_6]$, $Co[Cr(CN)_6]_{2/3}$ or a combination thereof.

As a non-limiting example of physical linkage, a metal isotope may be bounded by physical or physicochemical bonds, such as ion exchange, absorption, mechanical trapping. In an aspect, a metal isotope can be adsorbed on the surface of Prussian blue materials or incorporated into the vacancies of Prussian blue materials.

In various embodiments, compositions disclosed herein may comprise a metal isotope emitting any kind of radiation known in the field. In an aspect, the radiation may be alpha, beta, gamma, positron radiation, or a combination thereof. In some embodiments, compositions disclosed herein may comprise a metal isotope emitting alpha or beta radiation. In an aspect, a metal isotope emitting alpha or beta radiation may be Sc-47, Sc-48, Cu-67, Zn-69, Rb-86, Rb-84, Y-90, Zr-95, Zr-97, Nb-95, Nb-96, Nb-98, Ag-112, Ag-113, Cd-115, Cd-117, Cd-118, Cs-136, Cs-138, La-140, La-141, La-142, Sm-153, Eu-150m, Eu-152m, Eu-158, Tb-149, Dy-165, Dy-166, Ho-164, Ho-166, Ho-167, Hf-183, Ta-183, Ta-184, Ta-185, Re-186, Re-188, Re-189, Os-191, Os-193, Os-194, Os-195, Os-196, Ir-193, Ir-195, Pt-197, Pt-200, Au-196, Au-199, Hg-203, Hg-208, Pb-209, Pb-212, Bi-212, Bi-213, or a combination thereof.

In other embodiments, compositions disclosed herein may comprise a metal isotope emitting gamma or positron radiation. In an aspect, a metal isotope emitting gamma or positron radiation may be Sc-43, Sc-44, Cu-61, Cu-64, Zn-62, Zn-69m, Ga-67, Ga-68, Rb-81, Rb-82m, Y-84, Y-85, Y-86, Zr-86, Zr-87, Zr-88, Zr-89, Zr-90, Nb-88, Nb-89, Nb-90, Ag-105, Ag-106, Cd-104, Cd-105, Cd-107, Cd-111, Cs-127, Cs-129, Cs-131, Cs-134, Cs-135, La-131, La-132, La-133, La-135, Sm-141, Sm-142, Eu-145, Eu-146, Eu-147, Eu-152m, Tb-147, Tb-150, Tb-151, Tb-152, Tb-154, Tb-154m, Tb-156, Tb-156m, Dy-152, Dy-153, Dy-155, Dy-157, Ho-155, Ho-156, Ho-158, Ho-159, Ho-160, Ho-164, Hf-166, Hf-168, Hf-170, Hf-171, Hf-173, Hf-179, Ta-171, Ta-172, Ta-173, Ta-174, Ta-175, Ta-176, Ta-177, Ta-178, Re-181, Re-182, Re-183, Re-184, Re-186, Re-188, Re-190, Os-180, Os-181, Os-182, Os-183, Ir-183, Ir-184, Ir-185, Ir-186, Ir-187, Ir-188, Ir-189, Ir-190, Pt-185, Pt-186, Pt-187, Pt-188, Pt-189, Pt-190, Pt-191, Pt-197, Au-190, Au-191, Au-192, Au-193, Au-194, Au-196, Au-198, Au-199, Au-200, Au-201, Hg-190, Hg-191, Hg-193, Hg-197, Tl-194, Tl-195, Tl-196, Tl-197, Tl-198, Tl-199, Tl-200, Tl-201, Tl-202, Tl-203, Tl-204, Pb-206, Pb-207, Pb-208, Pb-209, Pb-210, Pb-211, Pb-212, Pb-213, Pb-214, Bi-200, Bi-201, Bi-201, Bi-203, Bi-204, Bi-205, Bi-206, or a combination thereof.

In various embodiments, compositions disclosed herein may comprise soluble Prussian blue materials forming a particle. In some aspects, a particle formed of Prussian blue materials may be a nanoparticle. In other aspects, a particle formed of Prussian blue materials may be a microparticle. In still other aspects, a particle formed of Prussian blue materials may be about 1 nanometer (nm) to about 10 microns (μm). In preferred aspects, a particle formed of Prussian blue materials range from about 10 nm to about 1 μm.

In various embodiments, compositions disclosed herein may comprise soluble Prussian blue materials synthesized by methods known in the art. In an aspect, a starting material can be a commercially available Prussian blue particle. In an aspect, a starting material may be commercially available from Radiogardase® (by Heyltex). In another aspect, starting material can be a Prussian blue particle synthesized from $FeCl_3$ and $K_4[Fe(CN)_6]$ which may be acidified for example with organic or inorganic acids (such as HCl, citric acid etc.) which is mixed. In this aspect, the step of mixing the solution may be temperature and pH controlled. In an aspect, a temperature suitable for mixing the solution disclosed herein may be about 20° C., about 21° C., about 22° C., about 23° C., about 24° C., about 25° C., or about 26° C. In an aspect, a pH suitable for mixing the solution disclosed herein may be about 3, about 4, about 5, about 6, or about 7. In other aspects, one or more additives known in the field to aid in formation of Prussian blue particles with homogeneous size distribution and/or subsequent incorporation of a metal isotope and/or covering Prussian blue particles with a biocompatible coating as disclosed herein may be added during mixing of the solution disclosed herein.

In some embodiments, Prussian blue materials are synthesized by reacting a metallic salt with a metal cyanide ($[M'(CN)_6]^{3-}$) in a solvent. In some aspects, the metallic salt comprises, consists essentially of, or consists of a salt of salt of V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho in any oxidation state thereof and in any combination thereof. In other aspects, the metallic salt comprises, consists essentially of, or consists of a metallic salt of a chloride, a nitrate, a nitrite, a sulfate, a fluorinate, a glutamate, an acetate, a carbonate, a citrate, a phosphate, a sulfate and any combination thereof. In still other aspects, the metal cyanide comprises, consists essentially of, or consists of a metal cyanide represented by $[M'(CN)_6]^{3-}$, wherein M' represents V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho in any oxidation state thereof and in any combination thereof.

In some embodiments, the solvent in which the reaction between the metallic salt and the metallic cyanide described above occurs may not be particularly limited, so long as the reaction proceeds in this solvent. In an aspect, the solvent comprises, consists essentially of, or consists of water, air, or an organic solvent. In a preferred aspect, the solvent is ultrapure water. As used herein, the "ultrapure water" refers to "grade 1" water as defined by the International Organization for Standardization (ISO), with resistivity of 18.2 MΩ·cm. As used herein, the terms "ultrapure water" and "Milli-Q water" are synonymous.

In some embodiments, the solvent in which the reaction between the metallic salt and the metallic cyanide described above occurs is an organic solvent. In an aspect, the organic solvent can be hydrophilic to any degree or hydrophobic to any degree. In a preferred aspect, the organic solvent comprises, consists essentially of, or consists of hexane; benzene; toluene; diethyl ether; chloroform; 1,4-dioxane; ethyl acetate; tetrahydrofuran (THF); dichloromethane; acetone; acetonitrile (MeCN); dimethylformamide (DMF); dimethyl sulfoxide (DMSO); a polar protic solvent; acetic acid; n-butanol; isopropanol; n-propanol; ethanol; methanol; formic acid; and any combination thereof, so long as the metallic salt and the metallic cyanide are sufficiently dissolved in the combination and the reaction proceeds in this combination of solvents.

(b) Biocompatible Coatings

In various embodiments, compositions disclosed herein comprise a shell partially or completely encapsulating a nanoparticle. In some aspects, a shell encapsulates about 25%, about 50%, about 75%, or about 100% of the nanoparticle. In a preferred aspect, a shell completely encapsulates a nanoparticle formed of Prussian blue materials as disclosed herein.

In various embodiments, a shell is comprised of a biocompatible coating. In an a aspect, a biocompatible coating comprises one or more biocompatible materials assisting to in vivo and in vitro use of compositions disclose herein. In some embodiments, a biocompatible coating of the shell may comprise at least one material selected from the group consisting of dextran; chitosan; silica; polyethylene glycol (PEG); avidin; a proteins; a nucleic acids; a carbohydrates; a lipid; neutravidin; streptavidin; gelatin; collagen; fibronectin; albumin; a serum protein; lysozyme; a phospholipid; a polyvinyl pyrrolidone (PVP); a polyvinyl alcohol; a polyethylene glycol diacrylate; polyethylenimine (PEI); and a combination thereof. Without wishing to be bound to any particular theory, the biocompatible coating is believed to prevent the compositions from aggregating and to prevent leakage of ions from the core to the surrounding environment.

In some embodiments, a dextran of the biocompatible coating may comprise a dextran that is a complex, branched polysaccharide having chains of varying lengths, preferably chains having lengths of from about 3 to about 2000 kDa. In other embodiments, a chitosan of the biocompatible coating may comprise a linear polysaccharide having randomly distributed units of β-(1-4)-linked D-glucosamine (deacetylated unit) and units of N-acetyl-D-glucosamine (acetylated unit). In still other embodiments, a silica of the biocompatible coating may comprise an oxide of silicon with the chemical formula $SiO_2$. In yet other embodiments, a polyethylene glycol (PEG) of the biocompatible coating may comprise polyethylene oxide (PEO) or polyoxyethylene oxide (POE). In other embodiments, an avidin of the biocompatible coating may comprise a protein produced in the oviducts of birds, reptiles and amphibians deposited in the whites of their eggs. In yet other embodiments, an albumin of the biocompatible coating may comprise bovine serum albumin (BSA, fraction V), human serum albumin (HSA) and all serum albumin derived from mammals. In an aspect, serum proteins of the biocompatible coating may comprise at least one member selected from the group consisting of Orosomucoid; antitrypsin; alpha-1 antichymotrypsin; alpha-2 macroglobulin (AMG); haptoglobin; transferrin; beta lipoprotein (LDL); immunoglobulin A (IgA); immunoglobulin M (IgM); immunoglobulin G (IgG); immunoglobulin E (IgE); and immunoglobulin D (IgD). In some embodiments, a lysozyme of the biocompatible coating may be of N-acetylmuramide glycanhydrolase. In still other embodiments, phospholipids of the biocompatible coating may comprise of all natural phospholipids and synthetic phospholipids. Non-limiting examples of natural phospholipids and synthetic phospholipids include DMPA, DPPA, DSPA DDPC, DLPC, DMPC, DPPC, DSPC, DOPC, POPC, DEPC DMPG, DPPG, DSPG, POPG DMPE, DPPE, DSPE DOPE DOPS mPEG-phospholipid, polyglycerin-phospholipid, functionalized-phospholipid, and terminal activated-phospholipid. In other embodiments, a polyvinyl pyrrolidone (PVP) of the biocompatible coating may comprise a polymer made from repeating monomer N-vinylpyrrolidone units. In an aspect, the molecular weight of the PVP is not particularly limited, as long as the PVP is suitable for use in the biocompatible coating of the present disclosure. As used herein, the terms "polyvidone" and "povidone" are synonymous with PVP. In yet other embodiments, a polyvinyl alcohol of the biocompatible coating may comprise PVOH, PVA, and PVAI. In an aspect, molecular weights of the PVOH, PVA, and PVAI are not particularly limited, as long as the PVOH, PVA, and PVAI are suitable for use in the biocompatible coating of the present disclosure. In other embodiments, a polyethylene glycol diacrylate of the biocompatible coating may comprise a polyethylene glycol terminated with acrylate groups. In an aspect, molecular weight of the polyethylene glycol diacrylate is not particularly limited, as long as the polyethylene glycol diacrylate is suitable for use in the biocompatible coating of the present disclosure. In some other embodiments, lipids of the biocompatible coating may comprise sterols, fats, oils, waxes, vitamin A, vitamin D, vitamin E, vitamin K, phospholipids of claim 5q, (mono-, di-, tri-) glycerides, or a combination thereof.

In preferred embodiments, a biocompatible coating of the shell of compositions disclosed herein may comprise one or more polymers. In an aspect, a polymer suitable for use in a biocompatible coating disclosed herein may be polyethylene glycol, polypropylene glycol, polyoxyethylene ether, polyanethol sulfonic acid, polyethylene imine, polymaleimide, polyvinyl alcohol, polyvinyl chloride, polyvinyl acetate, polyvinyl pyrrolidone, polyvinyl sulfate, polyacrylic acid, polymethacrylic acid, polylactide, polylactide glycide, or a combination thereof. In a perfered aspect, the biocompatible coating comprises polyethylene imine (PEI).

In various embodiments, the biocompatible coating can be applied to the core of the compositions disclosed herein by a variety of physical and chemical interactions including, but not limited to: electrostatic (charge-based), covalent, hydrophobic and van der Waal's interactions. In a preferred embodiment, the biocompatible coating is applied by suspending the core in a solution comprised of one or more materials selected from the group consisting of dextran; chitosan; silica; polyethylene glycol (PEG); avidin; a proteins; a nucleic acids; a carbohydrates; a lipid; neutravidin; streptavidin; gelatin; collagen; fibronectin; albumin; a serum protein; lysozyme; a phospholipid; a polyvinyl pyrrolidone (PVP); a polyvinyl alcohol; a polyethylene glycol diacrylate; polyethylenimine (PEI); and a combination thereof.

(c) Biomolecules

In various embodiments, compositions disclosed herein comprise a shell partially or completely encapsulating a nanoparticle with biocompatible coating wherein at least one biomolecule may be attached to, or absorbed to, the biocompatible coating. In a preferred aspect, the shell completely encapsulates a nanoparticle formed of Prussian blue materials with biocompatible coating wherein at least one biomolecule may be attached to, or absorbed to, the biocompatible coating.

In various embodiments, a biocompatible coating disclosed herein may absorb at least 25%, at least 50%, or at least 75% biomolecule weight by total weight of the biocompatible coating. In other embodiments, at least 25%, at least 50%, at least 75%, at least 100% of the outer surface of the biocompatible coating has biomolecules attached.

In various embodiments, a biomolecule attached to, or absorbed to, the biocompatible coating may comprise an antibody, a peptide, a protein, an enzyme, an amino acid, a nucleic acid, a carbohydrate, a fat, an aptamer, a small molecule, a synthetic molecule or a combination thereof.

In some embodiments, at least one of the biomolecules is a nucleic acid. In an aspect, a nucleic acid may comprise a pathogen-associated molecular pattern (PAMPs) motif. In yet another aspect, a nucleic acid may comprise a damage-associated molecular pattern (DAMPs) motif.

In some embodiments, a nucleic acid may be DNA (deoxyribonucleic acid), RNA (ribonucleic acid), a peptide nucleic acid, a morpholino-nucleic acid, a locked nucleic acid, a glycol nucleic acid, a threose nucleic acid, an oligonucleotide, or a combination thereof.

In preferred embodiments, the biomolecule may be an oligonucleotide. In an aspect, an oligonucleotide may be at least 5, at least 10, at least 25, at least 50, at least 75, at least 100, at least 250, or at least 500 base pairs (bp). In another aspect, the oligonucleotide may be an oligodeoxynucleotide. In still another aspect, the oligonucleotide may comprise a pathogen-associated molecular pattern (PAMPs) motif. In yet another aspect, the oligonucleotide may comprise a damage-associated molecular pattern (DAMPs) motif. In a preferred embodiment, the biomolecule is a CpG oligodeoxynucleotide.

In some embodiments, at least one of the biomolecules may be an antibody. As used herein, an "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and immunologically active portions of an immunoglobulin molecule such as, without limitation: Fab, Fab', F(ab')$_2$, F(v), scFv, scFv$_2$, scFv-Fc, minibody, diabody, tetrabody, single variable domain (e.g., variable heavy domain, variable light domain), bispecific, and peptabodies. In an aspect, the antibody may target a pathogen-associated molecular pattern (PAMPs) motif. In yet another aspect, the antibody may target a damage-associated molecular pattern (DAMPs) motif.

In other embodiments, at least one of the biomolecules may be a peptide. In some embodiments, a peptide may consist of any sequence of 50 amino acids or less, excluding zero. In another aspect, a peptide may consist of any sequence of about 2 amino acids to about 50 amino acids. In a preferred aspect, a peptide may consist of any sequence of 20 amino acids or less, excluding zero.

As used herein, "amino acids" are represented by their full name, their three letter code, or their one letter code as well known in the art. Amino acid residues are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. An amino acid as disclosed herein may be either naturally or non-naturally occurring. As used herein, a "naturally occurring amino acid" is one that has the general core structure

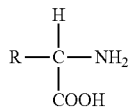

and that is synthesized in nature. of naturally occurring amino acids that may be used in the present disclosure include, but are not limited to, alanine, arginine, asparagine, aspartic acid, carnitine, cysteine, glutamine, glutamic acid, glycine, citrullline, histidine, isoleucine, leucine, lysine, methionine, phenylalanine, proline, serine, threonine, tryptophan, tyrosine, and derivatives, analogs, and combinations thereof. The present disclosure may include levorotary (L) stereoisomers of such amino acids.

As used herein, a "non-naturally occurring amino acid" may be an analog, derivative and/or enantiomer of a naturally occurring amino acid. The term "non-naturally occurring amino acid" includes, but is not limited to, amino acids that occur naturally by modification of a naturally encoded amino acid (including but not limited to, the 20 naturally occurring amino acids contained in body proteins or pyrrolysine and selenocysteine) but are not themselves incorporated into a growing polypeptide chain by the translation complex. Non-limiting examples of non-naturally occurring amino acids that may be used in the present disclosure include L-hydroxypropyl, L-3,4-dihydroxyphenylalanyl, alpha-amino acids such as L-alpha-hydroxylysyl and D-alpha-methylalanyl, L-alpha-methyl alanyl, beta-amino acids, N-acetylglucosaminyl-L-serine, N-acetylglucosaminyl-L-threonine, 0-phosphotyrosine, and isoquinolyl.

As used herein, the term "amino acid" may also encompass chemically modified amino acids, including but not limited to salts, amino acid derivatives (such as amides), and substitutions. Amino acids contained within the compositions of the present disclosure can be modified by methylation, amidation, acetylation or substitution with other chemical groups.

In an aspect, the peptide may target a pathogen-associated molecular pattern (PAMPs) motif. In yet another aspect, the peptide may target a damage-associated molecular pattern (DAMPs) motif. In a preferred aspect, the peptide is a derivative of high-mobility group box 1 protein (HMGB1).

In other embodiments, at least one of the biomolecules may be a protein. As used herein, a "protein" can be a macromolecule comprising 20 or more contiguous amino acid residues. In some embodiments, a protein may consist of any sequence of about 20 amino acids to about 40,000 amino acids, about 100 amino acids to about 20,000 amino acids, or about 200 amino acids to about 10,000 amino acids. In some aspects, a protein may consist of any sequence of about 20 amino acids, about 50 amino acids, about 100 amino acids, about 200 amino acids, about 500 amino acids, about 1,000 amino acids, about 5,000 amino acids, about 10,000 amino acids, about 20,000 amino acids, or about 40,000 amino acids. In preferred aspects, a protein may consist of any sequence of about 200 amino acids to about 400 amino acids.

In some aspects, the protein may be a native protein. In other aspects, the protein may be a synthetic protein. In still other aspects, the protein may be a recombinant protein. In an aspect, a recombinant protein can be a chimeric protein, a fusion protein, a truncated protein or a combination thereof. In other aspects, the protein may be in the form of a miltimer (e.g., a dimer, trimer, tetramer, or oligomer).

In an aspect, the protein may target a pathogen-associated molecular pattern (PAMPs) motif. In yet another aspect, the protein may target a damage-associated molecular pattern (DAMPs) motif. In a preferred aspect, the protein is high-mobility group box 1 protein (HMGB1) or a derivative thereof.

In some embodiments, a biomolecule may further comprise one or more prodrugs. In an aspect, a prodrug suitable for use in compositions disclosed herein may be intracellular Type IA, such as Acyclovir, 5-fluorouracil, cyclophosphamide, diethylstilbestrol diphosphate, L-dopa, 6-mercaptopurine, mitomycin C, zidovudine; intracellular Type IB, such as carbamazepine, captopril, carisoprodol, heroin, molsidomine, paliperidone, phenacetin, primidone, psilocybin, sulindac, and fursultiamine; extracellular Type IIA, such as lisdexamfetamine, loperamide oxide, oxyphenisatin, and sulfasalazine; extracellular Type IIB, such as acetylsalicylate, bacampicillin, bambuterol, chloramphenicol succinate, dihydropyridine pralidoxime, dipivefrin, and fosphenytoin; and extracellular Type IIC, such as ADEPTs, GDEPs, VDEPs, or a combination thereof.

(d) Imaging Agents

In various embodiments, compositions disclosed herein comprise a shell partially or completely encapsulating a nanoparticle with a biocompatible coating wherein the biocompatible coating may further comprise at least one imaging agent. In some aspects, the biocompatible coating can comprise about 10%, about 20%, about 50%, or about 75% total amount of imaging agent by total weight of biocompatible coating. In a preferred aspect, the shell completely encapsulates a nanoparticle formed of Prussian blue materials with biocompatible coating wherein the biocompatible coating may further comprise at least one imaging agent.

In various embodiments, imaging agents suitable for use in compositions disclosed herein may facilitate medical radiography, magnetic resonance imaging, scintigraphy, X-ray computed tomography, single-photon emission computed tomography, positron emission tomography, photoacoustic imaging, ultrasound imaging, near infrared imaging, optical imaging, fluorescence imaging or combinations thereof. In an aspect, an imaging agent may be a fluorophore, a contrast agent, or a combination thereof.

In some embodiments, an imaging agent suitable for use in compositions disclosed herein may be one or more fluorophores. In some aspects, the biocompatible coating can comprise about 10%, about 20%, about 50%, or about 75% total amount of fluorophores by total weight of biocompatible coating.

In other embodiments, a fluorophore suitable for use in compositions disclosed herein may be a fluorescein compound, a rhodamine compound, a xanthene compound, a cyanine compound, a naphthalene compound, a coumarin compound, an oxadiazole compound, a pyrene compound, an oxazine compound, an acridine compound, an arylmethine compound, a tetrapyrrole compound, proprietary molecules, or a combination thereof. In some aspects, a xanthene compound may be fluorescein, rhodamine, Oregon green, eosin, Texas red, naphthalene compounds such as dansyl and prodan compounds, or a combination thereof. In other aspects, a cyanine compound may be cyanine, indocarbocyanine, oxacarbocyanine, thiacarbocyanine, merocyanine, or a combination thereof. In still other aspects, an oxadiazole compound may be pyridyloxazole, nitrobenzoxadiazole, benzoxadiazole, or a combination thereof. In yet other aspects, a pyrene compound may be cascade blue. In other aspects, a oxazine compound may be Nile red, Nile blue, cresyl violet, oxazine 170, or a combination thereof. In still other aspects, a acridine compound may be proflavin, acridine orange, acridine yellow, or a combination thereof. In yet other aspects, an arylmethine compound may be auramine, crystal violet, malachite green, or a combination thereof. In some asepcts, a tetrapyrrole compound may be porphin, phtalocyanine, bilirubin, or a combination thereof. In other aspects, a proprietary molecule may be CF dye (Biotium), BODIPY (Invitrogen), Alexa Fluor (Invitrogen), DyLight Fluor (Thermo Scientific, Pierce), Atto and Tracy (Sigma Aldrich), FluoProbes (Interchim), DY and Mega-Stokes Dyes (Dyomics), Sulfo Cy dyes (CYANDYE, LLC), Setau and Square Dyes (SETA BioMedicals), Quasar and Cal Fluor dyes (Biosearch Technologies), SureLight Dyes (APC, RPE, PerCP, Phycobilisomes) (Columbia Biosciences]), APC, APCXL, RPE, BPE (Phyco-Biotech), or a combination thereof.

In some embodiments, an imaging agent suitable for use in compositions disclosed may be one or more contrast agents. In some aspects, the biocompatible coating can comprise about 10%, about 20%, about 50%, or about 75% total amount of contrast agent by total weight of biocompatible coating.

In other embodiments, one or more contrast agents suitable for use in compositions disclosed herein may be iodine and barium compounds, 5-100 nm iron oxide nanoparticles, nanoparticles or nanorods of platinum, palladium, silver gold and any combination thereof, $^{18}$F-fluorodeoxyglucose, $^{11}$C (carbon-11), $^{13}$N (nitrogen-13), $^{15}$O (oxygen-15), $^{18}$F (fluorine-18), $^{82}$Rb (rubidum-82), or any combination thereof.

(e) Biofunctionalized Nanocomposites

In various embodiments, compositions disclosed herein comprise a biofunctionalized nanocomposite. As used herein, the term "nanocomposite" refers to a composition comprised of a nanoparticle core partially or completely surrounded with a material. As used herein, the term "biofunctionalized nanocomposite" refers to a nanocomposite that has been modified to add at least one biological function.

In various embodiments, biofunctionalized nanocomposites of the present disclosure comprise a core comprising a nanoparticle formed of Prussian blue materials and a shell obtained by partially or completely encapsulating the Prussian blue core with a biocompatible coating wherein at least one biomolecule is attached to, or absorbed to, the biocompatible coating.

In various embodiments, biofunctionalized nanocomposites disclosed herein may comprise soluble Prussian blue materials forming a nanoparticle prepared as described herein. In some aspects, the nanoparticle may be formed of one or more of the Prussian blue materials disclosed herein. In a preferred aspect, the Prussian blue materials may be an iron hexacyanoferrate (II) compound as disclosed herein. In another preferred aspect, the Prussian blue materials may be represented by general formula (I):

$$A_xB_yM_4[M'(CN)_6]_z \cdot nH_2O \qquad (I)$$

wherein A, B, M, M', y, x and n are as defined above.

In other embodiments, a nanoparticle formed of Prussian blue materials suitable for use in the biofunctionalized nanocomposites disclosed herein may be about 1 nanometer (nm) to about 10 microns (μm). In still other aspects, a particle formed of Prussian blue materials may be about 5 nm to about 500 nm. In preferred aspects, a particle formed of Prussian blue materials may be about 10 nm to about 1 μm.

In various embodiments, biofunctionalized nanocomposites disclosed herein may comprise a core comprising a nanoparticle formed of Prussian blue materials and a shell obtained by partially or completely encapsulating the Prussian blue core with a biocompatible coating. In some aspects, a shell encapsulates about 25%, about 50%, about 75%, or about 100% of the nanoparticle. In a preferred aspect, the shell completely encapsulates a nanoparticle formed of Prussian blue materials as disclosed herein.

In various embodiments, biofunctionalized nanocomposites disclosed herein may comprise a biocompatible coating prepared as described herein. In some aspects, a shell may be formed of one or more of the biocompatible coating materials disclosed herein. In other aspects, a biocompatible coating suitable for use in a biofunctionalized nanocomposite disclosed herein may be dextran, chitosan, silica, polyethylene glycol (PEG), avidin, a protein, a nucleic acid, a carbohydrate, a lipid, neutravidin, streptavidin, gelatin, collagen, fibronectin, albumin, a serum protein, a lysozyme, a phospholipid, a polyvinyl pyrrolidone (PVP), a polyvinyl alcohol, polyethylene glycol diacrylate, polyethylenimine (PEI), or a combitation thereof. In other aspects, a biocompatible coating may comprise PEI having an average molecular weight (MW) in the range from about 100 daltons to about 100,000 daltons. In some aspects, PEI may have an average molecular weight of about 100 daltons, about 500 daltons, about 1,000 daltons, about 1,500 daltons, about 2,000 daltons, about 2,500 daltons, about 3,000 daltons, about 3,500 daltons, about 4,000 daltons, about 4,500 daltons, about 5,000 daltons, about 6,000 daltons, about 7,000 daltons, about 8,000 daltons, about 9,000 daltons, about 10,000 daltons, about 20,000 daltons, about 30,000 daltons, about 40,000 daltons, about 50,000 daltons, about 60,000 daltons, about 70,000 daltons, about 80,000 daltons, about 90 000 daltons, or about 100,000 daltons. In yet other aspects, a biocompatible coating may comprise PEI polymers of at least two different average molecular weights ranging from about 100 daltons to about 100,000 daltons. In other aspects, a biocompatible coating may comprise PEI polymers of at least two different average molecular weights wherein there molecular weight may be about 100 daltons, about 500 daltons, about 1,000 daltons, about 1,500 daltons, about 2,000 daltons, about 2,500 daltons, about 3,000 daltons, about 3,500 daltons, about 4,000 daltons, about 4,500 daltons, about 5,000 daltons, about 6,000 daltons, about 7,000 daltons, about 8,000 daltons, about 9,000 daltons, about 10,000 daltons, about 20,000 daltons, about 30,000 daltons, about 40,000 daltons, about 50,000 daltons, about 60,000 daltons, about 70,000 daltons, about 80,000 daltons, about 90 000 daltons, about 100,000 daltons, or a combination thereof.

In various embodiments, biofunctionalized nanocomposites disclosed herein may comprise a shell partially or completely encapsulating a nanoparticle with biocompatible coating wherein at least one biomolecule may be attached to, or absorbed to, the biocompatible coating. In various embodiments, the biocompatible coating disclosed herein may absorb at least 25%, at least 50%, or at least 75% biomolecule weight by total weight of the biocompatible coating. In other embodiments, at least 25%, at least 50%, at least 75%, or at least 100% of the outer surface of the biocompatible coating comprises attached biomolecules.

In some aspects, biomolecules may be one or more of the biomolecules disclosed herein. In an aspect, a biomolecule suitable for use in a biofunctionalized nanocomposite disclosed herein may be an antibody, a peptide, a protein, an enzyme, an amino acid, a nucleic acid, a carbohydrate, a fat, an aptamer, a small molecule, a synthetic molecule or a combination thereof. In preferred aspects, a biomolecule suitable for use in a biofunctionalized nanocomposite disclosed herein is a peptide or a nucleic acid.

In other embodiments, biofunctionalized nanocomposites disclosed herein may further comprise an imaging agent. In some aspects, an imaging agent may be one or more of the imaging agents disclosed herein. In a preferred aspect, an imaging agent for use in a biofunctionalized nanocomposite disclosed herein may be a fluorescein compound, a rhodamine compound, a xanthene compound, a cyanine compound, a naphthalene compound, a coumarin compound, an oxadiazole compound, a pyrene compound, an oxazine compound, an acridine compound, an arylmethine compound, a tetrapyrrole compound, a proprietary molecule, or a combination thereof.

In various embodiments, a biofunctionalized nanocomposite disclosed herein can be stable. As used herein, a biofunctionalized nanocomposite is considered to be "stable" when the neither the heating ability nor the hydrodynamic diameter of the composition have changed from baseline measurements.

In some embodiments, a biofunctionalized nanocomposite disclosed herein can be stable from about 20° C. to about 120° C. In an aspect, a biofunctionalized nanocomposite can be stable at no less than about 20° C., about 40° C., about 60° C., about 80° C., about 100° C., or about 120° C. In another aspect, a biofunctionalized nanocomposite can be stable no less than about 80° C.

In other embodiments, a biofunctionalized nanocomposite as disclosed herein can be stable from about 3 days to about 14 days. In an aspect, a biofunctionalized nanocomposite can be stable for about 3 days, about 5 days, about 7 days, about 10 days, about 12 days, or about 14 days. In another aspect, a biofunctionalized nanocomposite can be stable for about 7 days. In yet other embodiments, a biofunctionalized nanocomposite as disclosed herein can be stable from about 0° C. to about 90° C. In an aspect, a biofunctionalized nanocomposite can be stable at about 0° C., about 10° C., about 20° C., about 30° C., about 40° C., about 50° C., about 60° C., about 70° C., about 80° C., or about 90° C. In another aspect, a biofunctionalized nanocomposite can be stable at about 4° C., about 20° C., or about 80° C. In still other embodiments, a biofunctionalized nanocomposite as disclosed herein can be stable from about 0° C. to about 90° C. for up to about 14 days. In an aspect, a biofunctionalized nanocomposite can be stable from about 0° C. to about 90° C. for about 3 days, about 5 days, about 7 days, about 10 days, about 12 days, or about 14 days. In another aspect, a biofunctionalized nanocomposite can be stable at about 0° C., about 10° C., about 20° C., about 30° C., about 40° C., about 50° C., about 60° C., about 70° C., about 80° C., or about 90° C. for about 3 days, about 5 days, about 7 days, about 10 days, about 12 days, or about 14 days. In preferred aspects, a biofunctionalized nanocomposite can be stable at about 4° C., about 20° C., or about 80° C. for about 7 days.

(f) Photothermal Therapy Agents

In various embodiments, compositions disclosed herein comprise a photothermal therapy agent. As used herein, the term "photothermal therapy agent" refers to a composition comprised of light-absorbing materials suitable for use in photothermal therapy.

In various embodiments, photothermal therapy agents of the present disclosure comprise a core comprising a nanoparticle formed of Prussian blue materials and a shell obtained by partially or completely encapsulating the Prussian blue core with a biocompatible coating wherein at least one biomolecule is attached to, or absorbed to, the biocompatible coating.

In various embodiments, photothermal therapy agents disclosed herein may comprise soluble Prussian blue materials forming a nanoparticle prepared as described herein. In some aspects, the nanoparticle may be formed of one or more of the Prussian blue materials disclosed herein. In a preferred aspect, the Prussian blue materials may be iron hexacyanoferrate (II) compounds as disclosed herein. In another preferred aspect, the Prussian blue materials may be represented by general formula (I):

$$A_xB_yM_4[M'(CN)_6]_z \cdot nH_2O \qquad (I)$$

wherein A, B, M, M', y, x and n are as defined above.

In other embodiments, a nanoparticle formed of Prussian blue materials that is suitable for photothermal therapy agents disclosed herein may be about 1 nanometer (nm) to about 10 microns (μm). In still other aspects, a particle formed of Prussian blue may be about 5 nm to about 500 nm. In preferred aspects, a particle formed of Prussian blue materials may be about 10 nm to about 1 μm.

In various embodiments, photothermal therapy agents disclosed herein may comprise a core comprising a nanoparticle formed of Prussian blue materials and a shell obtained by partially or completely encapsulating the Prussian blue core with a biocompatible coating. In some aspects, a shell encapsulates about 25%, about 50%, about 75%, or about 100% of the nanoparticle. In a preferred aspect, a shell completely encapsulates a nanoparticle formed of Prussian blue materials as disclosed herein.

In various embodiments, photothermal therapy agents disclosed herein may comprise a biocompatible coating prepared as described herein. In some aspects, a shell may be formed of one or more of the biocompatible coating materials disclosed herein. In a preferred aspect, a biocompatible coating suitable for photothermal therapy agents as disclosed herein may be dextran, chitosan, silica, polyethylene glycol (PEG), avidin; a protein, a nucleic acid, a carbohydrate, a lipid, neutravidin, streptavidin, gelatin, collagen, fibronectin, albumin, a serum protein, a lysozyme, a phospholipid, a polyvinyl pyrrolidone (PVP), a polyvinyl alcohol, polyethylene glycol diacrylate, polyethylenimine (PEI), or a combination thereof.

In various embodiments, photothermal therapy agents disclosed herein may comprise a shell partially or completely encapsulating a nanoparticle with biocompatible coating wherein at least one biomolecule may be attached to, or absorbed to, the biocompatible coating. In various embodiments, the biocompatible coating disclosed herein may absorb at least 25%, at least 50%, or at least 75% amount of biomolecule by total weight of the biocompatible coating. In other embodiments, at least 25%, at least 50%, at least 75%, at least 100% of the outer surface of the biocompatible coating comprises attached biomolecules.

In some aspects, biomolecules may be one or more of the biomolecules disclosed herein. In an aspect, a biomolecule suitable for photothermal therapy agents disclosed herein may be an antibody, a peptide, a protein, an enzyme, an amino acid, a nucleic acid, a carbohydrate, a fat, an aptamer, a small molecule, a synthetic molecule or a combination thereof. In preferred aspects, a biomolecule suitable for photothermal therapy agents disclosed herein is a peptide or a nucleic acid.

In other embodiments, photothermal therapy agents disclosed herein may further comprise an imaging agent. In some aspects, an imaging agent may be one or more of the imaging agents disclosed herein. In a preferred aspect, an imaging agent for use in photothermal therapy agents disclosed herein may be a fluorescein compound, a rhodamine compound, a xanthene compound, a cyanine compound, a naphthalene compound, a coumarin compound, an oxadiazole compound, a pyrene compound, an oxazine compound, an acridine compound, an arylmethine compound, a tetrapyrrole compound, a proprietary molecule, or a combination thereof.

In various embodiments, a photothermal therapy agent as disclosed herein can be stable. As used herein, a photothermal therapy agent is considered to be "stable" when the neither the heating ability nor the hydrodynamic diameter of particles comprising the composition have changed from baseline measurements.

In some embodiments, a photothermal therapy agent disclosed herein can be stable from about 20° C. to about 120° C. In an aspect, a photothermal therapy agent can be stable at no less than about 20° C., about 40° C., about 60° C., about 80° C., about 100° C., or about 120° C. In another aspect, a photothermal therapy agent can be stable no less than about 80° C.

In other embodiments, a photothermal therapy agent disclosed herein can be stable from about 3 days to about 14 days. In an aspect, a photothermal therapy agent can be stable for about 3 days, about 5 days, about 7 days, about 10 days, about 12 days, or about 14 days. In another aspect, a photothermal therapy agent can be stable for about 7 days.

In some embodiments, one or more biofunctionalized nanocomposites as disclosed herein may be an active ingredient in a photothermal therapy agent composition. In an aspect, biofunctionalized nanocomposites disclosed herein may comprise about 0.1 to about 99% by weight in a photothermal therapy agent composition. In other aspects, biofunctionalized nanocomposites disclosed herein may comprise at least 10%, at least 25%, at least 50%, at least 75%, at least 99% by weight in a photothermal therapy agent composition.

In various embodiments, a photothermal therapy agent composition may be in a dosage-form suitable for administration to a subject in need thereof. Non-limiting examples of dosage-forms are tablets, granules, solutions, dispersions, emulsions, capsules, or suspensions.

In various embodiments, a photothermal therapy agent composition may further comprise one or more excipients. In an aspect, excipients suitable for use in a photothermal therapy agent composition disclosed herein may be carriers, diluents, buffers, stabilizers, an anti-oxidant, colorants, other medicinal or pharmaceutical agents, adjuvants, preserving agents, stabilizing agents, wetting agents, emulsifying agents, solution promoters, salts, solubilizers, antifoaming agents, antioxidants, dispersing agents, surfactants, or combinations thereof. In some aspects, a photothermal therapy agent composition may comprise one or more excipients at about 0.1 to about 99% by weight in the photothermal therapy agent composition. In other aspects, excipients may comprise at least 10%, at least 25%, at least 50%, at least 75%, at least 99% by weight in the photothermal therapy agent composition.

(II) Uses of Compositions

In various embodiments, compositions disclosed herein may be effective for treating at least one tumor cell following administration to a subject in need. In other embodiments, compositions disclosed herein may be effective for preventing metastasis of at least one tumor cell following administration to a subject in need. In other embodiments, compositions disclosed herein may be effective for treating and/or preventing cancer following administration to a subject in need.

A suitable subject includes a human, a livestock animal, a companion animal, a lab animal, or a zoological animal. In one embodiment, the subject may be a rodent, e.g., a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

In various embodiments, a subject in need may have been diagnosed with cancer. In one aspect, the subject may have cancer at any stage of disease progression. In one embodiment, a subject may have Stage I-IV cancer. In another embodiment, a subject may have Stage I-III cancer. In another embodiment, a subject may have Stage I-II cancer. In another embodiment, a subject may have Stage I cancer. In another embodiment, the cancer may be a primary cancer, a metastases, or primary cancer and metastases. In yet another embodiment, the cancer may be a solid cancer. In still another embodiment, the cancer may be a liquid cancer. Non-limiting examples of cancer types include carcinomas, sarcomas, lymphomas, leukemias, myelomas and mixed types (e.g., blastomas). In some embodiments, a subject in need may have been diagnosed with neuroblastoma.

In another embodiment, subject present with one or more cancerous solid tumors, metastatic nodes, of a combination thereof. In one embodiment, a subject may have a cancerous tumor cell source that may be less than about 0.2 cm3 to at least about 20 cm3 or greater, at least about 2 cm3 to at least about 18 cm3 or greater, at least about 3 cm3 to at least about 15 cm3 or greater, at least about 4 cm3 to at least about 12 cm3 or greater, at least about 5 cm3 to at least about 10 cm3 or greater, or at least about 6 cm3 to at least about 8 cm3 or greater.

In various embodiments, the compositions disclosed herein may be effective for treating at least one tumor cell from a subject in need. In some embodiments, the amount of viable tumor cells is reduced by at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome.

In various embodiments, the compositions disclosed herein may reduce the amount of viable tumor cells by at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome.

In various embodiments, the compositions disclosed herein may prevent metastasis of at least one tumor cell in a subject in need. In some embodiments, the rate of metastasis or at least one tumor cell is reduced by at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome.

In various embodiments, compositions disclosed herein may treat and/or prevent cancer in a subject in need. In some embodiments, compositions disclosed herein may impair tumor growth compared to tumor growth in an untreated subject with identical disease condition and predicted outcome. In one embodiment, tumor growth may be stopped following treatment with compositions disclosed herein. In other embodiments, tumor growth may be impaired at least about 5% or greater to at least about 100%, at least about 10% or greater to at least about 95% or greater, at least about 20% or greater to at least about 80% or greater, at least about 40% or greater to at least about 60% or greater compared to an untreated subject with identical disease condition and predicted outcome. In other words, tumors in subject treated using a composition of the disclosure have tumors that grow at least 5% less (or more as described above) when compared to an untreated subject with identical disease condition and predicted outcome. In some embodiments, tumor growth may be impaired at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome. In additional embodiments, tumor growth may be impaired at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated subject with identical disease condition and predicted outcome.

In some aspects, treatment of tumors with compositions disclosed herein may result in a shrinking of a tumor in comparison to the starting size of the tumor. In this aspect, tumor shrinking is at least about 5% or greater to at least about 10% or greater, at least about 10% or greater to at least about 15% or greater, at least about 15% or greater to at least about 20% or greater, at least about 20% or greater to at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% (meaning that the tumor is completely gone after treatment) compared to the starting size of the tumor.

Compositions disclosed herein may decrease the presence of tumor markers compared to the presence of tumor markers in an untreated subject with identical disease condition and predicted outcome. As used herein "tumor markers" are defined as substances produced by cancer or by other cells of the body in response to cancerous conditions. Non-limiting examples of tumor markers include alpha-fetoprotein, beta-2-microglobulin, beta-human chorionic gonadotropin, BCR-ABL fusion gene, CA19-9, CD20, HE4, lactate dehydrogenase, prostate-specific antigen, and various others. In one embodiment, the presence of tumor markers may be ablated following treatment with the compositions disclosed herein. In other embodiments, the presence of tumor markers may be decreased at least about 5% or greater to at least about 100%, at least about 10% or greater to at least about 95% or greater, at least about 20% or greater to at least about 80% or greater, at least about 40% or greater to at least about 60% or greater compared to an untreated subject with identical disease condition and predicted outcome. In some embodiments, the presence of tumor markers may be decreased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome. In additional embodiments, the presence of tumor markers may be decreased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated subject with identical disease condition and predicted outcome.

In various embodiments, compositions disclosed herein may improve cancer life expectancy compared to the cancer life expectancy of an untreated subject with identical disease condition and predicted outcome. As used herein, "cancer life expectancy" is defined as the time at which 50 percent of subjects are alive and 50 percent have passed away. In an aspect, cancer life expectancy may be indefinite following treatment with a composition disclosed herein. In other aspects, cancer life expectancy may be increased at least about 5% or greater to at least about 100%, at least about 10% or greater to at least about 95% or greater, at least about 20% or greater to at least about 80% or greater, at least about 40% or greater to at least about 60% or greater compared to an untreated subject with identical disease condition and predicted outcome. In some aspects, cancer life expectancy may be increased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome. In additional aspects, cancer life expectancy may be increased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with identical disease condition and predicted outcome.

(III) Methods of Using Compositions

Other embodiments of the present disclosure are methods of administering compositions disclosed herein to a subject in need wherein administration treats at least one tumor cell. Still other embodiments of the present disclosure are methods of administering compositions disclosed herein to a subject in need wherein administration prevents metastasis of at least one tumor cell. Other embodiments of the present disclosure are methods of administering compositions disclosed herein to a subject in need wherein administration treats and/or prevents cancer.

(a) Methods of Administration

In various embodiments, compositions disclosed herein may be administered by parenteral administration. As used herein, "by parenteral administration" refers to administration of the compositions disclosed herein via a route other than through the digestive tract. In some embodiments, compositions disclosed herein may be administered by parenteral injection. In an aspect, administration of the disclosed compositions by parenteral injection may be by subcutaneous, intramuscular, intravenous, intraperitoneal, intracardiac, intraarticular, or intracavernous injection. In other aspects, administration of the disclosed compositions by parenteral injection may be by slow or bolus methods as known in the field. In some embodiments, the route of administration by parenteral injection can be determined by the target location. In an aspect, compositions disclosed herein may be administered through epidural, intacereblar, intracerebroventicular, epicutaneous, intradermal, subcutaneous, nasal, intravenous, intraarterial, intramuscular, intracardiac, intraosseus, intrathecal, introsynovial, intraperitoneal, intravesical, intravitreal, intra-articular, intracavernous, intravaginal, intrauterine, transdermal, or transmucosal routes.

In other embodiments, compositions disclosed herein may be administered orally. In an aspect, oral administration may be by tablets, capsules, powders, granules, solutions, emulsion, or suspensions comprising the disclosed compositions.

In an aspect, the dose of compositions disclosed herein to be administered are not particularly limited, and may be appropriately chosen depending on conditions such as a purpose of preventive and/or therapeutic treatment, a type of a disease, the body weight or age of a subject, severity of a disease and the like. In various embodiments, administration of a dose of a composition disclosed herein may comprise a therapeutically effective amount of the composition disclosed herein. As used herein, the term "therapeutically effective" refers to an amount of administered composition that reduces the amount of viable tumor cells, reduces the rate of metastasis, impairs tumor growth, shrinks tumor size, decreases the presence of at least one tumor marker, improve cancer life expectancy, or a combination thereof. A therapeutically effective amount of a composition disclosed herein to be delivered to a subject may be an amount that does not result in undesirable systemic side effects. In various embodiments, compositions administered as disclosed herein may comprise about 5% to about 95%, about 15% to about 85%, or about 25% to about 75% total biofunctionalized nanocomposite by total weight of the composition. In other embodiments, compositions administered as disclosed herein may comprise about 5% to about 95%, about 15% to about 85%, or about 25% to about 75% total photothermal therapy agent by total weight of the composition. In still other embodiments, photothermal therapy agent compositions administered as disclosed herein may comprise about 5% to about 95%, about 15% to about 85%, or about 25% to about 75% total biofunctionalized nanocomposite by total weight of the composition.

(b) Frequency of Administration

In some embodiments, a composition disclosed herein may be administered to a subject in need thereof once. In some embodiments, a composition disclosed herein may be administered to a subject in need thereof more than once. In some embodiments, a first administration of a composition disclosed herein may be followed by a second administration of a composition disclosed herein. In some embodiments, a first administration of a composition disclosed herein may be followed by a second and third administration of a composition disclosed herein. In some embodiments, a first administration of a composition disclosed herein may be followed by a second, third, and fourth administration of a composition disclosed herein. In some embodiments, a first administration of a composition disclosed herein may be followed by a second, third, fourth, and fifth administration of a composition disclosed herein.

The number of times a composition may be administered to an subject in need thereof can depend on the discretion of a medical professional, the disorder, the severity of the disorder, and the subject's response to the formulation. In some embodiments, a composition disclosed herein may be administered once to a subject in need thereof with a mild acute condition, for example a subject with Stage I-II cancer. In some embodiments, a composition disclosed herein may be administered more than once to a subject in need thereof with a moderate or severe acute condition, for example a subject with Stage I-IV cancer. In some embodiments, a composition disclosed herein may be administered continuously; alternatively, the dose of drug being administered may be temporarily reduced or temporarily suspended for a certain length of time (i.e., a "drug holiday"). In an aspect, the length of the drug holiday can vary between 2 days and 1 year, including by way of example only, 2 days, 1 week, 1 month, 6 months, and 1 year. In another aspect, dose reduction during a drug holiday may be from 10%-100%, including by way of example only 10%, 25%, 50%, 75%, and 100%.

In an aspect, the desired daily dose of compositions disclosed herein may be presented in a single dose or as divided doses administered simultaneously (or over a short period of time) or at appropriate intervals. In various embodiments, administration of a composition disclosed herein may be administered to a subject about once a day, about twice a day, about three times a day. In other embodiments, administration of a composition disclosed herein may be administered to a subject at least once a day, at least once a day for about 2 days, at least once a day for about 3 days, at least once a day for about 4 days, at least once a day for about 5 days, at least once a day for about 6 days, at least once a day for about 1 week, at least once a day for about 2 weeks, at least once a day for about 3 weeks, at least once a day for about 4 weeks, at least once a day for about 8 weeks, at least once a day for about 12 weeks, at least once a day for about 16 weeks, at least once a day for about 24 weeks, at least once a day for about 52 weeks and thereafter. In a preferred embodiment, administration of a composition disclosed herein may be administered to a subject once a day for at about 4 weeks.

In other embodiments, administration of a composition disclosed herein may be administered to a subject at least once a week, at least once a week for about 2 weeks, at least once a week for about 3 weeks, at least once a week for about 4 weeks, at least once a week for about 8 weeks, at least once a week for about 12 weeks, at least once a week for about 16 weeks, at least once a week for about 24 weeks, at least once a week for about 52 weeks and thereafter. In a preferred embodiment, administration of a composition disclosed herein may be administered to a subject once a week for at about 12 weeks.

In various embodiments, the amount and/or frequency of compositions disclosed herein administered can be adjusted based upon factors such as the particular compound, disease condition and its severity, according to the particular circumstances surrounding the case, including, e.g., the route of administration, the condition being treated, the target area being treated, and the subject or host being treated.

In some embodiments, a composition as disclosed may be initially administered followed by a subsequent administration of one for more different compositions or treatment regimens. In other embodiments, a composition as disclosed may be administered after administration of one for more different compositions or treatment regimens.

(c) Photothermal Therapy

In various embodiments, the compositions disclosed herein may be used in photothermal therapy. As used herein, "photothermal therapy" is a method of accumulating a material generating heat by absorbing light in a location requiring hyperthermal therapy and irradiating light. Herein, the general principles underlying photothermal treatment generally known by those skilled in the art are employed.

In various embodiments, administration of compositions disclosed herein to a subject in need may be effective for treating at least one tumor cell when used in photothermal therapy compared to an untreated subject with identical disease condition and predicted outcome. In other embodiments, administration of compositions disclosed herein to a subject in need may be effective for preventing metastasis of at least one tumor cell when used in photothermal therapy compared to an untreated subject with identical disease condition and predicted outcome. In other embodiments, administration of compositions disclosed herein to a subject in need may be effective for treating and/or preventing cancer when used in photothermal therapy compared to an untreated subject with identical disease condition and predicted outcome.

In an embodiment, performing photothermal therapy with a composition disclosed herein on a subject in need may result in cell and/or tissue death compared to an untreated subject with identical disease condition and predicted outcome. In an aspect, performing photothermal therapy with a composition disclosed herein on a subject in need may result in tumor tissue death but not surrounding, healthy tissue death compared to an untreated subject with identical disease condition and predicted outcome. In another aspect, about 10%, about 25%, about 50%, about 75%, about 100% of the tumor tissue is killed by photothermal therapy with a composition disclosed herein whereas surrounding, healthy tissue is not killed. In still another aspect, about 10%, about 25%, about 50%, about 75%, about 100% of the tumor tissue is killed by photothermal therapy with a composition disclosed herein whereas about 5%, about 10%, about 25% of surrounding, healthy tissue is killed.

In yet another embodiment, performing photothermal therapy on a subject in need with a composition disclosed herein may result in a cellular and/or tissue immune response compared to an untreated subject with identical disease condition and predicted outcome. As used herein, the term "immune response" refers to a measurable response to an antigen mediated by one or more cells of the immune system as a result of photothermal therapy. In an aspect, an immune response can include a humoral or cellular response. As used herein, an immune response to a tumor cell antigen refers to a measurable immune response to at least one antigen expressed on a tumor cell as a result of photothermal therapy. Similarly, an immune response to a tumor cell refers to an immune response that is detectable and specific for a tumor cell following administration of photothermal therapy. In some embodiments, performing photothermal therapy on a subject in need with a composition disclosed herein may result in at least a 2-fold, at least a 5-fold, at least a 10-fold, at least a 20-fold, at least a 50-fold increase in cellular and/or tissue immune response compared to an untreated subject with identical disease condition and predicted outcome.

In another embodiment, performing photothermal therapy on a subject in need with a composition disclosed herein may result in a cellular and/or tissue cytotoxic T lymphocyte response compared to an untreated subject with identical disease condition and predicted outcome. As used herein, a "cytotoxic T lymphocyte response" or "CTL response" refers to an immune response in which cytotoxic T cells are activated by photothermal therapy. A CTL response can include the activation of precursor CTLs as well as differentiated CTLs. In an aspect, a CTL response may include any measurable CTL response for at least one CTL that is specific for an antigen expressed on an autologous tumor cell. In some embodiments, performing photothermal therapy on a subject in need with a composition disclosed herein may result in an increased the frequency of precursor CTLs specific for tumor antigens compared to an untreated subject with identical disease condition and predicted outcome. In an aspect, performing photothermal therapy on a subject in need with a composition disclosed herein may increase the frequency of precursor CTLs specific for tumor antigens by at least 2-fold, at least 5-fold, at least 10-fold, at least 20-fold, at least 50-fold compared to an untreated subject with identical disease condition and predicted outcome. In some embodiments, performing photothermal therapy on a subject in need with a composition disclosed herein may stimulate the frequency of CTLs for tumor cells compared to an untreated subject with identical disease condition and predicted outcome. In an aspect, performing photothermal therapy on a subject in need with a composition disclosed herein may stimulate the frequency of CTLs for tumor cells by at least 2-fold, at least 5-fold, at least 10-fold, at least 20-fold, at least 50-fold compared to an untreated subject with identical disease condition and predicted outcome.

In another embodiment, performing photothermal therapy on a subject in need with a composition disclosed herein may result in T cell proliferation compared to an untreated subject with identical disease condition and predicted outcome. In an aspect, performing photothermal therapy on a subject in need with a composition disclosed herein may increase T cell proliferation by at least 50%, at least 60%, at least 70%, at least 80%, or at least 90% compared to an untreated subject with identical disease condition and predicted outcome.

In another embodiment, performing photothermal therapy on a subject in need with a composition disclosed herein may result in activation of dendritic cells (DCs) compared to an untreated subject with identical disease condition and predicted outcome. DC activation may be measured by detecting an increase in at least one DC surface activation marker using methods known in the art. In a preferred aspect, detection of DC surface activation markers is measured by flow cytometry. Non-limiting examples of DC surface activation markers include CD86, CD80, and CD40. In an aspect, performing photothermal therapy on a subject in need with a composition disclosed herein may activate D='s by at least 50%, at least 60%, at least 70%, at least 80%, or at least 90% compared to an untreated subject with identical disease condition and predicted outcome. In another aspect, performing photothermal therapy on a subject in need with a composition disclosed herein may increase detection of at least one DC surface activation marker by at least 50%, at least 60%, at least 70%, at least 80%, or at least 90% compared to an untreated subject with identical disease condition and predicted outcome. In still another aspect, performing photothermal therapy on a subject in need with a composition disclosed herein may increase detection of CD86, CD80, and CD40 by at least 50%, at least 60%, at least 70%, at least 80%, or at least 90% compared to an untreated subject with identical disease condition and predicted outcome.

In various embodiments, compositions described herein may be administered to a subject in need for a period of time before administering photothermal therapy. In an aspect, the time period may be dependent on the route of administration, target tissue, subject weight, timing of subject's food intake and the like. In another aspect, an orally administered composition disclosed herein may be administered about 12 hours to about 48 hours before photothermal therapy. In another aspect, a composition disclosed herein may be administered by parenteral injection about 1 hour to about 5 hours before photothermal therapy.

In various aspects, photothermal therapy may use a light source to irradiate compositions disclosed herein. In some embodiments, a composition disclosed herein may absorb near infrared radiation (NIR) delivered thereto, thus becoming irradiated. Devices and methods for delivering radiation of a particular wavelength include, but not limited to, lasers well-known and standard in the art. In an aspect, the amount of light delivered to a tissue may be determined based on the physical dimensions and thermal characteristics of the tissue to be treated, such that the absorption of said light leads to the desired temperature increase in the tissue. In some embodiments, a method of administering compositions disclosed herein for use in photothermal therapy further comprises calculating output power of the laser based at least in part upon one of heat dissipation and conductivity values within the tissue or shape factor values of the tissue and/or determining time of exposure of the laser. In an aspect, the heat energy can cause cellular death of a plurality of cells of the tumor. In various embodiments, the light wavelength is in a range of about 600 to about 1000 nm. In a preferred aspect, the light wavelength is 800 nm.

In various embodiments, compositions disclosed herein may be irradiated after exposure to a light source for about 4 minutes to 20 minutes. In other embodiments, compositions disclosed herein may be irradiated after exposure to a light source for about 4 minutes, about 6 minutes, about 8 minutes, about 10 minutes, about 12 minutes, about 14 minutes, about 16 minutes, about 18 minutes, or about 18 minutes. In a preferred embodiment, compositions disclosed herein may be irradiated after exposure to NIR for about 10 minutes.

In various embodiments, a method of irradiating compositions disclosed herein by administering photothermal therapy can result in a thermal interaction at the site of the targeted cell and/or tissue. In an aspect, a thermal interaction may increase temperatures of the targeted cell and/or tissue to at least 40° C., at least 41° C., at least 42° C., at least 43° C., or at least 44° C. In another aspect, a thermal interaction may increase temperatures of the targeted cell and/or tissue to stimulate cell and/or tissue death. In yet another aspect, a thermal interaction may increase temperatures of the targeted cell and/or tissue to stimulate cell and/or tissue immune response. In still another aspect, a thermal interaction may increase temperatures of the targeted cell and/or tissue to stimulate cell and/or tissue damage-associated molecular patterns (DAMPs). As used herein, "DAMPs" refers to host biomolecules that can initiate and perpetuate a noninfectious inflammatory response to trauma, ischemia, and/or tissue damage. In an aspect, DAMPs may be a protein, a non-protein biomolecule, or a combination thereof. Non-limiting examples DAMPs proteins include S100 proteins, heat-shock proteins (HSP), calreticulin, HMGB1 (high-mobility group box 1), and hyaluronan fragments. Non-limiting examples of non-protein DAMPs include ATP, uric acid, heparin sulfate, hyaluronic acid, RNA, and DNA. In another aspect, a thermal interaction may increase temperatures of the targeted cell and/or tissue to stimulate cell and/or tissue pathogen-associated molecular patterns (PAMPs). As used herein, "PAMPs" refers to biomolecules that initiate and perpetuate an inflammatory response and promote signals associated with innate immunity. Non-limiting examples of PAMPs include DNA (e.g. unmethylated CpG motifs), double-stranded RNA (dsRNA), single-stranded RNA (ssRNA), and 5'-triphosphate RNA, lipoproteins, surface glycoproteins, peptidoglycans, lipoteichoic acid, lipopolysaccharide (LPS), and glycosylphosphatidylinositol.

In various embodiments, a method of irradiating compositions disclosed herein by administering photothermal therapy may reduce the amount of viable tumor cells by at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome.

In various embodiments, a method of irradiating compositions disclosed herein by administering photothermal therapy may prevent metastasis of at least one tumor cell in a subject in need. In some embodiments, the rate of metastasis or at least one tumor cell is reduced by at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome.

In various embodiments, a method of irradiating compositions disclosed herein by administering photothermal therapy may treat and/or prevent cancer in a subject in need. In some embodiments, a method of irradiating compositions disclosed herein by administering photothermal therapy may impair tumor growth compared to tumor growth in an untreated subject with identical disease condition and predicted outcome. In one embodiment, tumor growth may be stopped following photothermal therapy with compositions disclosed herein. In other embodiments, tumor growth may be impaired at least about 5% or greater to at least about 100%, at least about 10% or greater to at least about 95% or greater, at least about 20% or greater to at least about 80% or greater, at least about 40% or greater to at least about 60% or greater compared to an untreated subject with identical disease condition and predicted outcome. In other words, tumors in subject treated with photothermal therapy using a composition of the disclosure may have tumors that grow at least 5% less (or more as described above) when compared to an untreated subject with identical disease condition and predicted outcome. In some embodiments, tumor growth may be impaired at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome. In additional embodiments, tumor growth may be impaired at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated subject with identical disease condition and predicted outcome.

In some aspects, treatment of tumors with photothermal therapy using compositions disclosed herein may result in shrinking of a tumor in comparison to the starting size of the tumor. In this aspect, tumor shrinking can be at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% (meaning that the tumor is completely gone after treatment) compared to the starting size of the tumor.

In other embodiments, administration of photothermal therapy using compositions disclosed herein may decrease the presence of tumor markers compared to the presence of tumor markers in an untreated subject with identical disease condition and predicted outcome. In one embodiment, the presence of tumor markers may be ablated following photothermal therapy with the compositions disclosed herein. In other embodiments, the presence of tumor markers may be decreased at least about 5% or greater to at least about 100%, at least about 10% or greater to at least about 95% or greater, at least about 20% or greater to at least about 80% or greater, at least about 40% or greater to at least about 60% or greater compared to an untreated subject with identical disease condition and predicted outcome. In some embodiments, the presence of tumor markers may be decreased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome. In additional embodiments, the presence of tumor markers may be decreased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated subject with identical disease condition and predicted outcome.

In various embodiments, administration of photothermal therapy using compositions disclosed herein may improve cancer life expectancy compared to the cancer life expectancy of an untreated subject with identical disease condition and predicted outcome. In an aspect, cancer life expectancy may be indefinite following photothermal therapy with a composition disclosed herein. In other aspects, cancer life expectancy may be increased at least about 5% or greater to at least about 100%, at least about 10% or greater to at least about 95% or greater, at least about 20% or greater to at least about 80% or greater, at least about 40% or greater to at least about 60% or greater compared to an untreated subject with identical disease condition and predicted outcome. In some aspects, cancer life expectancy may be increased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome. In additional aspects, cancer life expectancy may be increased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with identical disease condition and predicted outcome.

EXAMPLES

The following examples are included to demonstrate preferred embodiments of the disclosure. It should be appreciated by those of skill in the art that the techniques disclosed in the examples that follow represent techniques discovered by the inventors to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Introduction to Examples 1-9

Figure 1:
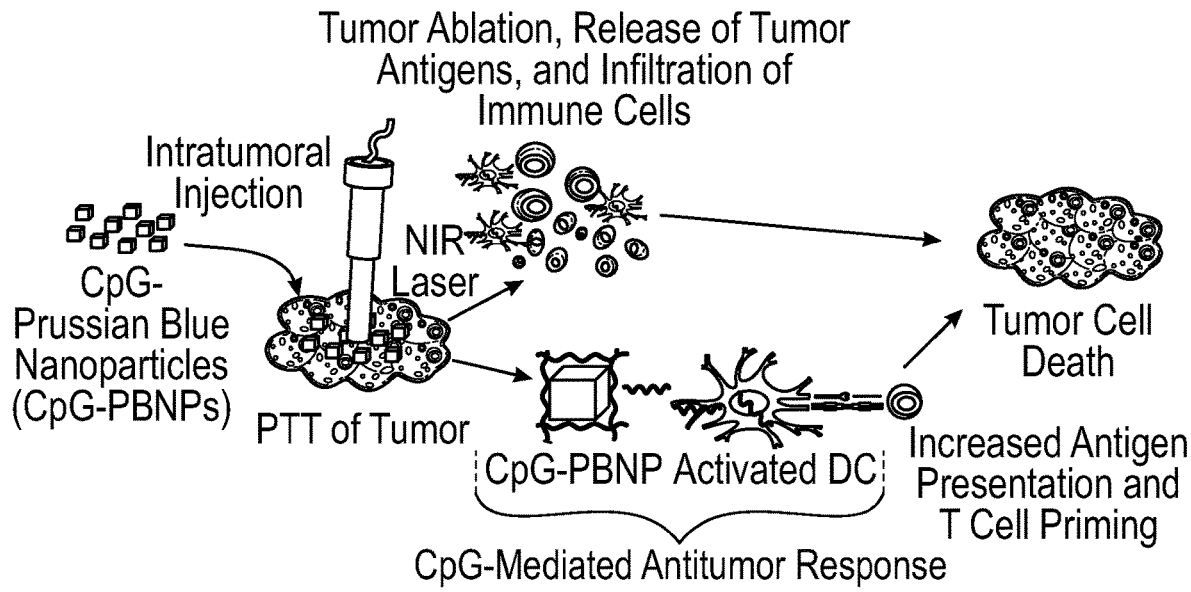
FIG. 1 depicts a schematic of a method of administering photothermal therapy to irradiate CpG-PBNPs nanoparticles in tumor cells to result in tumor cell death.

Prussian blue nanoparticle (PBNP)-based photothermal therapy (PTT) is a rapid and minimally invasive method for reducing tumor burden. Although PBNP-PTT provides a platform for cell destruction and an upregulation of an immune response, tumor cell responses are not complete after PBNP-PTT primarily because activation of T cells is compromised in subjects with cancers due to immune suppression, loss of antigen expression, and dysfunction of antigen presenting cells (APCs). As an example of how to overcome these drawbacks, described herein are PBNPs biofunctionalized with CpG, an exogenous immune adjuvant that plays an important role in breaking tolerance to tumor antigens and improving antigen presentation by stimulating PAMP-induced signal transduction pathways, which are impaired in immunosuppressive tumors. Description of the synthesis and characterization of CpG-PBNPs, studies to determine the effectiveness of CpG-PBNPs in photothermal therapy, and use of CpG-PBNPs in photothermal therapy for the treatment of tumor cells (FIG. 1) are outlined below.

Example 1

Figure 2A:
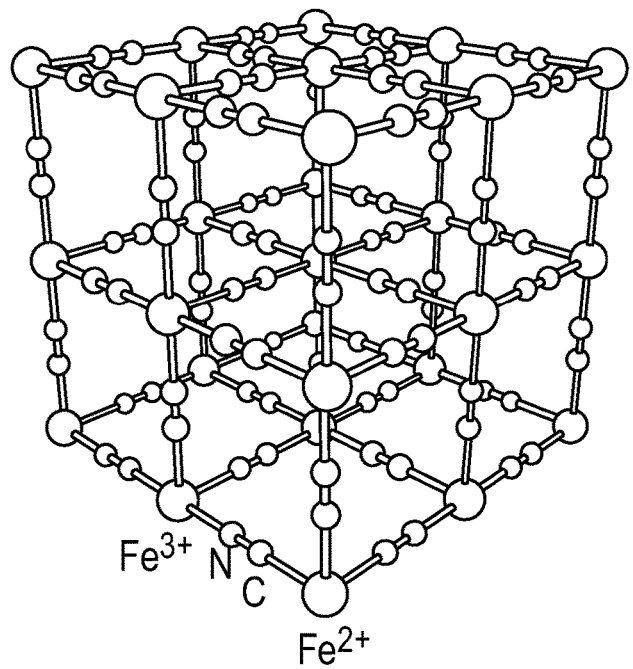
FIG. 2A depicts an image of a ball-and-stick representation of the iron(III) hexacyanoferrate(II) ($Fe_4[Fe(CN)_6]3$) cubic lattice crystal structure which constitutes a Prussian blue nanoparticle (PBNP).

To synthesize Prussian blue nanoparticles (PBNPs) as shown in FIG. 2A, an aqueous solution of 1.0 mM $FeCl_3 \cdot 6H_2O$ and 0.5 mmol citric acid in 20 mL of ultrapure water was added, under vigorous stirring, to an aqueous 20 mL solution containing 1 mM $K_4Fe(CN)_6 \cdot 3H_2O$ and 0.5 mmol citric acid at 60° C. After stirring for 1 minute, the solution was allowed to come to room temperature (23° C.±3° C.). The precipitate was isolated from the solution first by the addition of equal volumes of acetone followed by centrifugation at 10,000 revolutions per minute (rpm) for 10 minutes, and finally rinsed by sonication (5 seconds, high power) in ultrapure water. The isolation and rinsing steps were repeated three times before the particles were resuspended by sonication in ultrapure water. Note that all synthetic procedures were conducted using ultrapure water, or "grade 1" water as defined by the International Organization for Standardization (ISO), with resistivity of 18.2 MΩ·cm.

Figure 2B:
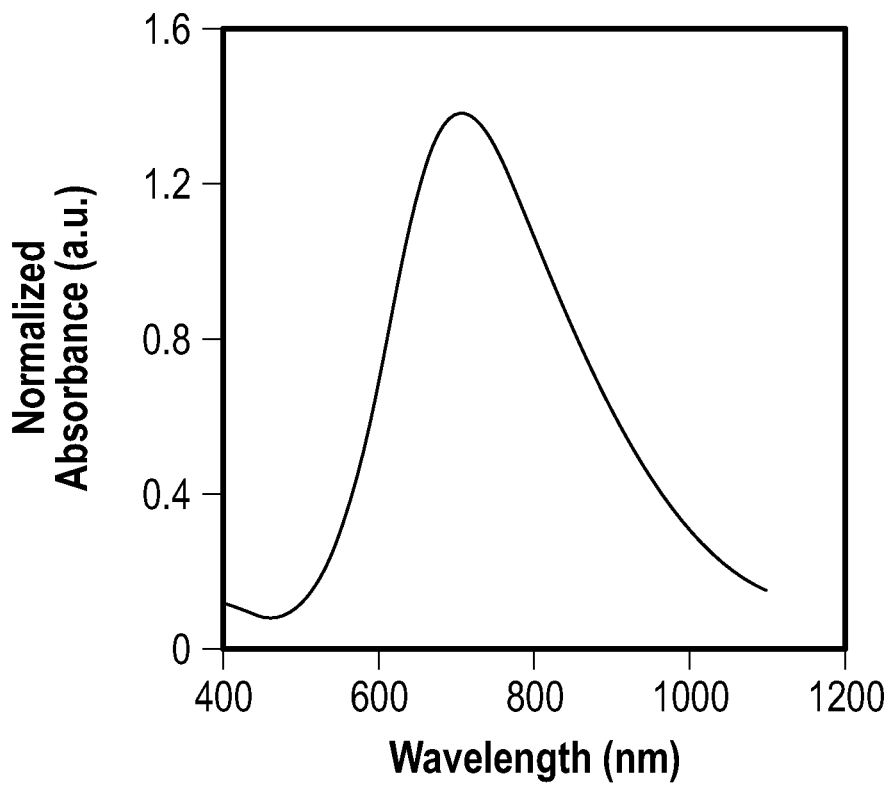
FIG. 2B depicts a graph showing the absorbance spectrum of PBNPs showed near infrared (NIR) absorbance from 650-900 nm ($\lambda_{max}$=705 nM).
Figure 2C:
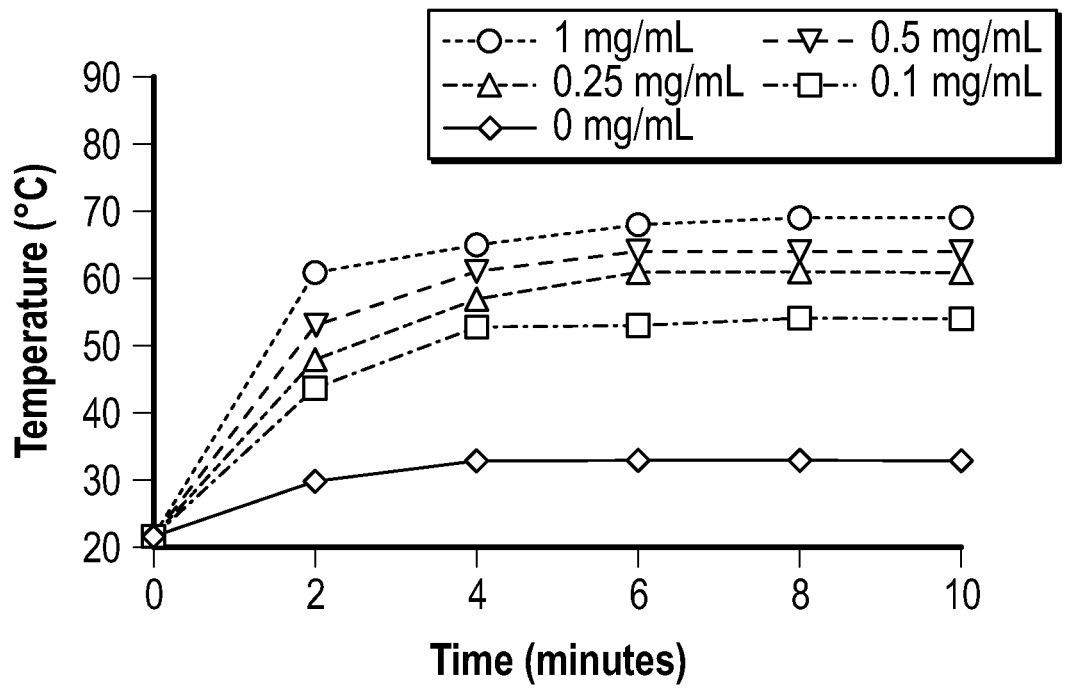
FIG. 2C depicts a graph showing the photothermal heating characteristics of PBNPs following photo-thermal heating of varying concentrations of PBNPs (0-1 mg/mL) irradiated by an 808 nm NIR laser for 10 minutes at 1.875 W $cm^2$ power.

The visible-near infrared (NIR) spectrum of 1 mg/mL PBNPs showed a characteristic absorption band from 650 to 900 nm, corresponding to the energy of the metal-to-metal charge transfer between $Fe^{2+}$ and $Fe^{3+}$ through the cyanide bridge (CN) (FIG. 2B). The photothermal heating characteristics of the synthesized PBNPs was tested over time by irradiating increasing conctrations of PBNPs (0 to 1 mg/mL) with an 808 nm NIR laser at 1.875 W cm$^2$ for 10 minutes. Results revealed that the synthesized PBNPs were suitable laser-induced photothermal therapy (PTT) agents where the photothermal heating effect was a function of PBNP concentration and was observed to increase with increasing PBNP concentrations (FIG. 2C). Having established these baseline characteristics, the synthesized PBNPs were deemed suitable to continued processing as detailed below.

The resulting PBNPs were surface coated using a layer-by-layer strategy by first suspending 2 mg of the PBNPs in 2 mL of 50 wt % polyethylenimine (PEI). Prior to this step, PEI (average MW=2000) was diluted with acetate buffer (pH 5.2) to a concentration of 50 wt %. Next, the PBNP suspension was shaken at room temperature (23° C.±3° C.) for 1 hour, and the PEI-coated PBNPs were subsequently collected by centrifugation at 10,000 rpm for 10 minutes with equal volumes of ethanol. After 4 washes with deionized water, the PEI-PBNPs were resuspended by sonication in Milli-Q water.

CpG oligodeoxynucleotides (CpG ODN) are short single-stranded synthetic DNA molecules containing an unmethylated deoxycytosine-deoxyguanosine (CpG) motif which can activate Toll-like receptor 9 (TLR9). CpG ODN 1585, a Class A CpG ODN specific for mouse TLR9, was the selected CpG ODN for coating PBNPs. To formulate the CpG-PBNPs, 300 μL of CpG ODN aqueous solution (containing 100 μg CpG) was added to 500 μL of the above PEI-PBNP suspension (at 2 mg/mL) while stirring at room temperature 23° C.±3° C.). The mixture was centrifuged at 15,000 rpm for 15 minutes to collect the resulting CpG-coated PBNPs. The CpG loading capacity on the PBNPs was calculated from the concentration of unloaded CpG oligodeoxynucleotide molecules in the supernatant using a full-spectrum, UV-Vis spectrophotometer.

To determine the multi-day release of CpG from PBNPs in a tumor environment (pH 5.5) and physiological environment (pH 8), solutions at pH 5.5, 7.0 or 8 were prepared by adding the appropriate amounts of mild acid or base to the CpG-PBNP suspensions (0.8 mg/mL) in Milli-Q water until the desired, stable pH was obtained. The amount of CpG released was measured using a full-spectrum, UV-Vis spectrophotometer.

Example 2

To guarantee that coating PBNPs with CpG does not affect the intrinsic characteristics of PBNPs, properties of CpG-PBNPs were measured and compared to PEI-PBNPs and uncoated PBNPs. The size (hydrodynamic diameter) and charge (zeta potential) distributions of uncoated PBNPs, PEI-PBNPs and CpG-PBNPs were measured using dynamic light scattering (DLS) on a Zetasizer Nano ZS (Malvern Instruments, Malvern, UK). The Vis-NIR absorbance of the nanoparticles were measured on the Genesys 10S spectrophotometer using the VISIONlite software.

Figure 3A:
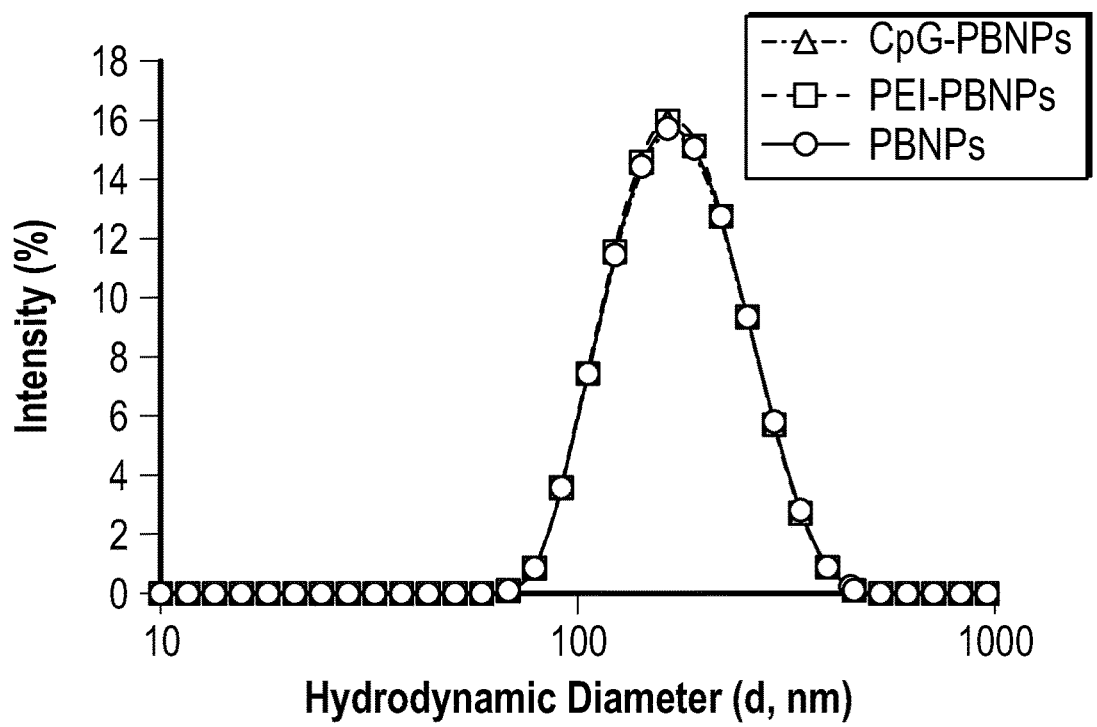
FIG. 3A depicts a graph showing the particle size distribution of uncoated PBNPs, PEI-PBNPs and CpG-PBNPs using dynamic light scattering (DLS).
Figure 3B:
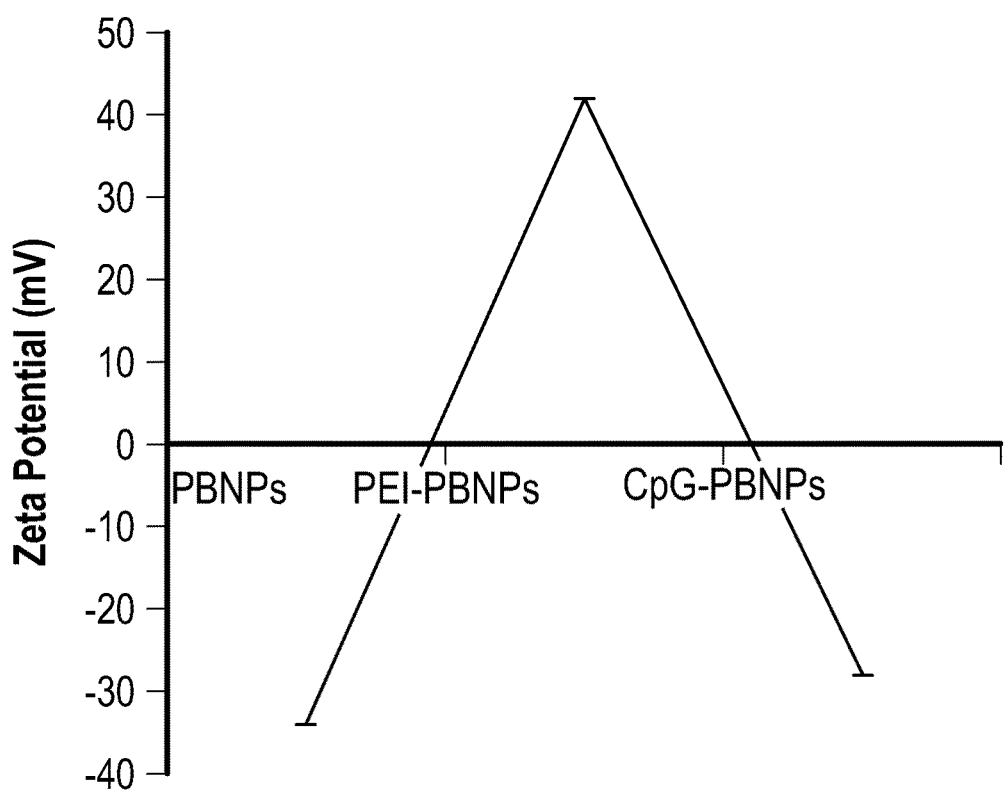
FIG. 3B depicts a graph showing the charge distribution of uncoated PBNPs, PEI-PBNPs and CpG-PBNPs by determining the zeta potential of each.
Figure 3C:
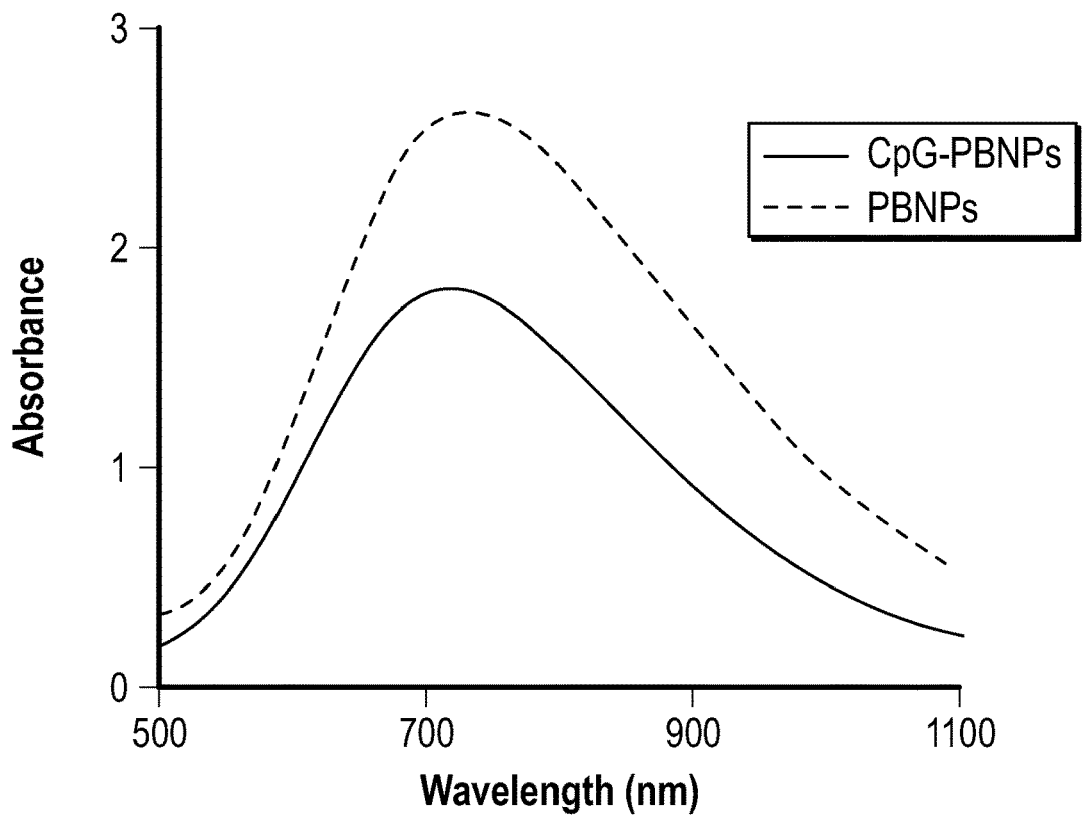
FIG. 3C depicts a graph showing the absorbance spectrum of uncoated PBNPs and CpG-PBNPs showed NIR absorbance from 650-900 nm ($\lambda_{max}$=705 nM).

CpG-PBNPs had similar size (average diameter 190 nm) to PEI-PBNPs and uncoated PBNPs (FIG. 3A), suggesting that the CpG coating does not affect the hydrodynamic diameter of the PBNPs. Confirmation that each layer is being coated onto the PBNPs can be determined by measuring the charge distributions (zeta potential) of these particles. PBNPs are intrinsically negatively charged (average zeta potential −34 mV), so the addition of positively charged PEI (Mw 2000) and negatively charged CpG changes the charge to positive (+42 mV) and then negative (−32 mV), respectively (FIG. 3B). The Vis-NIR spectrum of 1 mg/mL CpG-PBNPs demonstrated the characteristic absorption band from 650 to 900 nm=705 nm; FIG. 3C). This band corresponds to the energy of the metal-to-metal charge transfer between $Fe^{2+}$ and $Fe^{3+}$ through the cyanide bridge. Having a similar Vis-NIR spectrum indicates that the CpG-PBNPs will heat up in a similar manner to that of uncoated PBNPs.

Figure 3D:
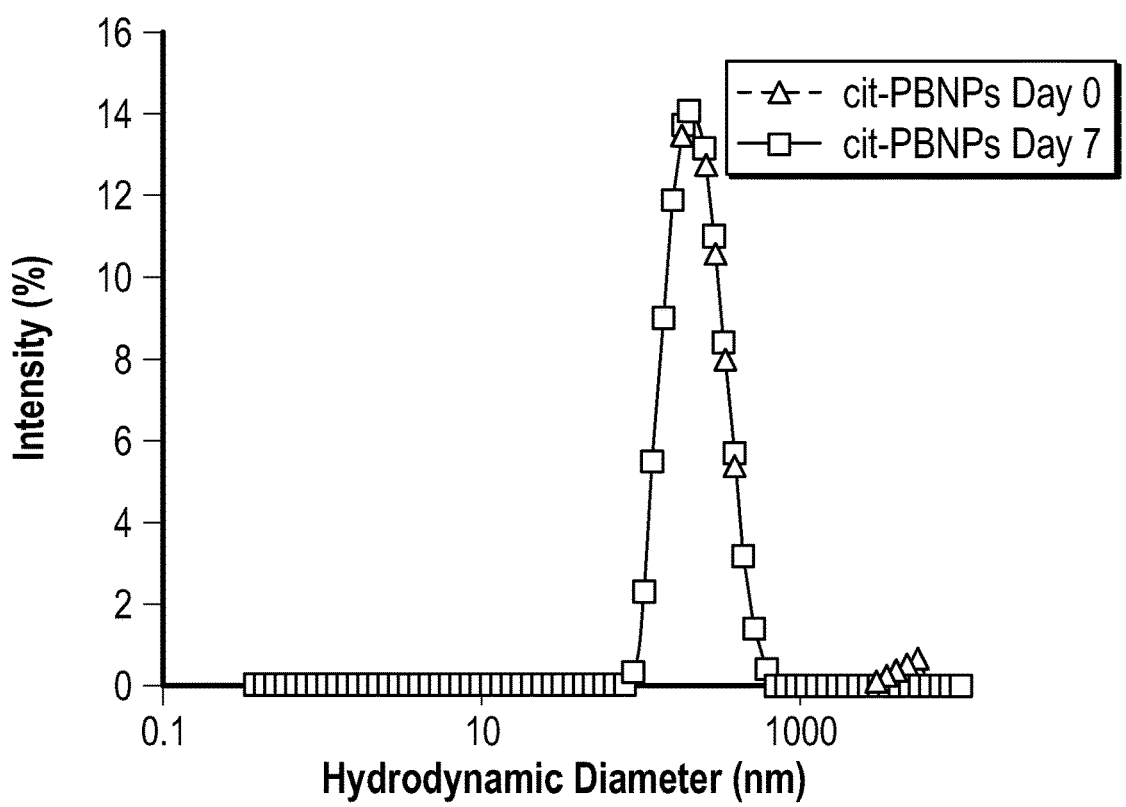
FIG. 3D depicts a graph showing the particle size distribution of uncoated PBNPs at day 0 and day 7 using temporal DLS.
Figure 3E:
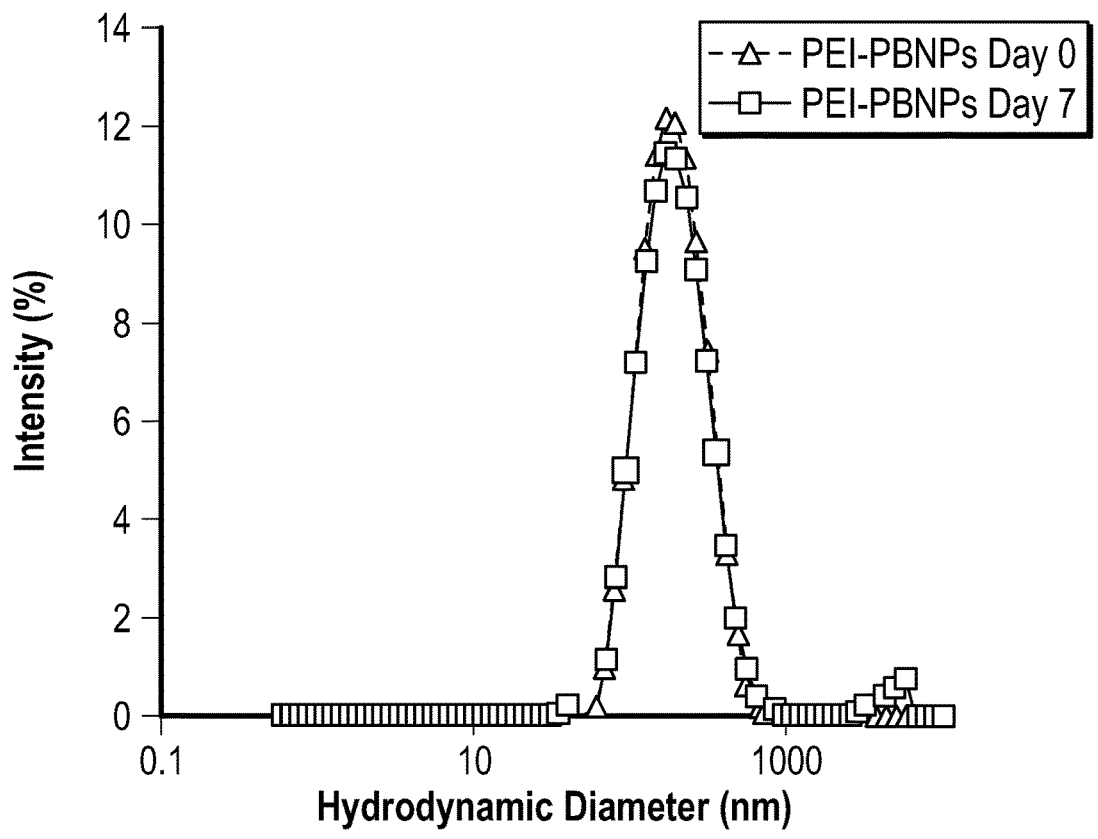
FIG. 3E depicts a graph showing the particle size distribution of PEI-PBNPs at day 0 and day 7 using temporal DLS.
Figure 3F:
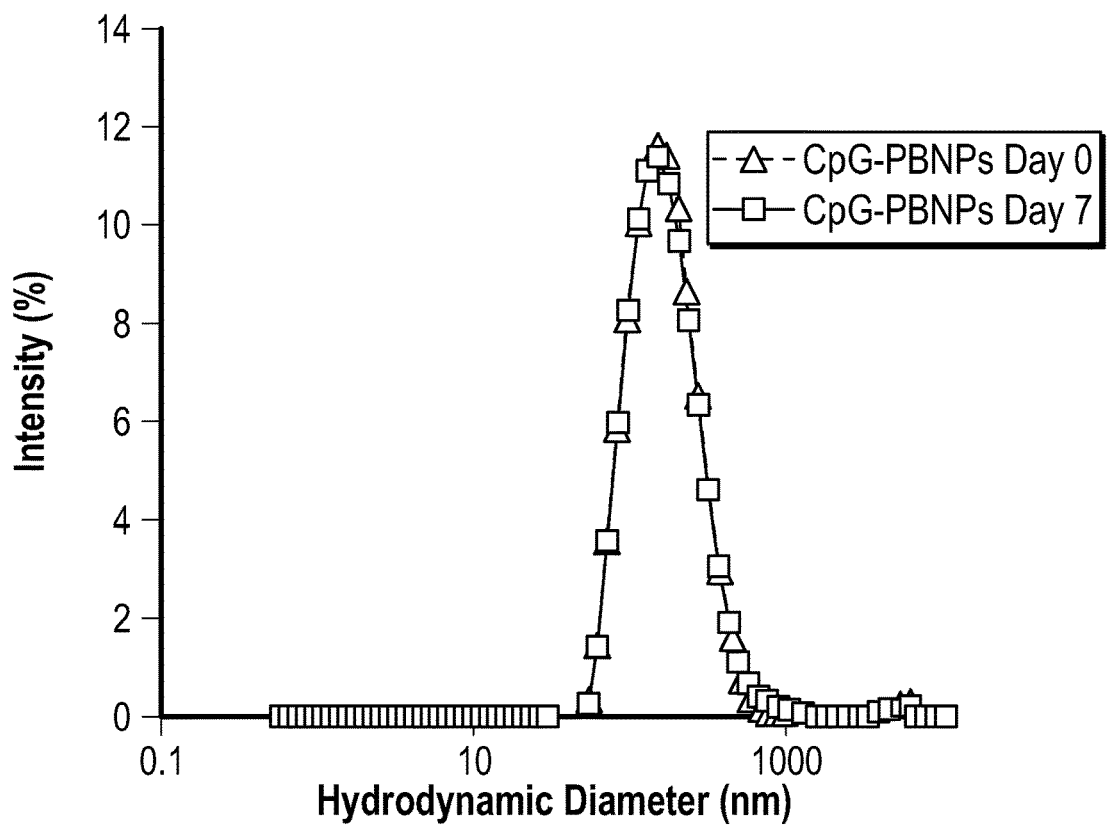
FIG. 3F depicts a graph showing the particle size distribution of CpG-PBNPs at day 0 and day 7 using temporal DLS.

Multiday stability of uncoated PBNPs, PEI-PBNPs and CpG-PBNPs in ultrapure water was assessed by measuring their hydrodynamic size distributions every 24 hours over 7 days using DLS, zeta potential, and UV-NIR absorbance. The uncoated PBNPs (FIG. 3D), PEI-PBNPs (FIG. 3E), and CpG-PBNPs (FIG. 3F) had a constant mean hydrodynamic diameter at each step of the synthesis for 7 days demonstrating that each of the particles were stable over time.

Example 3

The photothermal therapy (PIT) capabilities of CpG-PBNPs were tested in vitro (Neuro2a cells) as a function of concentration by varying the concentration of the nanoparticles from 0.025 mg/mL to 0.5 mg/mL at a fixed laser fluence (power density) of 0.75 W for 10 minutes. The PIT capabilities were also measured as a function of laser fluence (0.25 W-1.25 W) by irradiating CpG-PBNPs at a concentration of 1 mg/mL for 10 minutes. The stability of CpG-PBNPs as a photothermal agent was assessed by a cyclic heating/cooling study where 1 mg/mL CpG-PBNPs were irradiated by the NIR laser at 0.75 W (laser on/off times=10 minutes each). Power was confirmed by a power meter and temporal temperature measurements were taken using a thermal camera.

Photothermal heating of various concentrations of CpG-PBNPs irradiated by an 808 nm NIR laser for 10 minutes at 0.75 W/cm$^2$ laser power showed that temperatures increase with increasing CpG-PBNP concentrations (FIGS. 4A and 4B). The photothermal heating effect of 1 mg/mL CpG-PBNPs using varying NIR laser powers for 10 minutes was also dependent on the power of the incident laser, and was observed to increase with increasing laser powers (FIGS. 4C and 4D). Temperature profiles were asses during cyclic heating of 1 mg/mL CpG-PBNPs using an 808 nm NIR laser (laser on/off time: 10 minutes) to determine the stability of CpG-PBNPs as PTT agents. CpG-PBNPs showed consistent photothermal heating over four consecutive heating and cooling cycles indicating stability of the CpG-PBNPs as PTT agents (FIG. 4E). These results show that coating PBNPs with CpG does not affect the heating abilities, and that CpG-PBNPs can withstand the high temperatures required for, among other things, tumor ablation and upregulation of an immune response.

The extent of thermal damage to tissue depends on tissue sensitivity, temperature and exposure time. To clarify the threshold for thermal damage CpG-PBNPs may cause when used as a photothermal therapy agent, the thermal dose (CEM43° C.) was calculated using thermal histories from the above in vitro data. Specifically the time-temperature history is converted to an equivalent number of minutes of heating at 43° C., using the following formula:

$$CEM43° \text{ C.} = \sum_{i=1}^{n} t_i \cdot R^{(43-T_i)},$$

where the equivalent number of minutes of heating at 43° C. is a model to calculate a thermal isoeffect dose. The CEM43° C. thermal dose model for both uncoated PBNPs and CpG-PBNPs suggests that damage is greater at higher concentrations of the nanoparticles and CpG-PBNPs do not cause more or less damage than uncoated PBNPs (FIG. 4F).

Example 4

The amount of CpG encapsulated in the CpG-PBNPs was measured by UV-Vis spectrophotometry as known in the art under varying pH conditions. The release of CpG over time from the CpG-PBNPs was measured in either a mildly acidic solution (pH 4.6) to mimic tumor interstitium, MilliQ-water (pH 7), or a mildly alkaline solution (pH 8) to mimic a physiological environment. Timed measurements were performed at 0, 2, 4, and 8 days of incubation. CpG remained encapsulated at neutral pH for 8 days; however, while when in the mildly acidic solution (pH 4.6) and mildly alkaline solution (pH 8), the CpG was released from the nanoparticles, as seen by the decrease in CpG encapsulation (FIG. 5A). The decreased CpG encapsulation was possibly attributed to a degradation of the PBNPs at physiological pH, which was caused by an attack of the characteristic $Fe^{2+}$—CN—$Fe^{3+}$ bonds of PBNPs by a slight excess of hydroxyl ions. These findings suggest that when CpG-PBNPs are in the tumor intestitium and its surrounding physiological environments, the CpG will be released from the nanoparticles to interact with the immune system. Overall, the concentration of free CpG is 5-fold higher than encapsulated CpG (FIG. 5B), demonstrating the therapeutic encapsulation efficiently of CpG.

Example 5

Intrinsic cytotoxicity of uncoated PBNPs, PEI-PBNPs, and CpG-PBNPs was assessed in vitro using the murine neuroblastoma cell line Neuro2a. Neuro2a cells were seeded at a cell density of 50,000 cells per well, and incubated with either vehicle or varying concentrations of uncoated PBNPs, PEI-PBNPs, or CpG-PBNPs (0.001-0.5 mg/mL) for 24 hours. After the 24-hour incubation period, cell viability was assessed using a luminescent cell viability assay. Neuro2a cell viability was not significantly changed among treatment groups (FIG. 6). Taken together, the above data indicate that CpG-PBNPs can be synthesized, exhibit stability, and are non-toxic to cells.

Example 6

The effect of CpG-PBNPs on the toll-like receptor 9 (TLR9) pathway-mediated dendritic cell (DC) activation was assessed by measuring expression of common DC surface activation markers: CD86, CD80, and CD40. First, DCs were isolated from the spleens of naïve C57BL/6J mice using a CD11c$^+$ magnetic isolation kit. Cells were then plated ($1\times10^5$ cells/well) in Roswell Park Memorial Institute medium (RPMI 1640) supplemented with 10% fetal bovine serum, 2 mM L-glutamine, 55 µM β-mercaptoethanol, 1× non-essential amino acids, 10 mM HEPES (4-(2-hydroxyethyl)-1-piperazineethanesulfonic acid), and 1× Penicillin-Streptomycin (Pen/Strep). Samples, which were added in triplicate, included medium, lipopolysaccharide (LPS, 1 µg/mL), CpG (40, 10 and 1 µg/mL), uncoated PBNPs (1 mg/mL and 2×, 4×, 8×, 16×, 32×, 64×, and 128× dilutions thereof), and CpG-PBNPs (1 mg/mL PBNPs coated with 40 µg/mL CpG and 2×, 4×, 8×, 16×, 32×, 64×, and 128× dilutions thereof). Medium-treated DCs served as a negative control, while LPS and free CpG treatments were employed as positive controls. Cultures were incubated for 24 hours, then collected by centrifugation (800 g, 5 minutes), washed twice in fluorescence-activated cell sorting (FACS) buffer, and blocked with the antibodies anti-CD16/CD32. The cells were finally stained for 20 minutes at room temperature (23° C.±3° C.) using monoclonal antibodies against the surface activation markers CD40, C80, and CD86. After staining, cells were washed twice and resuspended in FACS buffer containing DAPI (4',6-diamidino-2-phenylindole) for analysis by flow cytometry. All flow cytometry data was conducted by using FlowJo software.

Flow cytometry analysis of DCs showed that the amount of live CD11c+ positive cells was consistent amount all treatment groups (FIG. 7A). Flow cytometry analysis of DCs also revealed that DCs were activated, as assessed by CD86+ mean fluorescence intensity (MFI) amount live cells (FIG. 7B). Analogous trends were observed for additional activation markers, CD80+ (FIG. 7B) and CD40+ (FIG. 7C). Together, these data indicate CpG-PBNP correlates with the level of DC activation given by free CpG. These findings demonstrate that CpG-PBNPs activate DCs as a result of the CpG coating on the particles.

Example 7

The effect of CpG-PBNPs on the toll-like receptor 9 (TLR9) pathway-mediated proliferation of CD8$^+$ T cells was assessed by flow cytometry. First, CD11c$^+$ DCs from naïve C57BL/6J mice were isolated and cultured as described in Example 6. After 48 hours of culture, naïve CD8$^+$ T cells were then isolated by magnetic separation from the spleens of TRP-2 (tyrosinase related protein-2) transgenic mice. Isolated CD8$^+$ T cells were stained with carboxyfluorescein succinimidyl ester (CSFE, 5 µM) and washed 3 times, then $2.5\times10^5$ labeled T cells were added to the DC cultures. After another 36 hours of co-culture, cells were incubated for 24-hours with either medium, CpG (40, 10 and 1 µg/mL), uncoated-PBNPs (1 mg/mL and 2×, 4×, and 8× dilutions thereof), or CpG-PBNPs (1 mg/mL PBNPs coated with 40 µg/mL CpG and 2×, 4×, and 8× dilutions thereof). The treated co-cultures were then collected by centrifugation (800 g, 5 minutes), washed twice in FACS buffer, and blocked with anti-CD16/CD32. The cells were finally stained for 20 minutes at room temperature (23° C.±3° C.) using an anti-CD8 antibody. After staining, cells were washed twice and resuspended in FACS buffer containing DAPI for analysis by flow cytometry. All flow cytometry data was conducted by using FlowJo software.

Flow cytometry analysis of the stained co-cultures showed that T cell proliferation was increased in CpG-PBNP-treated cells compared to medium-treated cells (FIG. 8). These results suggest that treatment with CpG-PBNP correlates with the level of T cell proliferation, a marker of T cell activation, resulting from free CpG treatment.

Example 8

In vitro analysis of the known biochemical markers of immunogenic cell death (ICD) (ATP, high-motility group box 1, and calreticulin) was determined after Neuro2a cells were treated with uncoated-PBNPs to administer photothermal therapy (PBNP-PTT) to said cells. Briefly, ten million Neuro2a cells suspended in 1 mL PBS in a 1.7 mL microcentrifuge tube were treated with varying thermal doses of PBNP-PTT as follows: 1) 0.75 W NIR laser; 2) >1 W laser; 3) 0.75 W NIR laser+0.05 mg/mL uncoated-PBNP; 4) 0.75 W NIR laser+0.1 mg/mL uncoated-PBNP; and, 5) >1 W NIR laser+0.16 mg/mL uncoated PBNP. During the 10 minutes treatment period, the temperatures reached during PBNP-PTT were measured using a FLIR thermal camera at one minute intervals (FIG. 9A).

Next, the expression of ICD markers (ATP release, HMGB1 release, and surface calreticulin expression) was assessed in the PBNP-PTT-treated Neuro2a cells. For ICD marker analysis, cell suspensions first treated as described above, were then washed, stained with fluorescent antibodies against HMGB1 (intracellular) and calreticulin (extracellular), and flow cytometry was performed. For intracellular ATP presence, cells were washed after in vitro PBNP-PTT and an ATP-based luminescent-based assay was performed. When analyzing the results, it was noted that in order to suggest that the treated cells are undergoing ICD, intracellular ATP and HMGB1 should be decreased, and surface calreticulin expression should be increased, when compared with untreated controls. All three markers should be present in order to classify the cells undergoing ICD.

Here, in terms of ATP secretion (FIG. 9B) and surface calreticulin expression (FIG. 9D), all temperatures/thermal doses above 50° C. showed notably lower intracellular ATP and higher surface calreticulin expression as compared with controls. However, in terms of HMGB1 release (FIG. 9C), only the 50.7° C. group and 61.1° C. group exhibited >30% change in intracellular HMGB1 compared with untreated controls. Cells heated to 84.3° C. did not exhibit a marked decrease in intracellular HMGB1 suggesting that this higher temperature may not elicit ICD when compared with the lower temperature groups (i.e., the 50.7 and 61.1° C. groups). These observations suggest that PBNP-PTT-treated Neuro2a cells exhibit a window of ICD, i.e., ICD increases as temperature rises to an average temperature of ≈60° C., and then it decreases as temperature rises further to 80° C. and higher. Here, the 50.7 and 61.1° C. temperature groups (outlined in FIGS. 9B-9D) are the only temperature groups to satisfy all three consensus guidelines for ICD (ATP release, HMGB1 release, and increased calreticulin expression). This indicates that more is not necessarily better in this context, and that an optimal temperature window exists for eliciting ICD by PBNP-PTT.

In vitro analysis of ICD markers following photothermal therapy with CpG-PBNPs (CpG-PBNP-PTT) was also performed in Neuro2a cells. Here, ten million Neuro2a cells suspended in 1 mL PBS in a 1.7 mL microcentrifuge tube were treated as follows: 1) medium (vehicle); 2) 0.05 mg/mL CpG-PBNP; 3) 0.1 mg/mL CpG-PBNP; 4) 0.05 mg/mL uncoated-PBNP; 5) 0.1 mg/mL uncoated-PBNP; 6) 0.75 W NIR laser (PTT)+0.05 mg/mL CpG-PBNP; 7) 0.75 W NIR laser (PTT)+0.1 mg/mL CpG-PBNP; 8) 0.75 W NIR laser (PTT)+0.05 mg/mL uncoated-PBNP; 9) 0.75 W NIR laser (PTT)+0.1 mg/mL uncoated-PBNP; and, 10) 0.75 W NIR laser alone. Next, the expression of ICD markers (ATP release, HMGB1 release, and surface calreticulin expression) were assessed in the treated Neuro2a cells as described above.

After CpG-PBNP-PTT, a decrease in intracellular ATP was observed, which was correlated to cell death, compared to Neuro2a cells treated with controls (vehicles, PBNP only, CpG-PBNP only, and laser alone (FIG. 10A). These results showed that PTT, both done with PBNPs and CpG-PBNPs lead to tumor cell death. When looking at the markers of ICD, CpG-PBNP-PTT showed notably lower intracellular ATP (FIG. 10D), higher intracellular HMGB-1 secretion (FIG. 10B), and higher surface calreticulin expression (FIG. 10C) compared with controls. These findings suggest that CpG-PBNP-PTT is able to induce effective killing and ICD in Neuro2a cells, causing immune cell engagement by means of endogenous adjuvant release.

Example 9

To test the efficacy of CpG-PBNP-PTT in treating neuroblastoma, an in vivo mouse model of neuroblastoma was developed. For establishing a murine neuroblastoma model, one million Neuro2a cells suspended in phosphate-buffered saline were injected subcutaneously in the shaved backs of 4-6 week old female A1:1 mice, as previously described. All the treatments commenced after the tumors reached a diameter of at least 5 mm (~60 mm³). Neuro2a tumor-bearing mice (~5 mm tumor diameters, n=10/group) were divided into 5 groups as shown in FIG. 11A and described as follows: 1) vehicle (no treatment, PBS): 2) free CpG (10 uL CpG injected intratumorally on days 0, 2, and 5): 3) free CpG-PBNPs (2 µg conjugated on the PBNPs injected intratumorally on days 0, 2); 4) PBNP-PTT (50 µL of 1 mg/mL uncoated-PBNPs intratumorally, irradiated at 0.75 W for 10 minutes); and, 5) CpG-PBNP-PTT (50 µL of 1 mg/mL CpG-PBNPs, 2 µg bound CpG, irradiated at 0.75 W for 10 minutes, CpG-PBNPs boost on days 2 and 5).

Temperatures during PTT, as measured using a FUR thermal camera, reached an average tumor temperature of 60° C. (FIG. 11B), which corresponds to the temperature needed to elicit tumor cell death and ICD in Neuro2a-bearing mice. Results showed that localized treatment with CpG-PBNP-PTT was more effective in tumor eradication as evidenced by complete tumor eradication and slower tumor growth compared to controls (FIG. 11C and FIGS. 12A-12E). Mice treated with the CpG-PBNP-PTT resulted in complete tumor regression and long-term survival in 70% of the treated mice at 60-110 days post-treatment (FIG. 11D). CpG-PBNP-PTT resulted in long-term survival (survival >60 days post treatment) in 70% of the treated tumor-bearing mice, which was significantly higher (p<0.05) than the long-term survival observed in tumor-bearing mice in all other treatment groups. Results show for the first time that CpG-PBNP-PTT can be used to generate immunological antitumor cancer responses by delivering both antigen and adjuvant in a single nanoparticle platform.

Next, it was investigated whether CpG-PBNP-PTT conferred protection in long-term surviving mice that were rechallenged with the original tumor cells (Neuro2a) (FIG. 11E). The studies consisted of two groups: 1) naïve group where untreated mice were challenged with $10^6$ Neuro2a cells; and, 2) rechallenged group: where long-term surviving mice where rechallenged with $10^6$ Neuro2a cells after at least 60 days of tumor-free survival (n>=7/group for this study). Remarkably, all of the CpG-PBNP-PTT-treated, long-term surviving mice exhibited protection against the tumor rechallenge, and these mice rapidly eliminated the rechallenged tumors compared with control mice where rapid tumor progression was observed. Further, the surviving mice survived for >60 days post tumor rechallenged compared with naïve mice that had to be euthanized due to high tumor burden 12-14 days post-challenge. These data suggest the potential of dual delivery of antigen and adjuvant by means of CpG-PBNP-PTT in conferring immunity and protection in long-term surviving mice against tumor rechallenge/recurrence.

Introduction to Examples 10-16

PBNP-PTT provides a platform for cell destruction and an upregulation of an immune response in cancer cells as shown, for example, in FIGS. 1 and 9A-9D. Immunogenic cell death (ICD) is a favorable cell death phenotype, in part allowing for immunological memory against recurrent to metastatic disease. One characteristic of ICD is the release or exposure of danger-associated molecular patterns (DAMPs) from dying cancer cells. DAMPs are molecules released by stressed cells undergoing necrosis that act as endogenous danger signals to promote and exacerbate the inflammatory response. PBNP-PTT stimulations of DAMPs from dying cells may depend on the cell type, the conditions of PBNP-PTT, or may simply not stimulate sufficient DAMPs to propagate downstream signaling. As an example of how to overcome these drawbacks, described herein are PBNPs biofunctionalized with DAMPs. Description of the synthesis and characterization of DAMPs-PBNPs and studies to determine the effectiveness of DAMPs-PBNPs in photothermal therapy are outlined below.

Example 10

PBNPs were synthesized by mixing potassium ferrocyanide ($K_4[Fe(CN)_6] \cdot 3H_2O$) and iron(III) chloride ($FeCl_3 \cdot 6H_2O$). Specifically, an aqueous solution of 6.8 mg $FeCl_3 \cdot 6H_2O$ ($2.5 \times 10^{-5}$ mol) in 5 mL of Milli-Q water was added under vigorous stirring to an aqueous solution containing 10.6 mg of $K_4Fe(CN)_6 \cdot 3H_2O$ ($2.5 \times 10^{-5}$ mol) in 5 mL of Milli-Q water. After stirring for 15 minutes, the precipitate was isolated by centrifugation (20 000 g for 10 minutes) and rinsed by sonication (5 seconds, high power) in Milli-Q water. The isolation and rinsing steps were repeated three times before the particles were resuspended by sonication in Milli-Q water.

PBNPs were next directly coated with a DAMPs protein, specifically HMGB1 to yield DAMPs-PBNPs. Specifically, PBNPs (concentrations ranging from 0.01-10 mg/mL, typically 1 mg/mL) were contacted with aqueous suspensions (water, PBS, etc.) of HMGB1 at concentrations (0.1-100 µg/mL, typically 10 µg/mL) at room temperature for durations ranging from 5 minutes to 1 day (typically around 1 hour). In the coating process, HMGB1 was absorbed onto the PBNPs. The coating step was performed at temperatures ranging from 4° C. to room temperature (23° C.±3° C.). After coating, the particles were collected by centrifugation or the HMGB1 was removed via techniques such as dialysis.

Alternatively, HMGB1 was bound to PBNPs through covalent bonds. Where the coating process used covalent bonds to attach the HMGB1 to PBNPs, the HMGB1 was contacted with PBNPs using N-hydroxysuccinimide/1-Ethyl-3-(3-dimethylaminopropyl)carbodiimide (NHS/EDAC) to couple the carboxyl groups of PBNPs (containing citrate) to the amine groups of HMGB1.

Example 11

To guarantee that coating PBNPs with DAMPs does not affect the intrinsic characteristics of PBNPs, properties of DAMPs-PBNPs were measured and compared to uncoated PBNPs. The size (hydrodynamic diameter) of uncoated PBNPs and DAMPs-PBNPs was measured using dynamic light scattering (DLS) on a Zetasizer Nano ZS (Malvern Instruments, Malvern, UK). The Vis-NIR absorbance of the nanoparticles was measured on the Genesys 10S spectrophotometer using the VISIONlite software.

Uncoated PBNPs had an average diameter of about 90 nm (FIG. 13A). Multiday stability of DAMPs-PBNPs was assessed by measuring hydrodynamic size distributions after 1 day, 3 days and 7 days of storage in ultrapure water using DLS, zeta potential, and UV-NIR absorbance. The hydrodynamic diameter of DAMPs-PBNPs at each time point was compared to the diameter of uncoated PBNPs. The DAMPs-PBNPs had a constant mean hydrodynamic diameter at all three days (day 1, day 3, and day 7) which did not deviate from average diameter of uncoated PBNPs (FIG. 13B). These data demonstrated that DAMPs-PBNPs were stable over time.

Example 12

The amount of DAMPs encapsulated in the DAMPs-PBNPs was measured by UV-Vis spectrophotometry to assess protein concentration as known in the art. Overall, the concentration of free DAMPs was 16.4% higher than encapsulated DAMPs (FIG. 14), demonstrating the therapeutic encapsulation efficiently of DAMPs.

Example 13

The photothermal therapy (PTT) capabilities of DAMPs-PBNPs were tested in vitro (Neuro2a cells) as a function of concentration by varying the concentration of the nanoparticles from 0.025 mg/mL to 0.5 mg/L at a fixed laser fluence (power density) of 0.75 W for 10 minutes. Additionally, the photothermal therapy (PIT) capabilities of DAMPs-PBNPs were measured in comparison to those of uncoated PBNPs as a function of laser fluence (0.24 W-1.25 W) by irradiating either uncoated PBNPs or DAMPs-PBNPs at a concentration of 1 mg/mL for 10 minutes.

Photothermal heating of various concentrations of uncoated PBNPs and DAMPs-PBNPs irradiated by an 808 nm NIR laser for 10 minutes at 0.75 W laser power showed that temperatures increase with increasing CpG-PBNP concentrations (FIG. 15). The photothermal heating effect on 1 mg/mL uncoated PBNPs using varying NIR laser powers for 10 minutes was dependent on the power of the incident laser, and was observed to increase with increasing laser powers (FIG. 16A). Similarly, the photothermal heating effect on 1 mg/mL DAMPs-PBNPs using varying NIR laser powers for 10 minutes was also dependent on the power of the incident laser, and was observed to increase with increasing laser powers (FIG. 16B).

Collectively, these results show that coating PBNPs with DAMPs does not affect the heating abilities, and that DAMPs-PBNPs can withstand the high temperatures required for therapeutic usage.

Example 14

Intrinsic cytotoxicity of uncoated PBNPs and DAMPs-PBNPs was assessed in vitro using the murine neuroblastoma cell line Neuro2a. Neuro2a cells were seeded at a cell density of 50,000 cells per well, and incubated with either vehicle or varying concentrations of uncoated PBNPs or DAMPs-PBNPs (0.001-0.1 mg/mL) for 24 hours. After the 24-hour incubation period, cell viability was assessed using a luminescent cell viability assay. Neuro2a cell viability was not significantly changed among treatment groups (FIG. 17). The data indicate that DAMPS-PBNPs are non-toxic to cells.

Example 15

To test the killing efficacy of DAMPs-PBNP-PTT, Neruro2a cells were first seeded onto well plates (approximately 10,000 to 1 million cells per well). Subsequently, either 0.05 mg/ml uncoated PBNPs, 0.05 mg/ml DAMPs-PBNPs, 0.1 mg/ml uncoated PBNPs, 0.1 mg/ml DAMPS-PBNPs, or vehicle ("0") was added to the Neruro2a cells. Next, treated cells were irradiated by an 808 nm NIR laser for 10 minutes at 0.75 W laser power. The cells were then returned to a tissue culture incubator and a cell viability assay was conducted 24 hours after irradiation. As shown in FIG. 18, both uncoated PBNP-PTT and DAMPs-PBNP-PTT killed Neruro2a cells in a concentration-dependent manner.

Example 16

Neuro2a cells (approximately 1 million cells/mL) were coincubated with 0.1 mg/ml DAMP-PBNPs. Coincubated cells were then irradiated with either 1) an external beam laser (PTT); or 2) a laser connected to a 0.85 micrometer spherical diffuser (PTTi). PTT and PTTi were performed at 80 mW and 100 mW laser power for 0-10 minutes. The temperatures resulting from irradiation at each time point were monitored with a thermal camera and/or a thermocouple. Data show that DAMP-PBNPs have a high photothermic conversion efficiency when irradiated both intracellularly and at the cell surface (FIGS. 19A and 19B).

What is claimed is:
1. A biofunctionalized nanocomposite, comprising:
   (a) a core comprising Prussian blue materials;
   (b) a positively charged biocompatible coating comprising polyethylenimine (PEI) having an average molecular weight (MW) of about 2000 daltons; and
   at least one CpG oligodeoxynucleotide attached to the outer surface of the positively charged biocompatible coating.
2. The biofunctionalized nanocomposite of claim 1, wherein the Prussian blue materials are iron hexacyanoferrate (II) compounds.

3. The biofunctionalized nanocomposite of claim 1, wherein the Prussian blue materials are represented by general formula (I):

$$A_xB_yM_4[M'(CN)_6]_z \cdot nH_2O \quad (I)$$

wherein:
- A represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;
- B represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;
- M represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;
- M' represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;
- x is from 0.1 to about 1;
- y is from 0.1 to about 1;
- z is from 0.1 to about 4; and
- n is from 0.1 to about 24.

4. The biofunctionalized nanocomposite of claim 1, wherein at least 75% of the outer surface of the positively charged biocompatible coating has a CpG oligodeoxynucleotide attached thereto.

5. The biofunctionalized nanocomposite of claim 1, wherein the average molecular weight of the PEI is 2000 Daltons.

6. The biofunctionalized nanocomposite of claim 1, wherein the biofunctionalized nanocomposite is a photothermal therapy agent.

7. The biofunctionalized nanocomposite of claim 6, wherein the positively charged biocompatible coating further comprises an imaging agent.

* * * * *